US011399942B2

(12) United States Patent
Annest et al.

(10) Patent No.: US 11,399,942 B2
(45) Date of Patent: Aug. 2, 2022

(54) TREATING DYSFUNCTIONAL CARDIAC TISSUE

(71) Applicant: BioVentrix, Inc., San Ramon, CA (US)

(72) Inventors: Lon S. Annest, New York, NY (US); Claudio Argento, Los Gatos, CA (US); William Butler, San Ramon, CA (US); Ernest Heflin, Pleasanton, CA (US)

(73) Assignee: BioVentrix, Inc., San Ramon, CA (US)

( * ) Notice: Subject to any disclaimer, the term of this patent is extended or adjusted under 35 U.S.C. 154(b) by 127 days.

(21) Appl. No.: 16/838,866

(22) Filed: Apr. 2, 2020

(65) Prior Publication Data
US 2020/0229928 A1 Jul. 23, 2020

Related U.S. Application Data

(63) Continuation of application No. 15/894,753, filed on Feb. 12, 2018, now Pat. No. 10,624,744, which is a
(Continued)

(51) Int. Cl.
*A61B 17/00* (2006.01)
*A61B 17/04* (2006.01)
(Continued)

(52) U.S. Cl.
CPC ........ *A61F 2/2487* (2013.01); *A61B 17/0057* (2013.01); *A61B 17/00234* (2013.01);
(Continued)

(58) Field of Classification Search
CPC ............. A61F 2/2487; A61F 2002/249; A61B 17/00234; A61B 17/0057; A61B 17/0401;
(Continued)

(56) References Cited

U.S. PATENT DOCUMENTS

| 4,007,743 A | 2/1977 | Blake |
| 5,295,958 A | 3/1994 | Shturman |

(Continued)

FOREIGN PATENT DOCUMENTS

| EP | 1 078 644 A1 | 2/2001 |
| WO | 98-29041 A1 | 7/1998 |

(Continued)

OTHER PUBLICATIONS

U.S. Pat. No. 10,624,744, U.S. Appl. No. 15/894,753, filed Feb. 12, 2018.

(Continued)

*Primary Examiner* — Paula J Stice
(74) *Attorney, Agent, or Firm* — Nixon & Vanderhye P.C.

(57) ABSTRACT

Medical devices, systems, and methods reduce the distance between two points in tissue, often for treatment of congestive heart failure and often in a minimally invasive manner. An anchor is inserted along an insertion path through a first wall of the heart. An arm of the anchor is deployed and rotationally positioned according to a desired alignment. Application of tension to the anchor may draw the first and second walls of the heart into contact along a desired contour so as to effect a desired change in the geometry of the heart. Additional anchors may be inserted and aligned with the first anchor to close off a portion of a ventricle such that the ventricle is geometrically remodeled and disease progression is reversed, halted, and/or slowed.

19 Claims, 70 Drawing Sheets

Related U.S. Application Data continuation of application No. 15/341,945, filed on Nov. 2, 2016, now Pat. No. 9,889,008, which is a continuation of application No. 14/636,068, filed on Mar. 2, 2015, now Pat. No. 9,486,206, which is a continuation of application No. 13/949,025, filed on Jul. 23, 2013, now Pat. No. 8,968,175, which is a continuation of application No. 12/245,040, filed on Oct. 3, 2008, now Pat. No. 8,491,455.

(60) Provisional application No. 61/082,438, filed on Jul. 21, 2008, provisional application No. 60/977,286, filed on Oct. 3, 2007.

(51) Int. Cl.
*A61F 2/24* (2006.01)
*A61B 50/30* (2016.01)
*A61M 25/01* (2006.01)
*A61B 17/06* (2006.01)
*A61M 25/09* (2006.01)
*A61M 29/02* (2006.01)
*A61B 17/02* (2006.01)

(52) U.S. Cl.
CPC ...... *A61B 17/0401* (2013.01); *A61B 17/0467* (2013.01); *A61B 17/0469* (2013.01); *A61B 17/06066* (2013.01); *A61B 50/30* (2016.02); *A61M 25/0138* (2013.01); *A61M 25/0147* (2013.01); *A61M 25/09* (2013.01); *A61M 29/02* (2013.01); *A61B 17/0487* (2013.01); *A61B 2017/00243* (2013.01); *A61B 2017/00247* (2013.01); *A61B 2017/00469* (2013.01); *A61B 2017/00561* (2013.01); *A61B 2017/00601* (2013.01); *A61B 2017/00867* (2013.01); *A61B 2017/0237* (2013.01); *A61B 2017/0404* (2013.01); *A61B 2017/048* (2013.01); *A61B 2017/0408* (2013.01); *A61B 2017/0417* (2013.01); *A61B 2017/0464* (2013.01); *A61B 2017/0488* (2013.01); *A61B 2017/0496* (2013.01); *A61B 2017/061* (2013.01); *A61B 2017/0608* (2013.01); *A61B 2017/06052* (2013.01); *A61B 2017/06176* (2013.01); *A61F 2002/249* (2013.01)

(58) Field of Classification Search
CPC .......... A61B 17/0469; A61B 17/06066; A61B 50/30; A61B 2017/00243; A61B 2017/00247; A61B 2017/00469; A61B 2017/00867; A61B 2017/0237; A61B 2017/0464; A61B 2017/048; A61B 2017/061; A61B 2017/06176; A61M 25/0138; A61M 25/0147; A61M 25/09; A61M 29/02

See application file for complete search history.

(56) References Cited

U.S. PATENT DOCUMENTS

| | | | |
|---|---|---|---|
| 5,336,252 A | 8/1994 | Cohen | |
| 5,482,037 A | 1/1996 | Borghi | |
| 5,755,697 A | 5/1998 | Jones et al. | |
| 5,810,884 A | 9/1998 | Kim | |
| 5,830,224 A | 11/1998 | Cohn et al. | |
| 5,865,730 A | 2/1999 | Fox et al. | |
| 5,961,440 A | 10/1999 | Schweich, Jr. et al. | |
| 6,010,476 A | 1/2000 | Saadat | |
| 6,022,336 A * | 2/2000 | Zadno-Azizi | A61B 17/22 604/101.05 |
| 6,045,497 A | 4/2000 | Schweich et al. | |
| 6,050,936 A | 4/2000 | Schweich, Jr. et al. | |
| 6,059,715 A | 5/2000 | Schweich, Jr. et al. | |
| 6,080,182 A | 6/2000 | Shaw et al. | |
| 6,125,852 A | 10/2000 | Stevens et al. | |
| 6,155,968 A | 12/2000 | Wilk | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,166,684 A | 12/2000 | Yoshikawa et al. | |
| 6,258,021 B1 | 7/2001 | Wilk | |
| 6,260,552 B1 | 7/2001 | Mortier et al. | |
| 6,406,420 B1 | 6/2002 | McCarthy et al. | |
| 6,494,825 B1 | 12/2002 | Talpade | |
| 6,511,416 B1 | 1/2003 | Green et al. | |
| 6,572,529 B2 | 6/2003 | Wilk | |
| 6,616,684 B1 | 9/2003 | Vidlund et al. | |
| 6,623,508 B2 | 9/2003 | Shaw et al. | |
| 6,705,988 B2 | 3/2004 | Spence et al. | |
| 6,709,382 B1 | 3/2004 | Horner | |
| 6,723,038 B1 | 4/2004 | Schroeder et al. | |
| 6,746,471 B2 | 6/2004 | Mortier et al. | |
| 6,776,754 B1 | 8/2004 | Wilk | |
| 6,808,488 B2 | 10/2004 | Mortier | |
| 6,859,662 B2 | 2/2005 | Bombardini | |
| 6,890,295 B2 | 5/2005 | Michels et al. | |
| 7,146,225 B2 | 12/2006 | Guenst et al. | |
| 7,326,177 B2 | 2/2008 | Williamson | |
| 7,390,329 B2 | 6/2008 | Westra et al. | |
| 7,431,691 B1 | 10/2008 | Wilk | |
| 7,637,924 B2 | 12/2009 | Gifford et al. | |
| 7,722,523 B2 | 5/2010 | Mortier et al. | |
| 7,753,923 B2 | 7/2010 | St. Goar et al. | |
| 7,766,816 B2 | 8/2010 | Chin et al. | |
| 7,785,248 B2 | 8/2010 | Annest et al. | |
| 7,942,854 B1 | 5/2011 | Von Oepen et al. | |
| 8,066,766 B2 | 11/2011 | To et al. | |
| 8,123,668 B2 | 2/2012 | Annest et al. | |
| 8,268,009 B2 | 9/2012 | Teitelbaum et al. | |
| 8,394,008 B2 | 3/2013 | Annest et al. | |
| 8,425,402 B2 | 4/2013 | Annest et al. | |
| 8,449,442 B2 | 5/2013 | Annest et al. | |
| 8,491,455 B2 | 7/2013 | Annest et al. | |
| 8,506,474 B2 | 8/2013 | Chin et al. | |
| 8,636,639 B2 | 1/2014 | Annest et al. | |
| 8,968,175 B2 | 3/2015 | Annest et al. | |
| 8,979,750 B2 | 3/2015 | Bladel et al. | |
| 8,986,189 B2 | 3/2015 | Chin et al. | |
| 9,039,594 B2 | 5/2015 | Annest et al. | |
| 9,044,231 B2 | 6/2015 | Annest et al. | |
| 9,095,363 B2 | 8/2015 | Bladel et al. | |
| 9,119,720 B2 | 9/2015 | Chin et al. | |
| 9,173,711 B2 | 11/2015 | Butler et al. | |
| 9,173,712 B2 | 11/2015 | Annest et al. | |
| 9,211,115 B2 | 12/2015 | Annest et al. | |
| 9,259,319 B2 | 2/2016 | Chin et al. | |
| 9,402,722 B2 | 8/2016 | Annest et al. | |
| 9,486,206 B2 | 11/2016 | Annest et al. | |
| 9,526,618 B2 | 12/2016 | Chin et al. | |
| 9,889,008 B2 | 2/2018 | Annest et al. | |
| 10,624,744 B2 | 4/2020 | Annest et al. | |
| 2001/0025171 A1 | 9/2001 | Mortier et al. | |
| 2001/0041821 A1 | 11/2001 | Wilk | |
| 2002/0058855 A1 | 5/2002 | Schweich, Jr. et al. | |
| 2002/0077524 A1 | 6/2002 | Schweich, Jr. et al. | |
| 2002/0077655 A1 | 6/2002 | Frova | |
| 2002/0120298 A1 | 8/2002 | Kramer et al. | |
| 2002/0123768 A1 | 9/2002 | Gilkerson et al. | |
| 2002/0169359 A1 | 11/2002 | McCarthy et al. | |
| 2002/0169360 A1 | 11/2002 | Taylor et al. | |
| 2002/0188170 A1 | 12/2002 | Santamore et al. | |
| 2002/0198563 A1 | 12/2002 | Gainor et al. | |
| 2003/0032979 A1 | 2/2003 | Mortier et al. | |
| 2003/0163165 A1 | 8/2003 | Bornzin et al. | |
| 2003/0166992 A1 | 9/2003 | Schweich, Jr. et al. | |
| 2003/0181928 A1 | 9/2003 | Vidlund et al. | |
| 2003/0181951 A1 | 9/2003 | Cates | |
| 2003/0220587 A1 | 11/2003 | Swenson | |
| 2003/0233022 A1 | 12/2003 | Vidlund et al. | |
| 2004/0064143 A1 | 4/2004 | Hicken et al. | |

(56) References Cited

U.S. PATENT DOCUMENTS

| | | |
|---|---|---|
| 2004/0082837 A1 | 4/2004 | Willis |
| 2004/0088035 A1 | 5/2004 | Guenst et al. |
| 2004/0138526 A1 | 7/2004 | Guenst |
| 2004/0167374 A1 | 8/2004 | Schweich |
| 2004/0167580 A1 | 8/2004 | Mann et al. |
| 2004/0225304 A1 | 11/2004 | Vidlund et al. |
| 2004/0249342 A1* | 12/2004 | Khosravi ........ A61M 25/10182 604/96.01 |
| 2004/0267306 A1 | 12/2004 | Blaeser et al. |
| 2005/0065506 A1 | 3/2005 | Phan |
| 2005/0075723 A1 | 4/2005 | Schroeder et al. |
| 2005/0096498 A1 | 5/2005 | Houser et al. |
| 2005/0137688 A1 | 6/2005 | Salahieh et al. |
| 2005/0143620 A1 | 6/2005 | Mortier et al. |
| 2005/0149115 A1 | 7/2005 | Roue et al. |
| 2005/0192599 A1 | 9/2005 | Demarais |
| 2005/0215851 A1 | 9/2005 | Kim et al. |
| 2005/0288613 A1 | 12/2005 | Heil Jr. |
| 2006/0004408 A1 | 1/2006 | Morris et al. |
| 2006/0079736 A1 | 4/2006 | Chin et al. |
| 2006/0131238 A1 | 6/2006 | Xu |
| 2006/0135962 A1 | 6/2006 | Kick et al. |
| 2006/0161040 A1 | 7/2006 | McCarthy et al. |
| 2006/0161238 A1 | 7/2006 | Hall |
| 2006/0167416 A1 | 7/2006 | Mathis et al. |
| 2006/0178550 A1 | 8/2006 | Jenson |
| 2006/0200002 A1 | 9/2006 | Guenst |
| 2006/0241340 A1 | 10/2006 | Schroeder et al. |
| 2006/0247672 A1 | 11/2006 | Vidlund et al. |
| 2006/0276684 A1 | 12/2006 | Speziali |
| 2007/0005018 A1 | 1/2007 | Tkebuchava |
| 2007/0010876 A1 | 1/2007 | Salahieh et al. |
| 2007/0049971 A1 | 3/2007 | Chin et al. |
| 2007/0055303 A1 | 3/2007 | Vidlund et al. |
| 2007/0073274 A1 | 3/2007 | Chin et al. |
| 2007/0112244 A1 | 5/2007 | McCarthy et al. |
| 2007/0161846 A1 | 7/2007 | Nikotic et al. |
| 2007/0203503 A1 | 8/2007 | Salahieh et al. |
| 2007/0265658 A1 | 11/2007 | Nelson et al. |
| 2007/0287884 A1 | 12/2007 | Schena |
| 2008/0058650 A1 | 3/2008 | Saadat et al. |
| 2008/0082132 A1 | 4/2008 | Annest et al. |
| 2008/0097148 A1 | 4/2008 | Chin et al. |
| 2008/0234717 A1 | 9/2008 | Bruszewski |
| 2008/0269551 A1 | 10/2008 | Annest et al. |
| 2008/0294251 A1 | 11/2008 | Annest et al. |
| 2009/0093670 A1 | 4/2009 | Annest et al. |
| 2009/0270980 A1 | 10/2009 | Schroeder et al. |
| 2009/0287165 A1 | 11/2009 | Drapeau et al. |
| 2009/0287304 A1 | 11/2009 | Dahlgren et al. |
| 2010/0010538 A1 | 1/2010 | Juravic et al. |
| 2010/0016655 A1 | 1/2010 | Annest et al. |
| 2010/0057000 A1 | 3/2010 | Melsheimer et al. |
| 2010/0268020 A1 | 10/2010 | Chin et al. |
| 2011/0160750 A1 | 6/2011 | Annest et al. |
| 2011/0270191 A1 | 11/2011 | Paul et al. |
| 2012/0190958 A1 | 7/2012 | Annest et al. |
| 2013/0090523 A1 | 4/2013 | Van Bladel et al. |
| 2013/0090672 A1 | 4/2013 | Butler et al. |
| 2013/0090684 A1 | 4/2013 | Van Bladel et al. |
| 2013/0096579 A1 | 4/2013 | Annest et al. |
| 2013/0324787 A1 | 12/2013 | Chin et al. |
| 2013/0325041 A1 | 12/2013 | Annest et al. |
| 2014/0031613 A1 | 1/2014 | Annest et al. |
| 2014/0051916 A1 | 2/2014 | Chin et al. |
| 2014/0330296 A1 | 11/2014 | Annest et al. |
| 2014/0350417 A1 | 11/2014 | Bladel et al. |
| 2015/0066082 A1 | 3/2015 | Moshe et al. |
| 2015/0066139 A1 | 3/2015 | Bladel et al. |
| 2015/0238182 A1 | 8/2015 | Annest et al. |
| 2016/0022422 A1 | 1/2016 | Annest et al. |
| 2016/0030026 A1 | 2/2016 | Bladel et al. |
| 2016/0089132 A1 | 3/2016 | Butler et al. |
| 2016/0095600 A1 | 4/2016 | Annest et al. |
| 2016/0120648 A1 | 5/2016 | Chin et al. |
| 2016/0206427 A1 | 7/2016 | Annest et al. |
| 2016/0262891 A1 | 9/2016 | Chin et al. |
| 2016/0338835 A1 | 11/2016 | Bladel et al. |

FOREIGN PATENT DOCUMENTS

| | | |
|---|---|---|
| WO | 00/06028 A1 | 2/2000 |
| WO | 01-28455 A1 | 4/2001 |
| WO | 2002/30335 A2 | 4/2002 |
| WO | 2003/032818 A3 | 4/2003 |
| WO | 2004-043267 A2 | 5/2004 |
| WO | 2005/092203 A1 | 10/2005 |
| WO | 2005-110280 A2 | 11/2005 |
| WO | 2006/044467 A2 | 4/2006 |
| WO | 2007/022519 A2 | 2/2007 |
| WO | 2013-049761 A1 | 4/2013 |

OTHER PUBLICATIONS

U.S. Pat. No. 9,889,008, U.S. Appl. No. 15/341,945, filed Nov. 2, 2016.

U.S. Pat. No. 9,486,206, U.S. Appl. No. 14/636,068, filed Mar. 2, 2015.

U.S. Pat. No. 8,968,175, U.S. Appl. No. 13/949,025, filed Jul. 23, 2013.

U.S. Pat. No. 8,491,455, U.S. Appl. No. 12/245,040, filed Oct. 3, 2008.

* cited by examiner

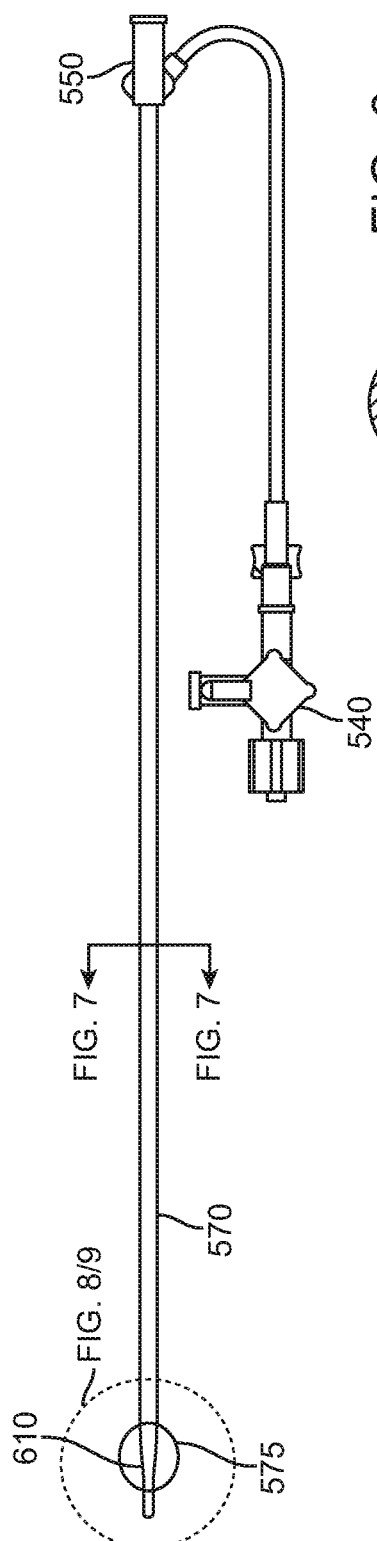
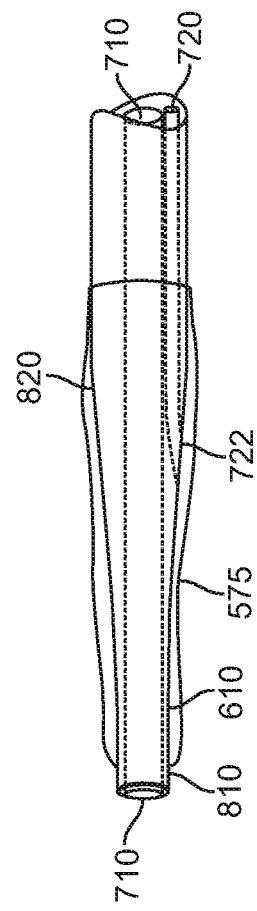
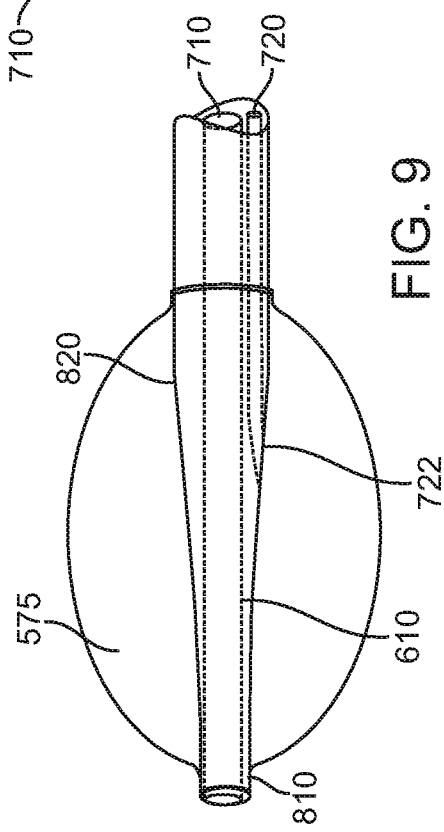
FIG. 6
FIG. 7
FIG. 8
FIG. 9

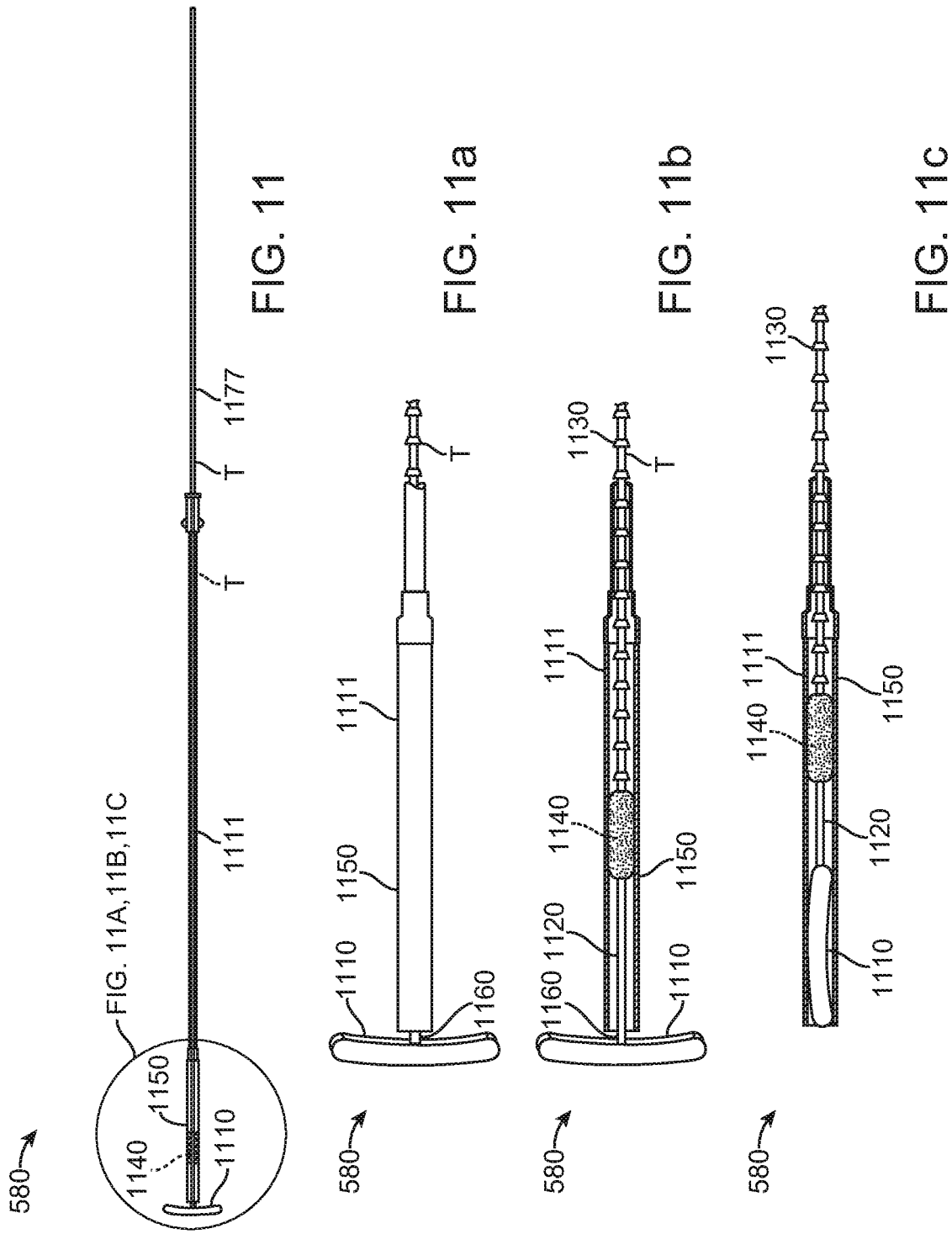

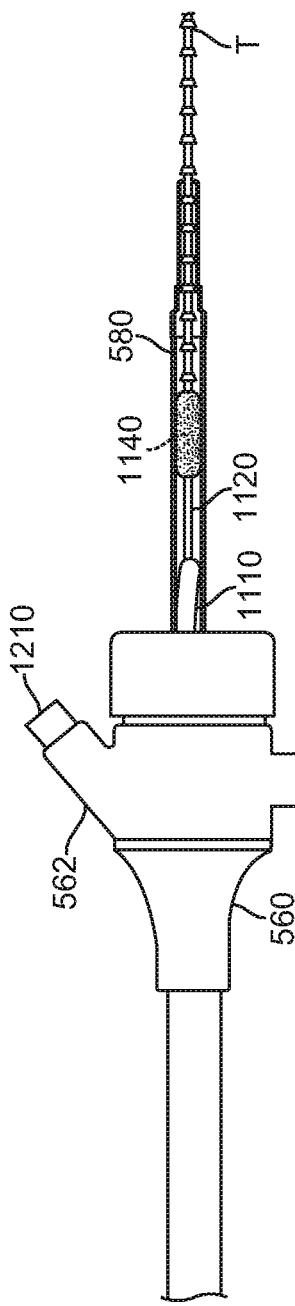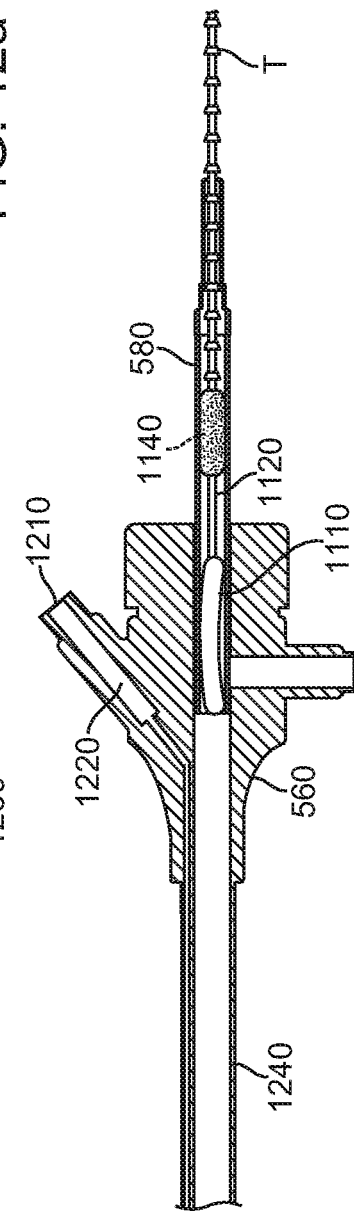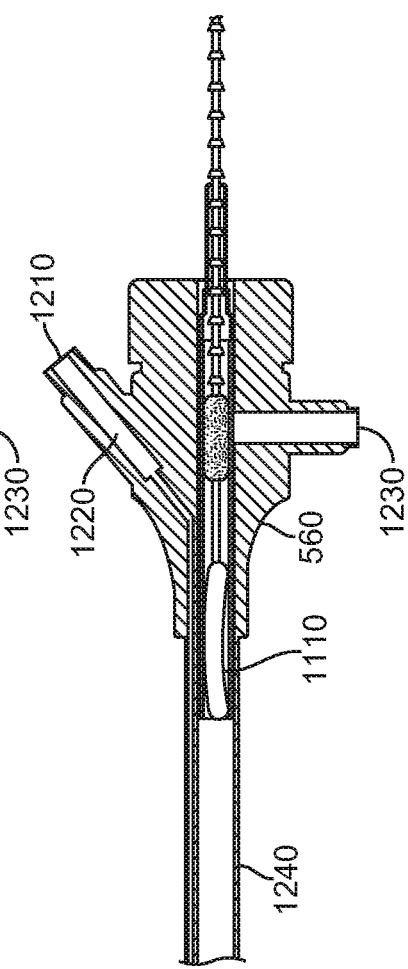

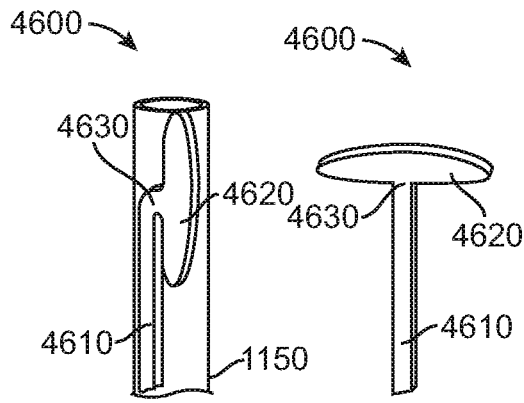 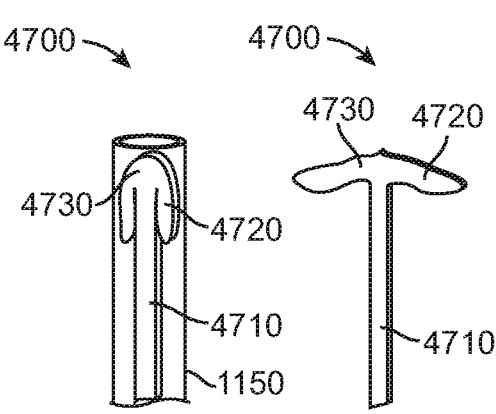
FIG. 46A  FIG. 46B        FIG. 47A  FIG. 47B
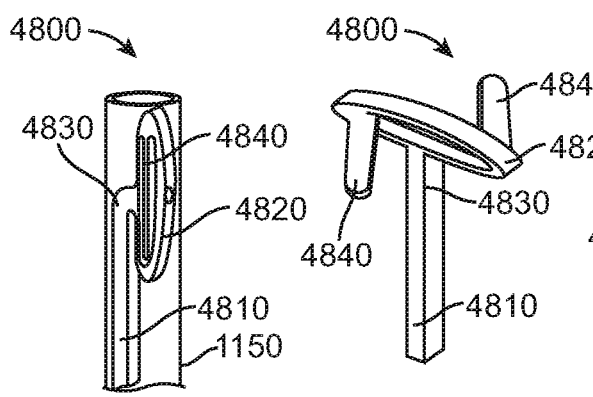 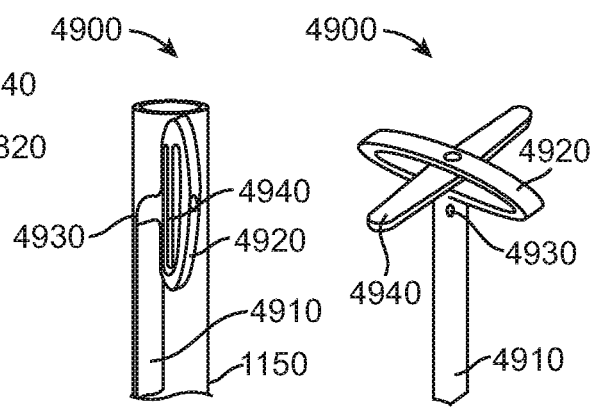
FIG. 48A  FIG. 48B        FIG. 49A  FIG. 49B
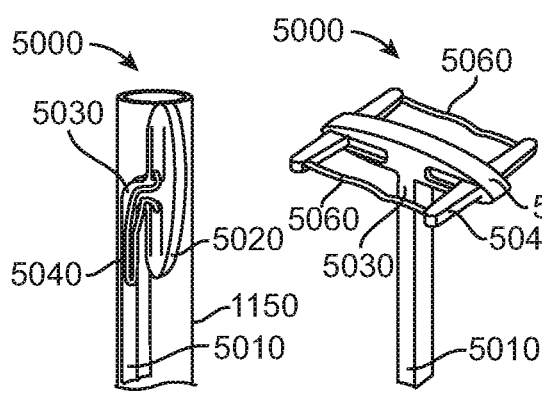 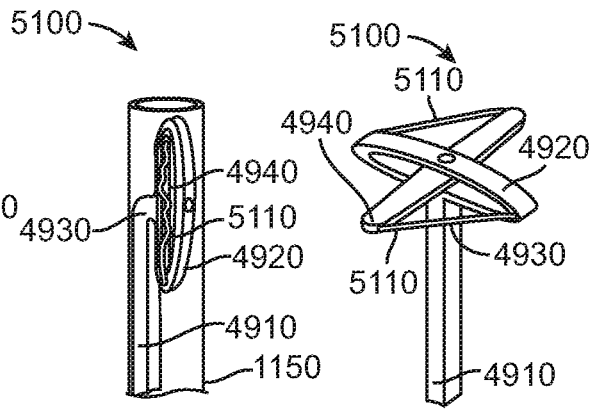
FIG. 50A  FIG. 50B        FIG. 51A  FIG. 51B

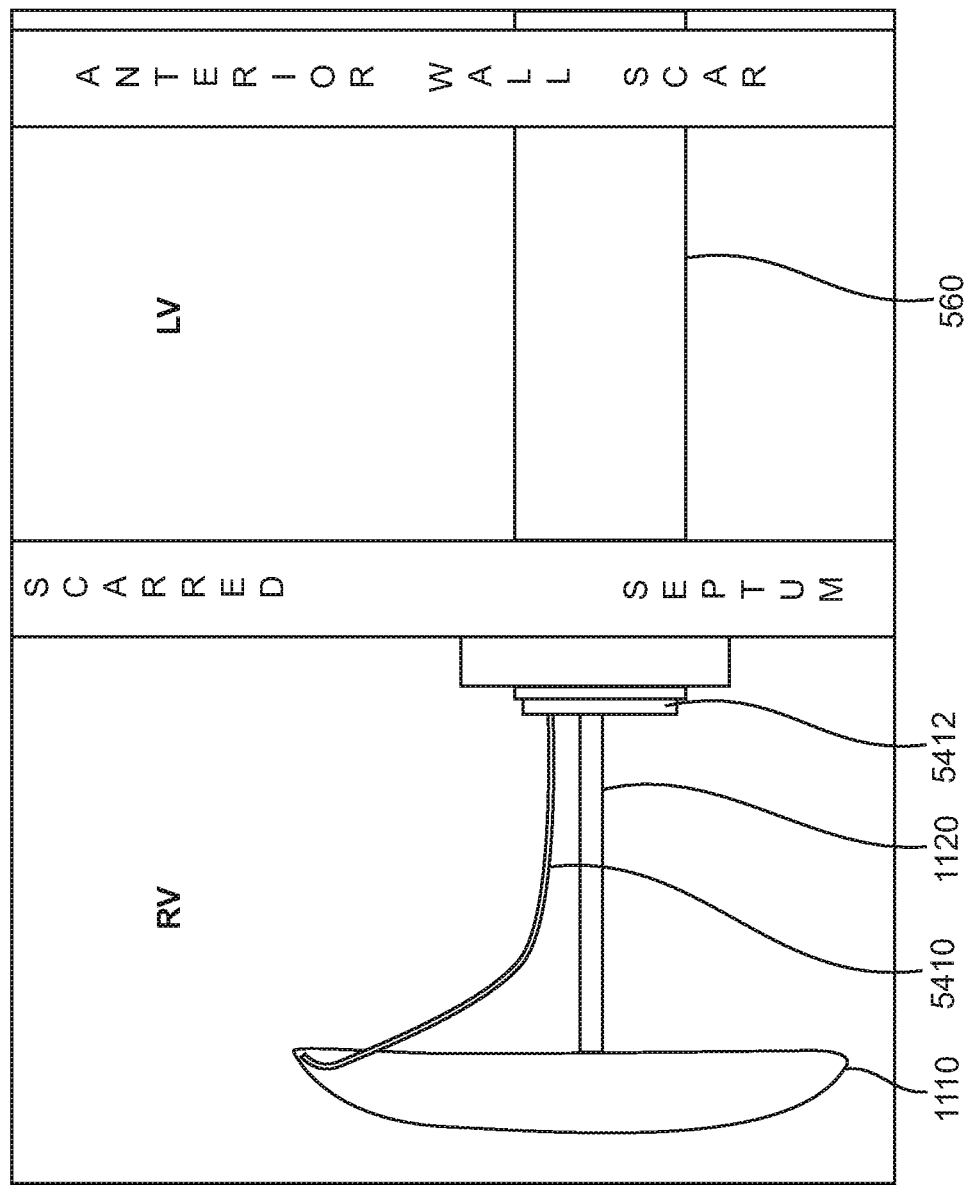

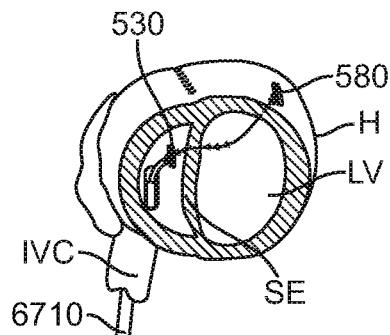
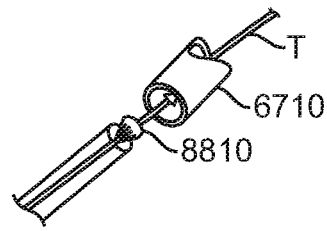
FIG. 87     FIG. 88
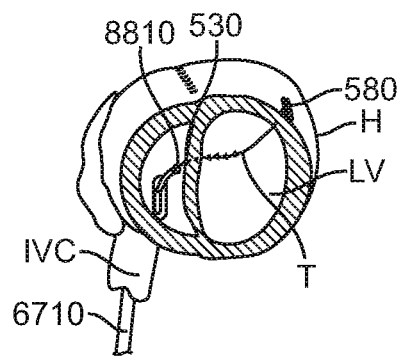
FIG. 89
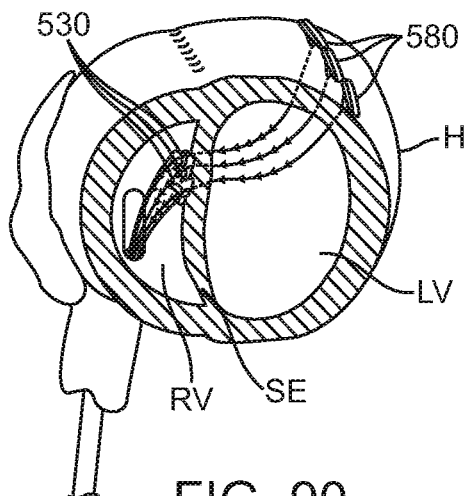
FIG. 90

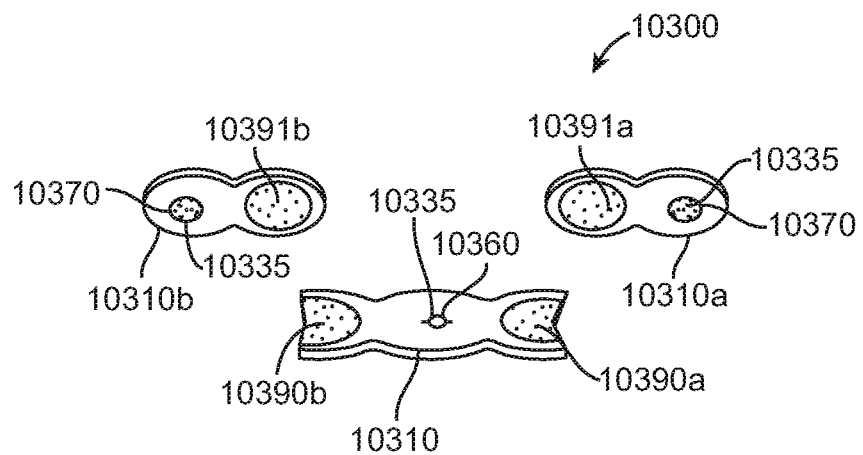
FIG. 103
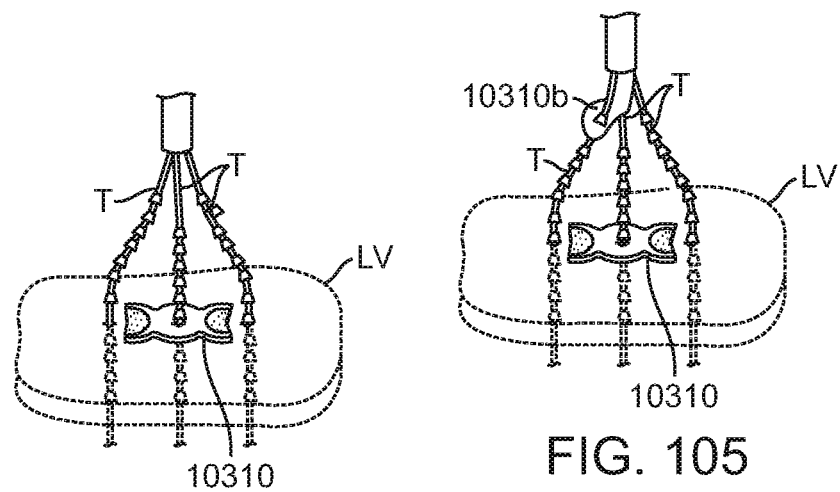
FIG. 104
FIG. 105
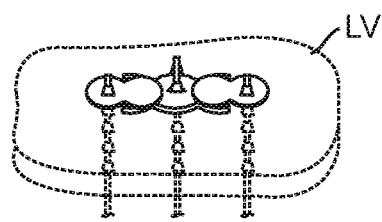
FIG. 106

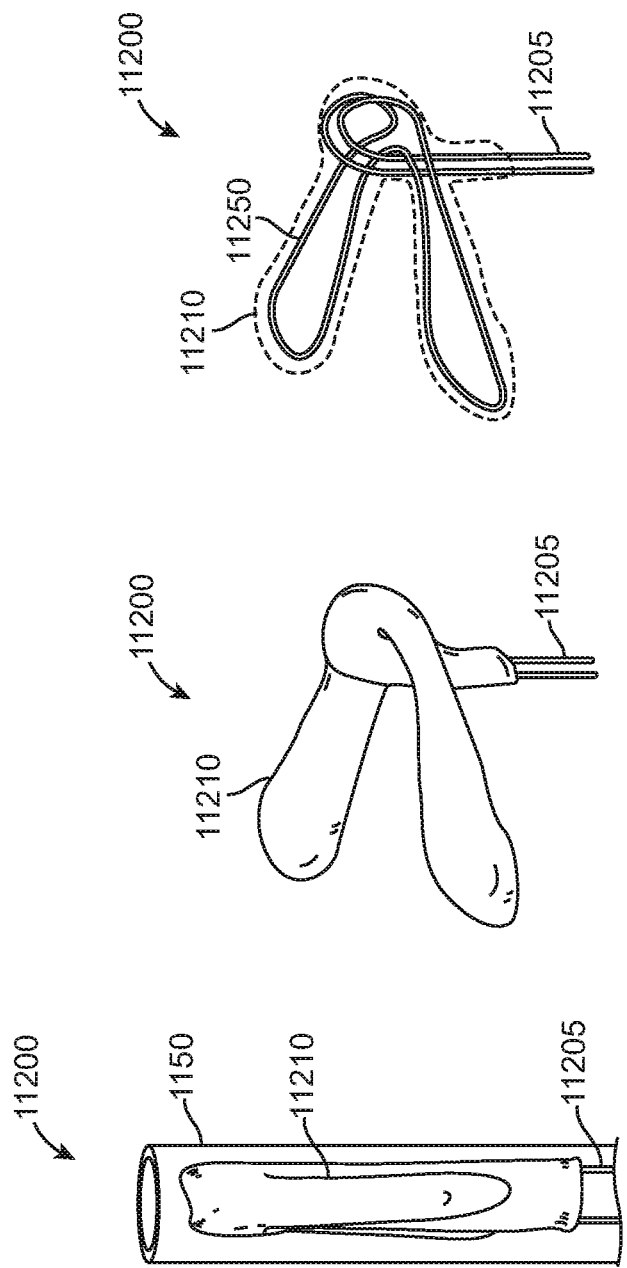

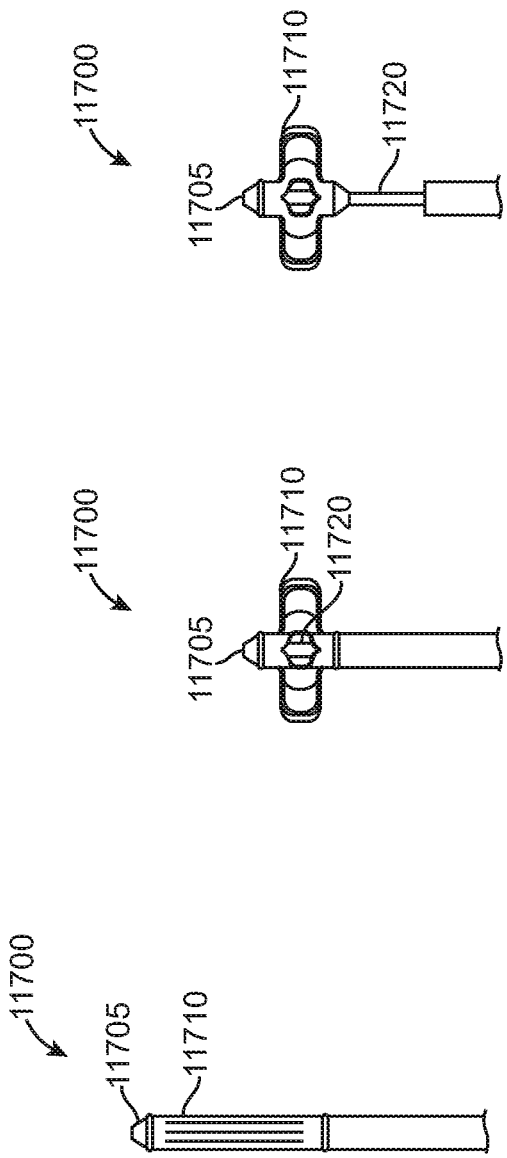

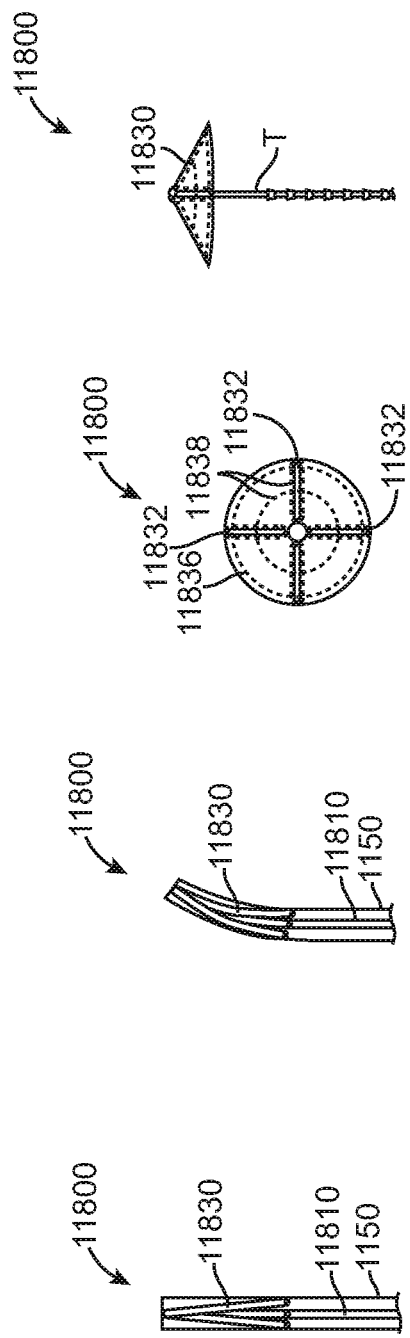

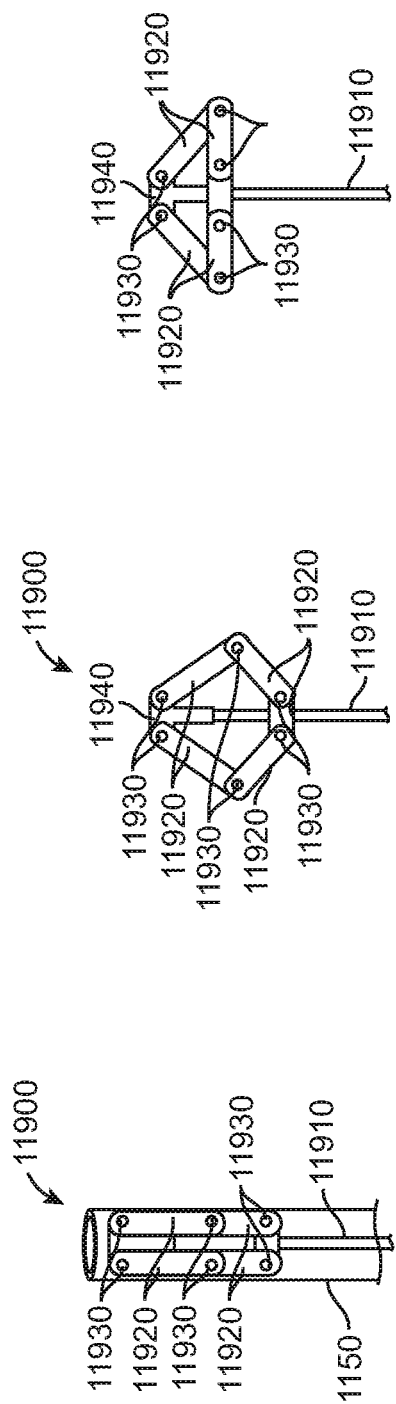

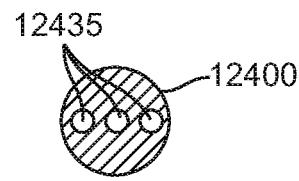
FIG. 124B
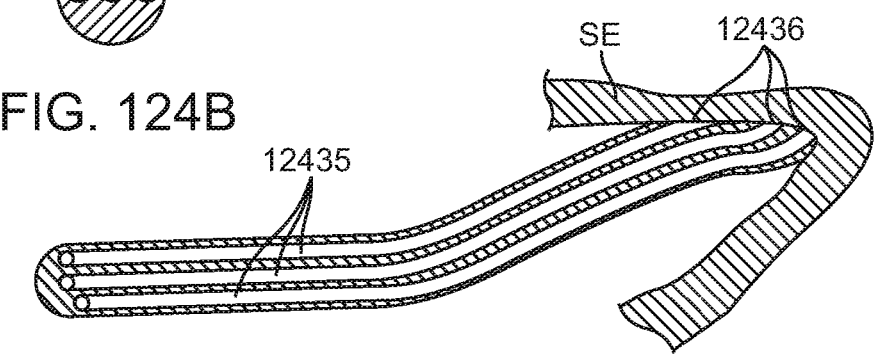
FIG. 124C
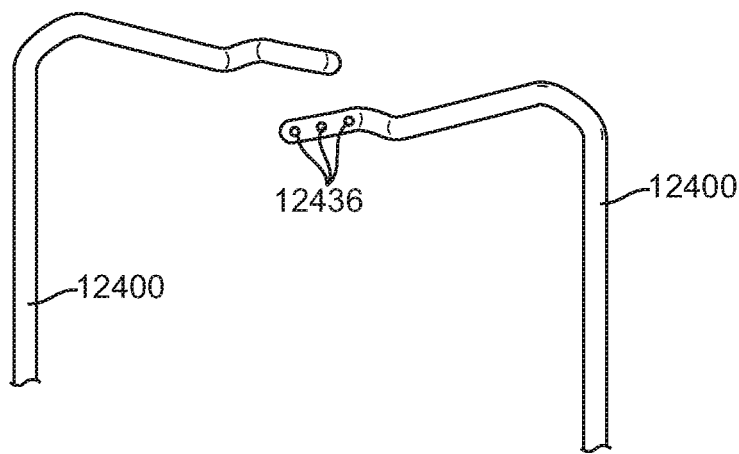
FIG. 124D
FIG. 124E

TREATING DYSFUNCTIONAL CARDIAC TISSUE

CROSS-REFERENCES TO RELATED APPLICATIONS

This application is a continuation of U.S. patent application Ser. No. 15/894,753 entitled "Treating Dysfunctional Cardiac Tissue," filed Feb. 12, 2018, now U.S. Pat. No. 10,624,744, which is a continuation of U.S. patent application Ser. No. 15/341,945 entitled "Treating Dysfunctional Cardiac Tissue," filed Nov. 2, 2016, now U.S. Pat. No. 9,889,008, which is a continuation of U.S. patent application Ser. No. 14/636,068 entitled "Treating Dysfunctional Cardiac Tissue," filed Mar. 2, 2015, now U.S. Pat. No. 9,486,206, which is a continuation of U.S. patent application Ser. No. 13/949,025 entitled "Treating Dysfunctional Cardiac Tissue," filed Jul. 23, 2013, now U.S. Pat. No. 8,968,175, which is a continuation of U.S. patent application Ser. No. 12/245,040 entitled "Treating Dysfunctional Cardiac Tissue," filed on Oct. 3, 2008, now U.S. Pat. No. 8,491,455, which claims the benefit of U.S. Provisional Patent Application No. 60/977,286 entitled "Method and Device for Treating Dysfunctional Cardiac Tissue," filed on Oct. 3, 2007; and to U.S. Provisional Patent Application No. 61/082,438, entitled "Cardiac Anchor Structures, Methods, and Systems for Treatment of Congestive Heart Failure and Other Conditions," filed on Jul. 21, 2008, the disclosures of which are hereby incorporated herein by reference.

BACKGROUND OF THE INVENTION

The present invention is related to improved medical devices, systems, and methods, with many embodiments being particularly useful for reducing the distance between two points in tissue in a minimally or less invasive manner. Specific reference is made to the treatment of a failing heart, particularly the alleviation of congestive heart failure and other progressive heart diseases. The provided devices, systems, and methods will often be used so as to resize or alter the geometry of a ventricle in a failing heart, such as by reducing its radius of curvature through the process of excluding a portion of the circumference from contact with blood, and thereby reduce wall stress on the heart and improve the heart's pumping performance. Some exemplary embodiments of the devices, systems, and methods of the present invention are directed toward catheter-based, thoracoscopic and/or subxiphoid techniques used to facilitate sizing of the ventricles. Although specific reference is made to the treatment of a failing heart, embodiments of the present invention can also be used in any application in which tissue geometry is altered.

Exemplary embodiments described herein provide implants and methods for alleviating congestive heart failure and other progressive diseases of the heart. Congestive heart failure may, for example, be treated using one or more implants which are selectively positioned relative to a first wall of the heart (typically an interventricular septum, hereafter known as the "septum"), and another wall of the heart so as to exclude scar tissue and limit a cross sectional area, or distance across a ventricle. Functional deterioration of the heart tissues may be inhibited by decreasing a size of the heart chamber and/or approximating tissues when stress on the tissues is limited. Implant locations and overall chamber remodeling achieved by placement of a series of implants may be determined so as to provide a beneficial volumetric decrease and chamber shape.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunction due to degenerative processes or other causes, cardiomyopathy (a primary disease of the heart muscle itself), congenital heart defects, infections of the heart tissues, and the like. However, in most cases congestive heart failure may be triggered by a heart attack or myocardial infarction. Heart attacks can cause scar tissue that interferes with the heart muscle's healthy function, and that scar tissue can progressively replace more and more of the contractile heart tissue. More specifically, the presence of the scar may lead to a compensatory neuro-hormonal response by the remaining, non-infarcted myocardium leading to progressive dysfunction and worsening failure.

People with heart failure may have difficulty exerting themselves, often becoming short of breath, tired, and the like. As blood flow out of the heart decreases, pressure within the heart increases. Not only does overall body fluid volume increase, but higher intracardiac pressure inhibits blood return to the heart through the vascular system. The increased overall volume and higher intracardiac pressures result in congestion in the tissues. Edema or swelling may occur in the legs and ankles, as well as other parts of the body. Fluid may also collect in the lungs, interfering with breathing (especially when lying down). Congestive heart failure may also be associated with a decrease in the ability of the kidneys to remove sodium and water, and the fluid buildup may be sufficient to cause substantial weight gain. With progression of the disease, this destructive sequence of events can cause the progressive deterioration and eventual failure of the remaining functional heart muscle.

Treatments for congestive heart failure may involve rest, dietary changes, and modified daily activities. Various drugs may also be used to alleviate detrimental effects of congestive heart failure, such as by dilating expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may involve (for example) surgical left ventricular reconstruction, ventricular restoration, the Dor procedure, and the like. If the heart becomes sufficiently damaged, even more drastic surgery may be considered. For example, a heart transplant may be the most viable option for some patients. These surgical therapies can be at least partially effective, but typically involve substantial patient risk. While people with mild or moderate congestive heart failure may benefit from these known techniques to alleviate the symptoms and/or slow the progression of the disease, less traumatic, and therefore, less risky therapies which significantly improve the heart function and extend life of congestive heart failure patients has remained a goal.

It has recently been proposed that an insert or implant be placed in the heart of patients with congestive heart failure so as to reduce ventricular volume. With congestive heart failure, the left ventricle often dilates or increases in size. This can result in a significant increase in wall tension and stress. With disease progression, the volume within the left ventricle gradually increases and blood flow gradually decreases, with scar tissue often taking up a greater and greater portion of the ventricle wall. By implanting a device which brings opposed walls of the ventricle into contact with one another, a portion of the ventricle may be excluded or closed off. By reducing the overall size of the ventricle, particularly by reducing the portion of the functioning ventricle chamber defined by scar tissue, the heart function may be significantly increased and the effects of disease progression at least temporarily reversed, halted, and/or slowed.

An exemplary method and implant for closing off a lower portion of a heart ventricle is described in U.S. Pat. No. 6,776,754, the full disclosure of which is incorporated herein by reference. A variety of alternative implant structures and methods have also been proposed for treatment of the heart. U.S. Pat. No. 6,059,715 is directed to a heart wall tension reduction apparatus. U.S. Pat. No. 6,162,168 also describes a heart wall tension reduction apparatus, while U.S. Pat. No. 6,125,852 describes minimally-invasive devices and methods for treatment of congestive heart failure, at least some of which involve reshaping an outer wall of the patient's heart so as to reduce the transverse dimension of the left ventricle. U.S. Pat. No. 6,616,684 describes endovascular splinting devices and methods, while U.S. Pat. No. 6,808,488 describes external stress reduction devices and methods that may create a heart wall shape change. Each of these patents is also incorporated herein by reference.

While the proposed implants may help surgically remedy the size of the ventricle as a treatment of congestive heart failure and appear to offer benefits for many patients, still further advances would be desirable. In general, it would be desirable to provide improved devices, systems, and methods for treatment of congestive heart failure. It would be particularly desirable if such devices and techniques could increase the overall therapeutic benefit for patients in which they are implanted, and/or could increase the number of patients who might benefit from these recently proposed therapies. Ideally, at least some embodiments would include structures and or methods for prophylactic use, potentially altogether avoiding some or all of the deleterious symptoms of congestive heart failure after a patient has a heart attack, but before foreseeable disease progression. It would be advantageous if these improvements could be provided without overly complicating the device implantation procedure or increasing the trauma to the patient undergoing the surgery, ideally limiting patient trauma while significantly enhancing the benefits provided by the implanted device.

BRIEF SUMMARY OF THE INVENTION

Embodiments of the present invention provide improved medical devices, systems, and methods, in many cases for reducing the distance between two points in tissue, optionally in a less or minimally invasive manner. The present invention may find specific use in the treatment of a failing heart, particularly the alleviation of congestive heart failure and other progressive heart diseases by reconfiguring abnormal heart geometry that may be contributing to heart dysfunction. In many embodiments, an anchor is inserted through first and second walls of the heart. An arm of the anchor is deployed and rotationally positioned according to a desired contour. Application of tension to the anchor may draw the first and second walls of the heart into linear contact along the desired contour. Additional anchors may be inserted to draw the first and second walls of the heart further into contact. By drawing the first and second walls of the heart into contact, a dysfunctional portion of the heart may be closed off along the contour such that the overall size of a ventricle is reduced and a more beneficial heart geometry is provided. Heart function may be significantly increased and the effects of disease progression may be at least temporarily reversed, halted, and/or slowed, with the implanted anchors optionally being deployed using catheter-based systems and methods.

In a first aspect, the invention provides a method for treating a heart of a patient. The heart has a chamber bordered by a plurality of walls. A first anchor is inserted along an insertion path through a first wall of the heart. An arm of the first anchor is laterally deployed. The arm of the first anchor is rotationally positioned about the insertion path per a desired contour. First and second walls of the heart are drawn into contact along the desired contour by applying tension to the first anchor through the insertion path.

In many embodiments, second and third anchors may be inserted through the first wall of the tissue along associated insertion paths. The arms of the second and third anchors are laterally deployed. The arms of the second and third anchors are rotationally positioned so that applying tension to the second and third anchors through their associated insertion paths extends the contact along the desired contour. The desired contour often curves laterally across the first wall.

In some embodiments, a second anchor is inserted through a third wall of tissue along an associated insertion path. An arm of the second anchor is laterally deployed. The arm of the second anchor is rotationally positioned so that applying tension to the second anchor through the associated insertion path extends the contact along the desired contour. Hence, the desired contour extends contiguously from the first wall to the third wall, such as from the septum to an outer wall of the heart.

In many embodiments, a tension member extends along the path from the inserted first anchor. The arm of the first anchor is rotationally positioned by rotating the anchor with the tension member or a tubular body over the tension member. An axis of the arm of the first anchor may extend along an elongate length from a central region adjacent the tension member to an end. Another arm of the first anchor may extend along an elongate length from the central region to another end so that the central region is between the ends, the arms optionally being defined by an integral arm structure extending the length of both arms. Tensioning of the tension member optionally forms a fold in the tissue along the desired contour.

In another aspect, embodiments of the invention provide a method for treating a heart of a patient. The heart has a chamber bordered by a plurality of walls. A first anchor is inserted along an insertion path extending through a first wall of the heart. An elongate arm of the first anchor is flexed in a first orientation during the insertion of the first anchor so as to accommodate a bend in the path. The arm of the first anchor is laterally deployed. First and second walls of the heart are drawn into contact by applying tension to the first anchor through the insertion path along a second orientation. The arm has a greater stiffness in the second orientation than in the first orientation so as to inhibit deflection of the arm away from the first wall when such tension is applied.

Optionally, the bend in the path is defined by a bent flexible catheter body. Preferably the stiffness of the arm in the second orientation is sufficient to induce contiguous contact of the walls along a contour between the first anchor and a second anchor when arms of the anchors are aligned along the contour. In contrast, the stiffness of the arm in the first orientation need not be sufficient to ensure contiguous contact of the walls between the anchors.

In another aspect, the invention provides a system for treating a heart of a patient. The system comprises an introducer having a proximal end and a distal end with a shaft therebetween. The distal end is insertable along an insertion path through first and second heart walls bordering a chamber of the heart. A first anchor is axially translatable along the path of the introducer through the heart walls. An elongate member is extendable proximally from the first anchor and rotationally coupled to the first anchor so as to axially rotate the first anchor from proximally of the heart walls. This allows a system user to orient an arm of the anchor along a desired lateral orientation from the insertion path.

Preferably, the first anchor comprises an arm structure pivotally coupled to the elongate member so as to pivot from an insertion configuration to a deployed configuration. The arm structure in the deployed configuration may define first and second arms extendable from the elongate member along a desired contour, for example, with the first arm extending along the first orientation and the second arm extending opposite the first orientation. The first and second arms may comprise integral portions of the arm structure, and the arm structure in the insertion configuration may extend along an axis of the elongate member with the first arm extending proximally and the second arm extending distally, or the like. The elongate member typically comprises a tension member extending proximally from an elongate shaft of the first anchor, the elongate shaft pivotally coupled to the arm structure. The elongate member typically comprises a tension member such as a tether having a plurality of axially repeating features, each of the repeating features comprising at least one of a protrusion, bard, or pawl. In some embodiments, the arm structure is connected to the elongate member through a flexible joint.

The system will often include a second or proximal anchor, the second anchor comprises a locking mechanism operatively engageable with the tension member so as to allow axial movement of the anchors toward each other, and so as to inhibit axial movement of the anchors away from each other. The system may include multiple anchor sets, such as by having a second anchor and a third anchor, each anchor having an associated elongate member tensionable so as to compress the walls together between the anchor and an associated proximal anchor.

In another aspect, the present invention provides a method for treating a heart of a patient. The method comprises advancing a distal tip of a catheter into a first ventricle of the heart and making a first perforation through a septal wall. The distal tip of the catheter is advanced through the first perforation into a second ventricle, and a second perforation is made through the wall of the second ventricle. The distal tip of the catheter advances through the second perforation into an epicardial space. An anchor is inserted distally of the wall of the second ventricle through a lumen of the catheter, and an arm of the anchor is deployed laterally. The arm is rotated relative to an axis of the catheter so that the arm extends along a desired contour, and tension is applied along the insertion path to the anchor so as to urge the wall of the second ventricle proximally against the septal wall along the contour.

Optionally, the distal tip of the catheter can be curved by a catheter bending mechanism when the making the first perforation, so that the catheter within the first ventrical bends away from the septum and back toward the septum, and/or so that the distal tip faces the septum prior to making the first perforation on the septum. An exemplary bending mechanism pivotally couples an end of the catheter to a catheter body portion proximal of the end using a director. A third perforation can be made on the on the septal wall adjacent to the first perforation on the septal wall, a fourth perforation on the wall of the second ventricle can be made adjacent to the second perforation on the wall of the second ventricle, and so on. A second anchor can be inserted distally of the wall of the second ventricle through the third and fourth perforations and deployed laterally along a contour extending between the anchors. By applying tension along the second insertion path to the second anchor, the wall of the second ventricle can be urged proximally against the septal wall along the contour. The distal tip of the catheter can be stabilized relative to the septal wall and/or wall of the second ventrical by applying suction through a suction lumen of the catheter.

In another aspect, the invention provides a system for treating a heart of a patient, the heart having a chamber bordered by a plurality of walls. The system comprises a tubular body having a lumen extending along an axis to a distal end, the tubular body accommodating a bend in the axis. A first anchor is extendable through a first wall of the heart within the lumen, the first anchor having an elongate arm deployable from an insertion configuration suitable for insertion of the first anchor within the lumen to a deployed configuration, the elongate arm having a first stiffness in a first orientation so as to accommodate the bend in the tubular body, the arm having a second stiffness in a second orientation, the second stiffness greater than the first orientation so as to inhibit deflection of the arm away from the wall when the arm is deployed distally of a wall of the heart and proximal tension is applied to the arm to pull the heart wall proximally.

In yet another aspect, the invention provides an assembly for treating a heart of a patient. The assembly comprises at least two elongate tension members, and at least two distal anchor assemblies. Each distal anchor assembly comprises an elongate arm deployable laterally from the tension member after insertion distally through a heart wall, and each distal anchor assembly is coupleable to the distal end of an associate tension member so as draw the anchors and a wall of the heart proximally. A proximal anchor arm system has at least two apertures adapted to be advanced distally over the tension members and to inhibit proximal movement of the proximal anchor relative to the tension members while engaging the heart throughout a contour extending between the tension members.

Optionally, the proximal anchor arm system comprises a first proximal anchor arm having a first adhesive region and an aperture adapted to be advanced and secured over a first of the tension members. A second proximal anchor arm similarly has a second adhesive region and an aperture adapted to be advanced and secured over a second tension member. The first adhesive region of the first proximal anchor and the second adhesive region of the second proximal anchor may adhere to each other when in contact.

In additional aspects, the invention provides anchor assemblies for treating a heart of a patient. The assemblies may comprise an expandable member coupled to a distal end of an elongate shaft. The expandable member may include a wire which can resiliently expand into a deployed, expanded form, such as a superelastic Nitinol™ shape memory alloy or the like. In another exemplary anchor assembly the expandable member comprises a plurality of segments coupled to each other by articulated hinges, the plurality of segments having a low profile, undeployed configuration and a high profile, deployed configuration.

In yet another aspect, the invention provides tether cutting devices comprising a first elongate shaft having a proximal end, a distal end, and a central lumen. The shaft may comprise a flexible catheter shaft. In some embodiments, at least one cutting member extends outward from the distal end of the first elongate shaft, the at least one cutting member having an inwardly facing cutting edge. A second elongate shaft has a proximal end and a distal end, and is axially translatable over the first elongate shaft. The distal end of the second elongate shaft pushes the at least one cutting member inward to cut a tether passed through the lumen of the first elongate shaft as the second elongate shaft is advanced distally. In alternative embodiments, a distal cap is axially translatable over the distal end of an elongate shaft, the distal cap having an aperture and comprising at least one blade facing inward and disposed on an interior side of the distal cap. The at least one elongate arm of the elongate shaft pushes the at least one cutting member inward to cut a tether passed through the lumen of the elongate shaft as the distal cap is retracted proximally. In still other embodiments, proximal retraction of at least one elongate member pulls at least one cutting member inward to cut a tether passed through the distal aperture and central lumen of the elongate tubular shaft, or the like.

BRIEF DESCRIPTION OF THE DRAWINGS

FIG. 6 shows a dilation system;
FIG. 7 shows a cross-section of the dilation system of FIG. 6;
FIG. 8 is a magnified view of the distal end of the dilation system of FIG. 6 with a balloon of the distal end in an unexpanded configuration;
FIG. 9 is a magnified view of the distal end of the dilation system of FIG. 6 with the balloon of the distal end in an expanded configuration;
FIG. 11 shows an exemplary anchor assembly;
FIGS. 11a-11c show the distal end of the anchor device of FIG. 11;
FIG. 11a shows the anchor device in a deployed configuration;
FIG. 11b shows a cutaway view of the anchor device in a deployed configuration;
FIG. 11c shows a cutaway view of the anchor device in an undeployed configuration.
FIGS. 12a-12c show an introducer catheter having an anchor device placed therein;
FIG. 12a shows the introducer catheter having the anchor device disposed therein;
FIG. 12b shows a cutaway view of the introducer catheter;
FIG. 12c shows the introducer catheter with the anchor device more distally advanced;
FIGS. 46A-52B show the distal ends of anchor devices according to embodiments of the invention;
FIGS. 54a-54d show an anchor with a retract tether according to embodiments of the invention;
FIGS. 67-93 show a method of reducing the distance between opposed walls of a heart using a catheter-based system according to embodiments of the invention;
FIGS. 94-110 show proximal or external anchor assemblies according to embodiments of the invention;
FIGS. 111-119C show the leading ends of anchor devices according to embodiments of the invention;
FIGS. 124A-124E show an exemplary second catheter sheath according to embodiments of the invention.

DETAILED DESCRIPTION OF THE INVENTION

The present invention generally provides improved devices, systems, and methods for treatment of a heart. Embodiments of the invention may be particularly beneficial for treatment of congestive heart failure and other disease conditions of the heart. The invention may find uses as a prophylactic treatment, and/or may be included as at least a portion of a therapeutic intervention.

Embodiments of the invention may find use as a device applied to or implant placed in the heart of certain patients with congestive heart failure so as to reduce ventricular volume in a procedure called "Epicardial Catheter-based Ventricular Reconstruction," or ECVR. The left ventricle of hearts affected with congestive heart failure may dilate or increase in size. This increase in size can result in a significant increase in wall tension and stress. With disease progression, the volume of the left ventricle gradually increases while forward blood flow gradually decreases. Scar tissue will often take up a greater and greater percentage of the ventricle wall and non-scarred, viable muscle will often dilate as a result of increased strain. By implanting a device which brings opposed walls of the ventricle into contact with one another, a portion of the ventricle, usually the dysfunctional portion, may be constricted or closed off, thereby reducing volume. By reducing the overall size of the ventricle, particularly by reducing the portion of the functioning ventricle chamber formed by scar tissue, the heart function may be significantly increased and the effects of disease progression may be at least temporarily reversed, halted, and/or slowed.

Figure 1:
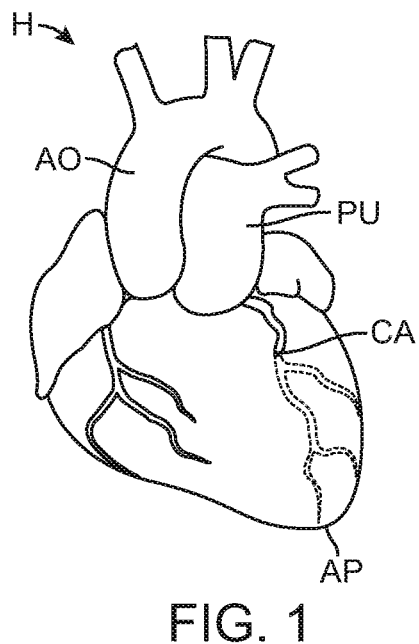
FIG. 1 is a front view of a healthy heart.
Figure 2:
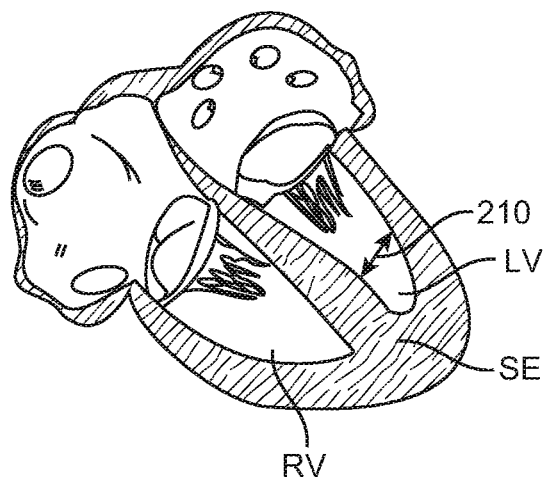
FIG. 2 is a cross-sectional view of the heart of FIG. 1.

FIG. 1 shows a normal heart H and FIG. 2 shows the cross-section of normal heart H. Normal heart H includes structures such as the aorta AO, pulmonary artery PU, coronary artery CA, apex AP, right ventricle RV, left ventricle LV with a radius 210, and septum SE.

Figure 3:
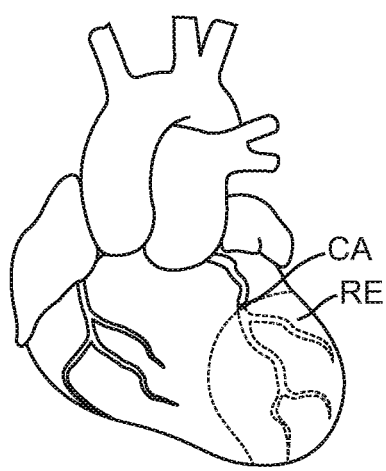
FIG. 3 is a frontal view of a heart having infarcted tissue.
Figure 4:
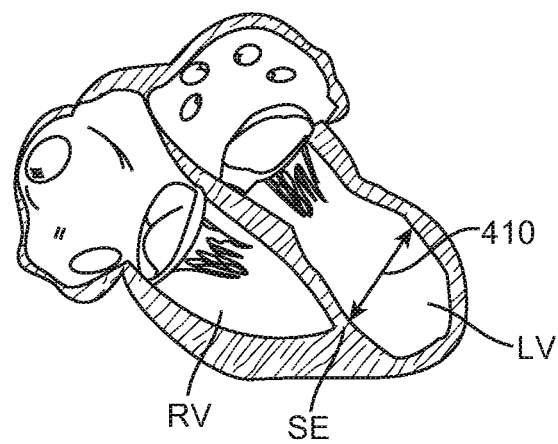
FIG. 4 is a cross-sectional view of the heart of FIG. 3.

Myocardial infarction and the resultant scar formation is often the index event in the genesis of congestive heart failure ("CHF"). The presence of the scar, if left untreated, may lead to a compensatory neuro-hormonal response by the remaining, non-infarcted myocardium. FIG. 3 shows a region RE (bordered by a dotted line) of left ventricle LV which includes scar tissue. With congestive heart failure, the left ventricle often dilates or increases in size as shown in FIG. 4, in which radius 210 has increased to a radius 410. This increase in size can result in a significant increase in wall tension and stress. With disease progression, the volume of the left ventricle LV gradually increases while forward blood flow gradually decreases, with scar tissue expanding while unscarred muscle dilates and becomes thin, losing contractility. The systems, methods, and devices described herein may be applied to inhibit, reverse, or avoid this response altogether, often halting the destructive sequence of events which could otherwise cause the eventual failure of the remaining functional heart muscle.

CHF is a condition in which the heart does not pump enough blood to the body's other organs. CHF may result from narrowing of the arteries that supply blood to the heart muscle, for instance, the coronary artery CA as shown in FIGS. 1 and 3. Other causes of CHF include high blood pressure, heart valve dysfunctions due to degenerative processes or other causes, cardiomyopathy (a disease of the heart muscle itself), congenital heart defects, infections of the heart tissues, and the like. In certain pathological conditions, the ventricles of the heart can become ineffective in pumping the blood, causing a back-up of pressure in the vascular system behind the ventricle. The reduced effectiveness of the heart may be due to an enlargement of the heart. For example, the left ventricular radius 210 of a heart H, as shown in FIGS. 1 and 2, may eventually increase to a larger left ventricular radius 410 of a failing heart H, as shown in FIGS. 3 and 4.

Acute myocardial infarction (AMI) due to obstruction of a coronary artery CA is a common initiating event that can lead ultimately to heart failure. A myocardial ischemia may cause a portion of a myocardium of the heart to lose its ability to contract. Prolonged ischemia can lead to infarction of a portion of the myocardium (heart muscle). Once this tissue dies, it no longer acts as a muscle and cannot contribute to the pumping action of the heart. When the heart tissue is no longer pumping effectively, that portion of the myocardium is said to be hypokinetic or akinetic, meaning that it is less contractile or acontractile relative to the uncompromised myocardial tissue. As this situation worsens, the local area of compromised myocardium may bulge out as the heart contracts, further decreasing the hearts ability to move blood forward and dilating a ventricle. This bulged out myocardium can be seen in region RE as shown bordered by a dotted line in FIG. 3.

As shown in FIGS. 3 and 4, one problem with a large dilated left ventricle is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilation is greater than the hypertrophy and the result is a rising wall tension requirement for systolic contraction. This rising wall tension requirement may be an ongoing insult to the muscle myocytes (heart muscle cells), resulting in further muscle damage. In response, the heart tissue often remodels to accommodate the chronically increased filling pressures, further increasing the work that the now-compromised myocardium must perform. This vicious cycle of cardiac failure may result in the symptoms of CHF such as shortness of breath on exertion, edema in the periphery, nocturnal dyspnea (a characteristic shortness of breath that occurs at night after going to bed), weight gain, and fatigue, to name a few. The increase in wall stress also occurs during throughout the cardiac cycle and inhibits diastolic filling. The stress increase requires a larger amount of oxygen supply, which can result in exhaustion of the myocardium leading to a reduced cardiac output of the heart.

Embodiments of the present invention may build on known techniques for exclusion of the scar and volume reduction of the ventricle. Unlike known techniques that are often accomplished through open surgery, including left ventricular reconstruction, ventricular restoration, the Dor procedure, and the like, the treatments described herein will often (though not necessarily always) be implemented in a minimally invasive or less invasive manner. Embodiments of the invention can provide advantages similar to those (for example) of surgical reconstruction of the ventricle, resulting in improved function due to improved dynamics, and by normalizing the downward cycle initiated by the original injury and mediated by the neuro-hormonal disease progression response.

Advantageously, the methods, devices, and systems described herein may allow percutaneous left ventricular scar exclusion and ventricle volume reduction to be applied at any appropriate time during the course of the disease. Rather than merely awaiting foreseeable disease progression and attempting to alleviate existing cardiac dysfunction, the techniques described herein may be applied proactively to prevent some or all of the heart failure symptoms, as well as to reverse at least a portion of any existing congestive heart failure effects, to limit or halt the progression of congestive heart failure, and/or to retard or prevent congestive heart failure disease progression in the future. Some embodiments may, for appropriate patients, limit the impact of myocardial infarction scar formation before heart failure even develops.

Figure 5:
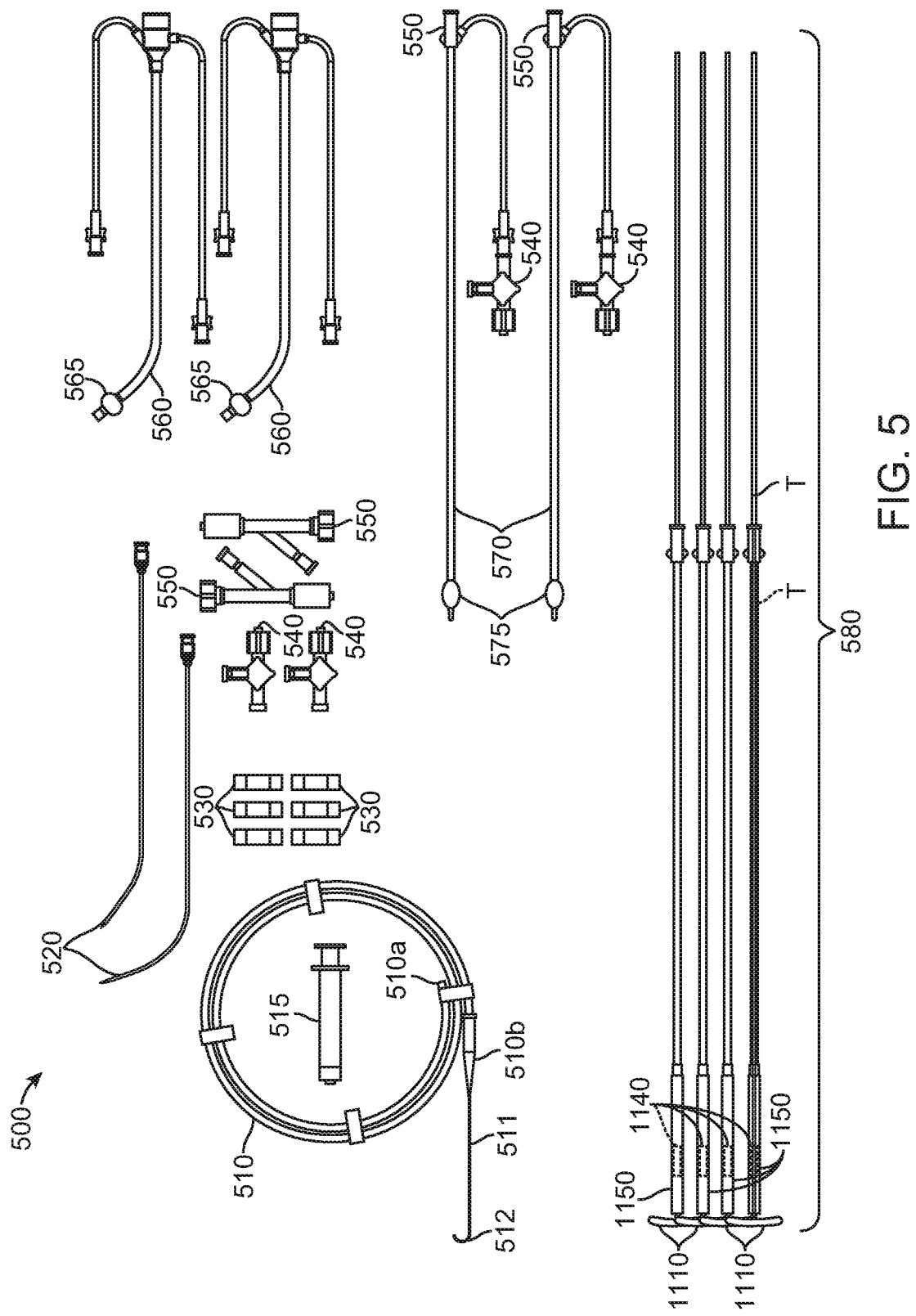
FIG. 5 shows a system according to embodiments of the invention for treating congestive heart failure.

Referring now to FIG. 5, embodiments of the present invention may comprise a system 500 for treating congestive heart failure. System 500 may comprise a catheter 510, a guidewire 511, a syringe 515, bent insertion needles or guidewire introducers 520, external anchor arms 530, stopcocks 540, Toughy-Borst adapters 550, balloon introducers or introducer catheters 560, dilation systems or balloon dilators 570, and/or anchor assemblies 580. Catheter 510 will typically comprise an elongate flexible catheter body having a proximal end 510a, a distal end 510b, and a central lumen therebetween. The lumen of catheter 510 can receive guidewire 511 so that the catheter can be advanced over guidewire 511. In some embodiments, the distal or leading end of catheter 510 may comprise a curved end 512. Curved end 512 may be integral to guidewire 511 or may be a separate element attachable to guidewire 511, with the guidewire optionally being suitable for use in J-wire access techniques within the heart. Syringe 515 may be adapted to couple to catheter 510 and infuse catheter 510 with a fluid, for example, saline and/or a high-contrast imaging fluid, when catheter 510 is positioned within a patient's body.

Figure 5A:
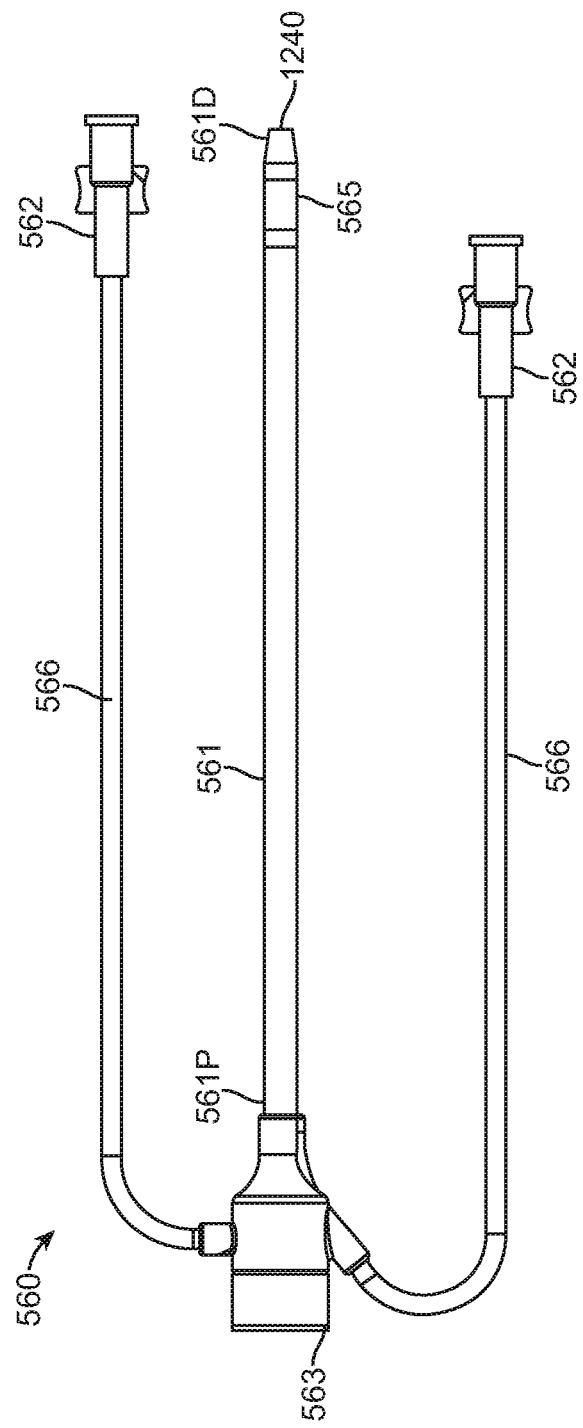
FIG. 5A shows a magnified view of introducer catheter.

Referring now to FIGS. 5 and 5A, introducer catheter 560 may comprise an elongate catheter body 561 having a proximal end 561P, a distal end 561D, a proximal adapter 562, and an expandable member 565 disposed on the distal or leading end 561D. Introducer catheter 560 can have a central lumen 1240 and the inner diameter of introducer catheter 560 can be greater than the outer diameter of a balloon dilator 570 when its balloon is deflated such that the balloon dilator 570 can fit within the lumen of introducer catheter 560. Balloon dilator 570 may comprise a stopcock 540, a Toughy-Borst adapter or valved adapter 550, and a expandable element or balloon 575 disposed on its distal or leading end.

Referring now to FIGS. 5 and 11-11c, each anchor assembly 580 may comprise a tensile member or tether T and a distal or leading end anchor 1110. Distal or leading end anchor 1110 may comprise anchor arms extendable laterally from the tether is opposed directions, with the exemplary arms being formed as a single elongate arm body or structure of any medical grade metal or other material, for example, medical grade titanium. Tensile member or tether T may comprise any biocompatible polymer, metal, or other material, for example, metals such as stainless or nitinol, polyether ether ketone (PEEK), and/or the like. The tether T may have a length sufficient to extend proximally out of the patient when the anchor is implanted, with the tether optionally being formed by cutting sheet polymer material in a spiral so that the tether is biased to form a proximal pigtail. External anchor arm 530 and anchor assembly 580 may be covered by knotted or woven polyester cloth. Anchor assembly 580 may further comprise a plug 1140, and a sheath 1150. Plug 1140 may comprise chemical or cellular components which facilitate clotting, fibrosis, ingrowth and/or other desirable processes, such as a polyester or Teflon felt or the like. Similarly, a layer of such materials may cover some or all of the anchor to promote ingrowth, hemostasis, or the like, optionally by sewing a woven, knit, and/or felt polyester cloth over the anchor. The tether T, anchor 1110, and (if it is included) plug 1140 may be contained in a lumen of a delivery catheter 1240.

FIG. 5A shows a magnified view of introducer catheter 560. Expandable member 565 is disposed on the distal or leading end of introducer catheter 560. Introducer catheter 560 comprises valves 562, each coupled to hub 563 through tubings 566. Valves 562 may be used to control fluid introduction into the lumen of introducer catheter 560 or to control fluid introduction and removal to either expand or contract expandable member 565.

A magnified view of balloon dilator 570 is shown in FIG. 6. The distal or leading end tip 610 of balloon dilator 570 is tapered. FIG. 8 shows a magnified view of tapered distal tip 610. As shown in FIG. 8, tapered distal tip 610 may have a first diameter 810 and a greater, second diameter 820 at a location proximal to first diameter 810. FIG. 7 shows a cross-section of balloon dilator 570, which comprises a central lumen 710 and a balloon inflation lumen 720. Central lumen 710 can extend from an opening in distal tip 610 to the proximal or trailing end of balloon dilator 570 and may extend into Toughy-Borst adapter 550 and/or stopcock 540.

Balloon inflation lumen 720 may extend from the proximal or trailing end of balloon dilator 570 to balloon inflation exit port 722 which is disposed towards the wider end of tapered distal tip 610. A fluid, for example, saline, may be passed through balloon inflation lumen 720 and balloon inflation lumen port 722 to fill or expand balloon 575. Fluid may also be drained from an expanded balloon 575 through balloon inflation port 722 and balloon inflation lumen 720. FIG. 8 shows balloon 575 in an unexpanded form while FIG. 9 shows balloon 575 in an expanded form.

Figures 10, 10A:
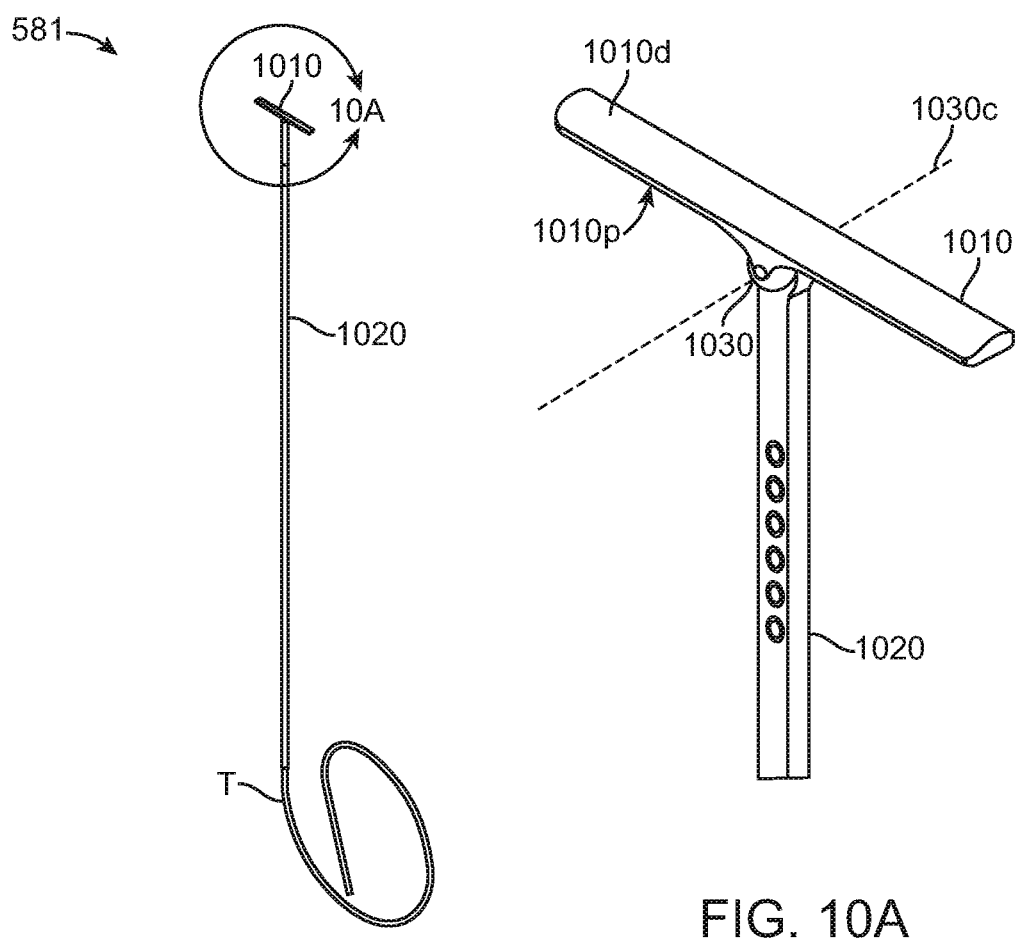
FIGS. 10 and 10A show components of an exemplary anchor assembly.
Figure 10B:
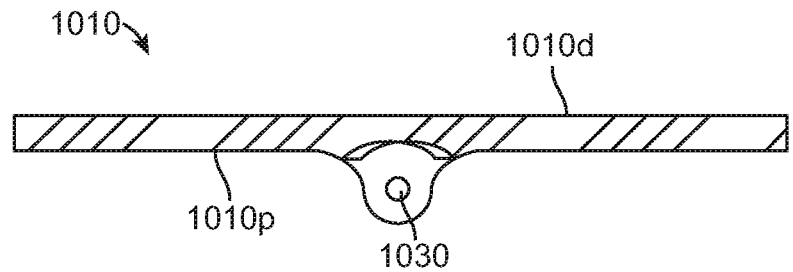
FIG. 10B shows a side view of the anchor assembly of FIG. 10.
Figure 10C:
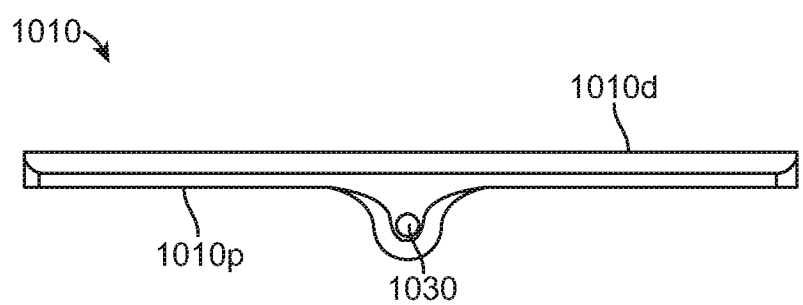
FIG. 10C shows a side cross-sectional view of the anchor assembly of FIG. 10.
Figure 10D:
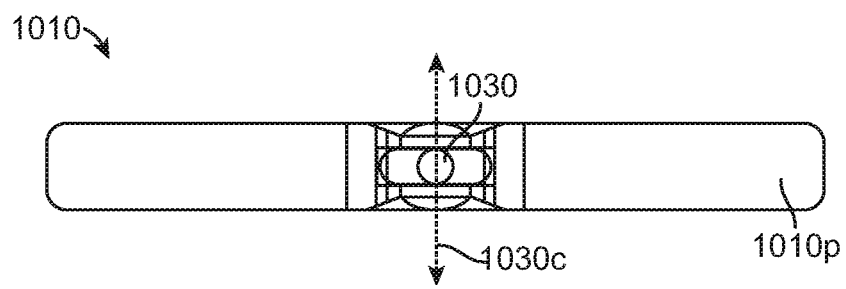
FIG. 10D shows a bottom view of the anchor assembly of FIG. 10.
Figure 10E:
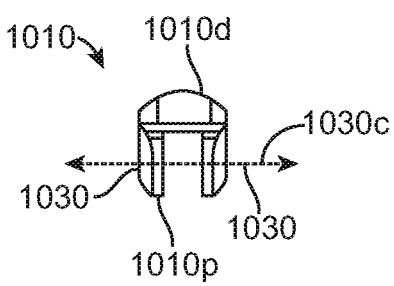
FIG. 10E shows cross-section of the anchor assembly of FIG. 10.

FIG. 10 shows an exemplary anchor assembly 581. Anchor assembly 581 may be generally similar to anchor assembly 580 and may be used in lieu of anchor assembly 580 for many of the methods and systems described herein. Anchor assembly 581 comprises a leading or distal anchor arm body 1010. In a deployed form of anchor assembly 581, anchor arm 1010 may be generally or roughly perpendicular to elongate member 1020 which is coupled to tether T or the arm may extend across the tether at some oblique angle. Anchor arm 1010 is coupled to elongate member 1020 through joint or hinge 1030. Anchor arm 1010 comprises a distal surface 1010d and a proximal surface 1010p. In use, anchor arm 1010 is often oriented so that proximal surface 1010p engages with a tissue surface. Anchor arm 1010 can rotate about axis 1030c which is centered on hinge 1030. Anchor arm 1010 may rotate about axis 1030c by at least about 90° so as to facilitate loading the anchor and tether into a delivery catheter. The anchor arm may be at least partially covered by (such as being largely or entirely encased within) a material that promotes tissue ingrowth, such as a woven or felt polyester.

FIG. 11 shows an anchor assembly 580. FIGS. 11a, 11b, and 11c show the distal or leading end of an anchor assembly 580 and its delivery catheter 1111 with distal sheath 1150. FIG. 11a shows the distal end of anchor assembly 580 in a deployed form. FIG. 11b shows the distal end of anchor assembly 580 in a deployed form. FIG. 11c shows the distal end of anchor assembly 580 in an undeployed form. The distal end of anchor assembly 580 comprises a distal anchor arm 1110, an elongate member 1120, tether T, and a plug 1140. Tether T may comprise a plurality of repeating features, for example, protrusions, barbs, or pawls 1130. In alternative embodiments, tether T may have a slide surface 1177 without such macroscopic ratchet elements, and which is engageable by a one-way slide/locking mechanism as described below. Distal anchor arm 1110 is connected to elongate member 1120 through a joint 1160, which may comprise a living hinge of flexible, resilient material such that distal anchor arm 1110 can be constrained to be generally parallel to elongate member 1120. In the undeployed form of anchor assembly 580 as seen in FIG. 11c, distal anchor arm 1110 can be oriented in relation to elongate member 1120 such that distal anchor arm 1110 is able to fit within sheath 1150 of delivery catheter 1111. Moving elongate member 1120 distally or retracting sheath 1150 proximally can cause distal arm 1110 to move out of the constraint of sheath 1150 so that anchor assembly 580 is laterally deployed. In the deployed form, distal anchor arm 1110 can be generally perpendicular or oblique to elongate member 1120 and sheath 1150 of delivery catheter 1111 or may otherwise be generally oriented so as to extend laterally from the tether in a position relative to elongate member 1120 and sheath 1150 such that it cannot be retracted into sheath 1150 and/or pulled proximally through a tissue wall through which the delivery catheter and tether extend.

FIGS. 12a, 12b, and 12c show an anchor assembly 580 within the adapter 562 of introducer catheter 560. FIG. 12a shows adapter 562, the proximal or trailing end of introducer catheter 560, and an anchor assembly 580 disposed partially within. FIG. 12b shows a cross-section of adapter 562. FIG. 12c shows a cross-section of adapter 562 with anchor assembly 580 advanced further distally than in FIG. 12b. Adapter 562 includes a proximal expandable member inflation port 1210 and a center lumen infusion port 1230. Proximal expandable member inflation port 1210 is coupled to expansion element inflation lumen 1220. Introduction and removal of fluid through port 1210 and lumen 1220 can respectively expand or contract expansion element 565. Center lumen infusion port 1230 is coupled to center lumen 1240 of introducer catheter 560. Fluid may be introduced to center lumen 1240 through port 1240 to infuse center lumen 1240.

Figure 13:
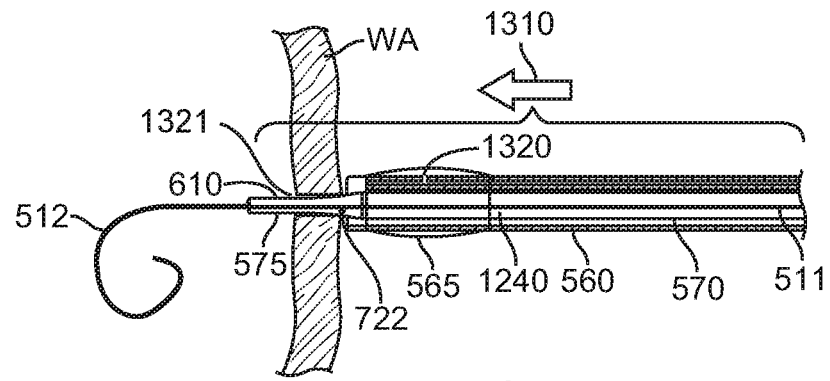
FIGS. 13-24 show a method of reducing the distance between two points in tissue wall according to embodiments of the invention.
Figure 14:
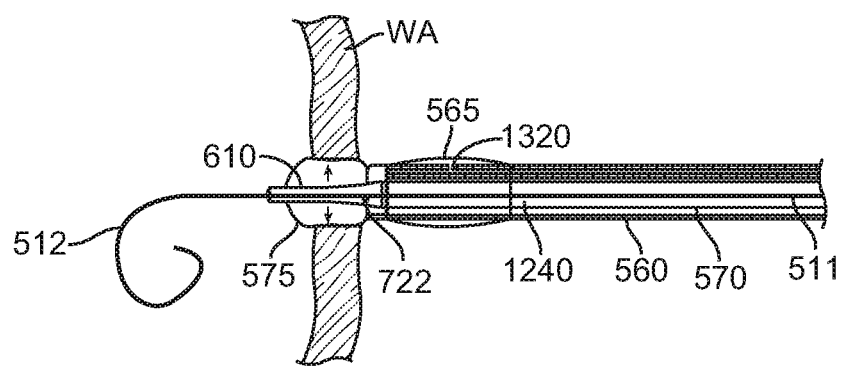
Figure 14A:
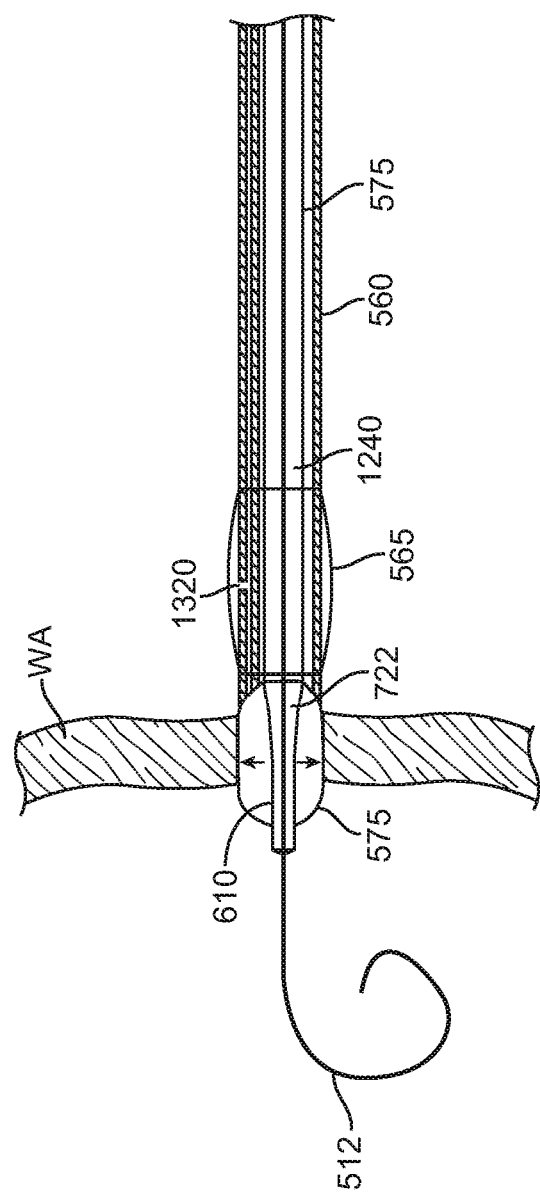

FIGS. 13-24 show a method of using system 500 to reduce the distance between two points in tissue wall. FIG. 13 shows introducer catheter 560 with balloon dilator 570 advanced over guidewire 511. Introducer catheter 560 and balloon dilator 570 are distally advanced together through a perforation 1321 in tissue wall WA in a direction indicated by distally pointed arrow 1310. The sides of tissue wall WA are in contact with balloon 575. As shown in FIG. 14, balloon 575 is expanded. As shown in FIG. 14a, the outer diameter of expanded balloon 575 may be at least as large as (and optionally being larger than) the outer diameter of introducer catheter 560 and unexpanded expansion member 565. For example, expanded balloon 575 may have a geometry such that, when expanded, an outer diameter of balloon 575 and the distal end of the tubular structure at the distal end of balloon introducer 560 tapers smoothly and radially inwardly as the surrounding tissue wall is pushed proximally from over balloon 575 onto balloon introducer 560. An inner chamfer along the lumen at the distal end of balloon introducer 560 matching the engaged slope at the proximal end of balloon 575 may help avoid discontinuities and facilitate distal advancement of the system through the heart wall.

Figure 15:
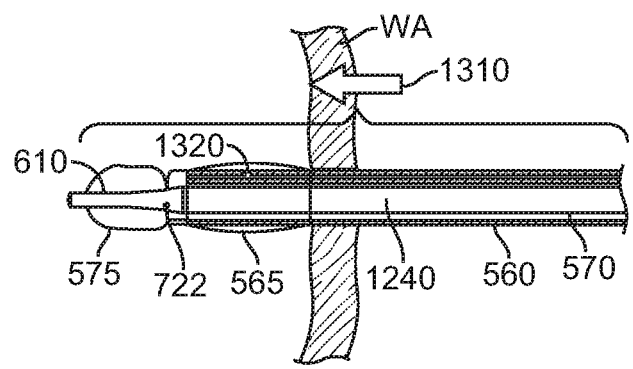
Figure 16:
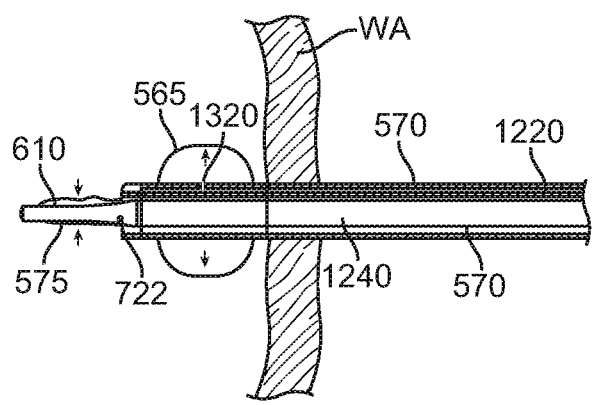
Figure 17:
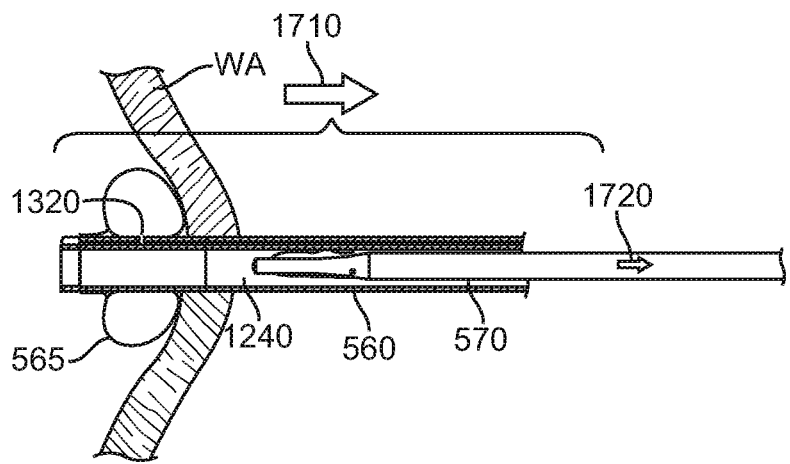
Figure 18:
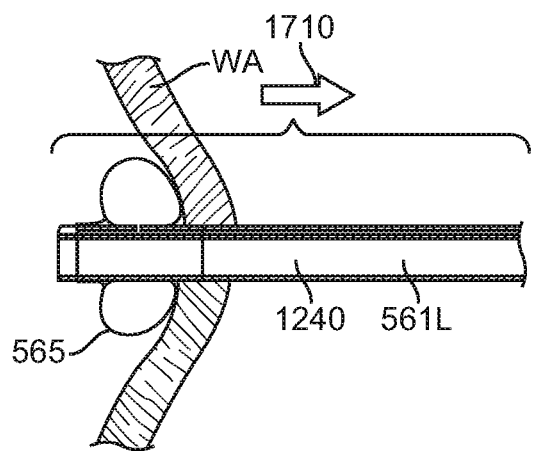
Figure 19:
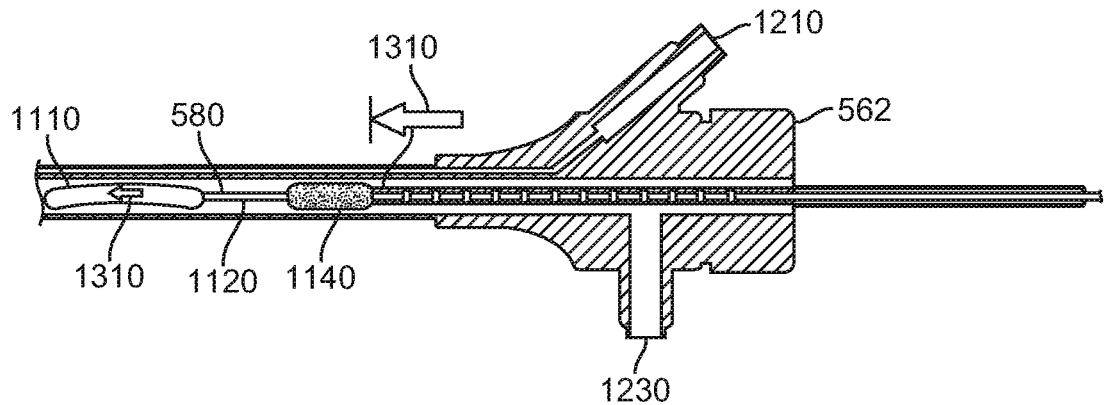
Figure 20:
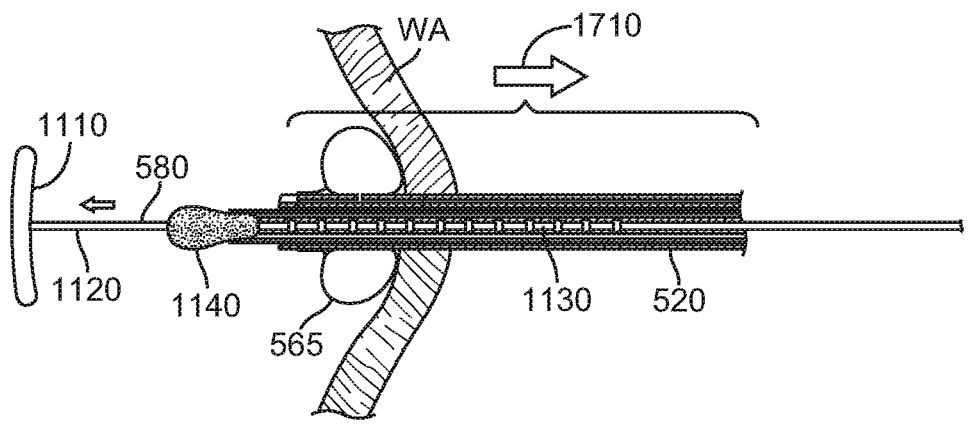
Figure 21:
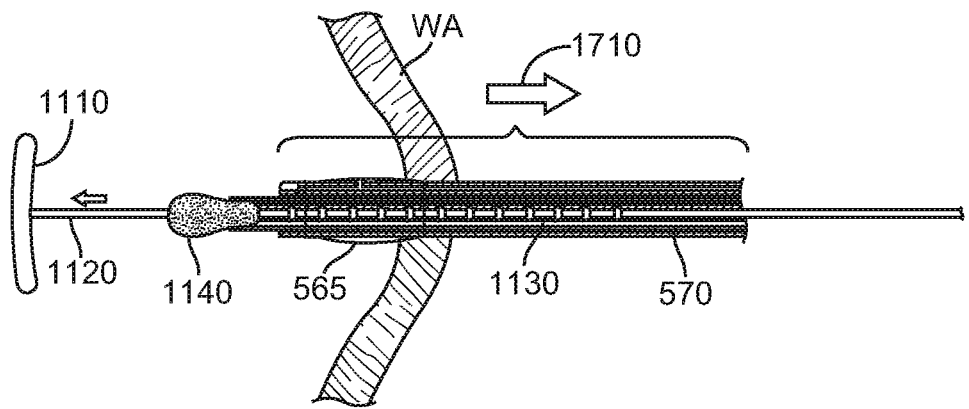
Figure 22:
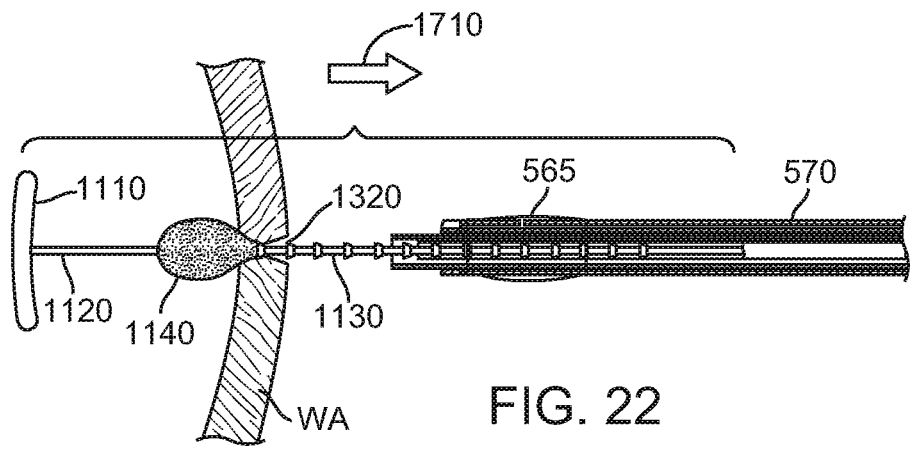
Figure 23:
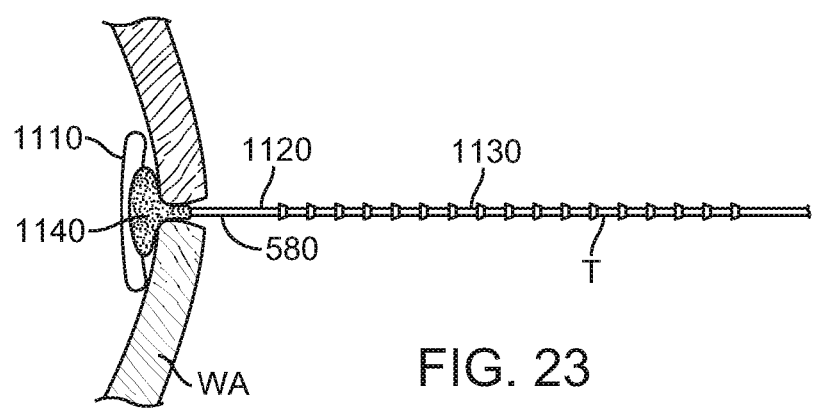
Figure 24:
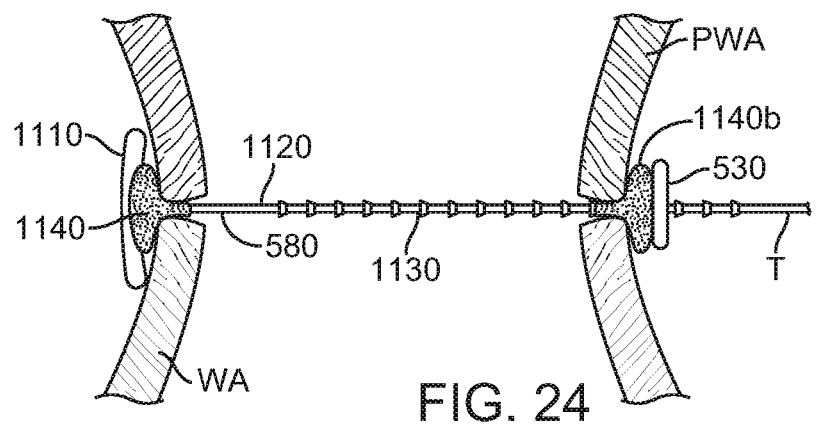

As shown in FIG. 15, introducer catheter 560 is further advanced such that expansion member 565 is past or distal of tissue wall WA, and the expansion member (typically comprising a balloon) is expanded. Guidewire 511 has been retracted. As shown in FIG. 16, balloon 575 is contracted or deflated as described above while expansion member 565 is expanded through distal expandable member inflation port 1320 which is coupled to expandable member inflation port 1210. As shown in FIG. 17, balloon dilator 570 is proximally retracted as indicated by arrow 1720. As indicated by proximally pointed arrow 1710, introducer catheter 560 is also moved proximally such that expansion member 565 is urged against tissue wall WA. As shown in FIG. 18, balloon dilator 570 has been fully retracted from center lumen 1240 of introducer catheter 560. As shown in FIG. 19, anchor assembly 580 has been advanced through center lumen 1240 of introducer catheter 560. As shown in FIG. 20, once distally advanced far enough, anchor assembly 580 is deployed. Portions of anchor assembly 580 may be radiopaque so that the position and orientation of anchor assembly 580 can be detected and manipulated to a desired orientation with respect to the long and short axes of the heart. As shown in FIG. 21, expansion member 565 is contracted or deflated and introducer catheter 560 is proximally retracted. As shown in FIG. 22, introducer catheter 560 has been fully retracted from tissue wall WA. As shown in FIG. 23, introducer catheter 560 has been fully retracted. Tether T is pulled proximally to apply tension and urge anchor arm 1010 against tissue wall WA in a proximal direction. Tether T may be rotated to rotationally position anchor assembly 580 as desired, for example, to match a contour of the heart. Anchor arm 1010 may push plug 1140 to be in contact with the distal end of perforation 1321 in tissue wall WA. Plug 1140 may comprise a compressible plug made of collagen sponge which may seal off any potential blood flow. As shown in FIG. 24, tether T may be advanced through a proximal tissue wall PWA. An external anchor arm 530, optionally along with a secondary plug 1140b, can be placed and secured through tether T. Proximal retraction of tether T while maintenance of external anchor arm 530 urged against the distal end of proximal tissue wall PWA may apply tension to tether T and reduce the distance between tissue walls WA and PWA. External anchor arm 530 may include features such as a ratchet which may couple with the repeating features, such as protrusions, barbs, or pawls 1130, of tether T to maintain tension and the reduced distance between tissue walls WA and PWA.

Figure 25:
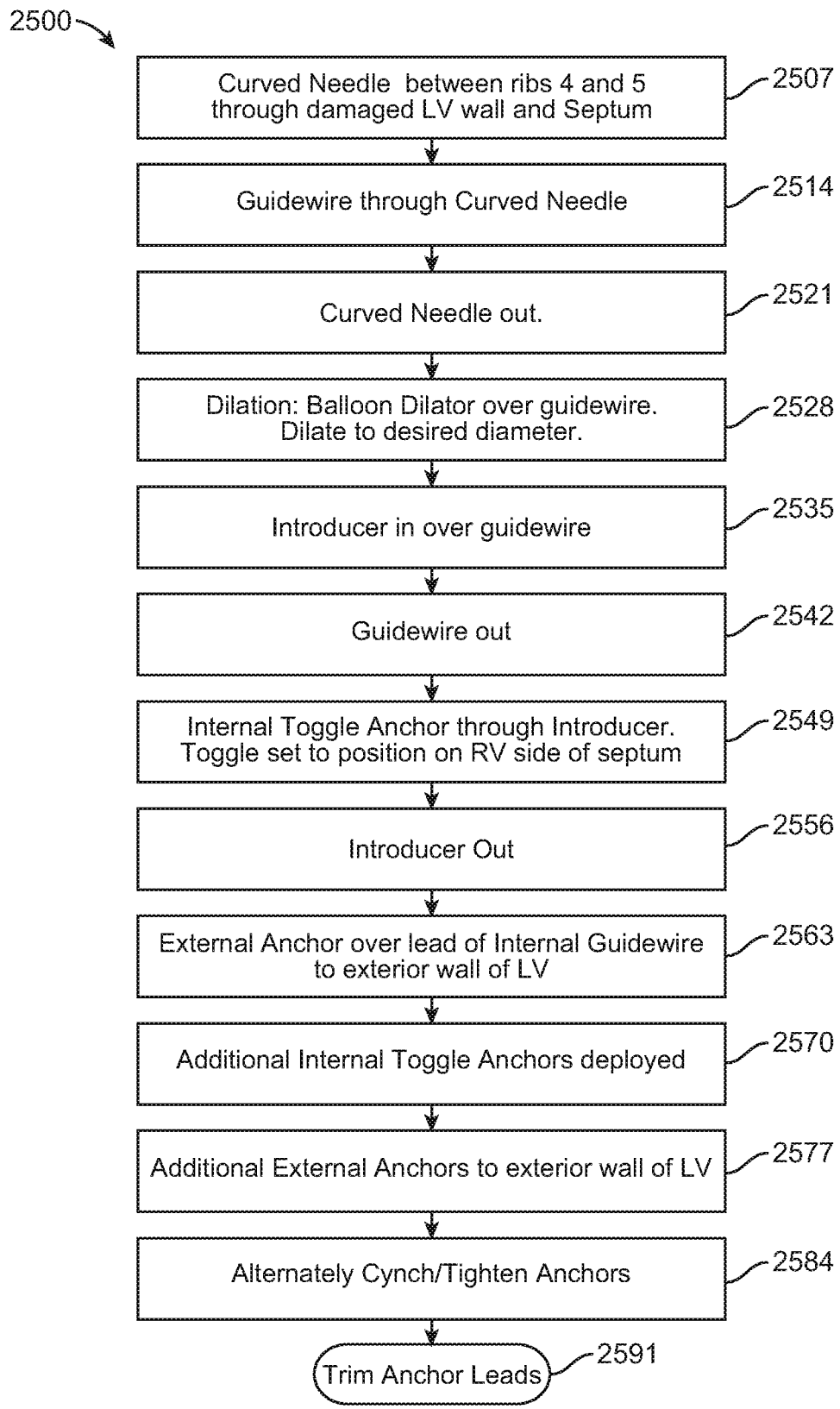
FIG. 25 is a block diagram schematically showing a method of reducing the distance between two points in tissue wall.
Figure 26:
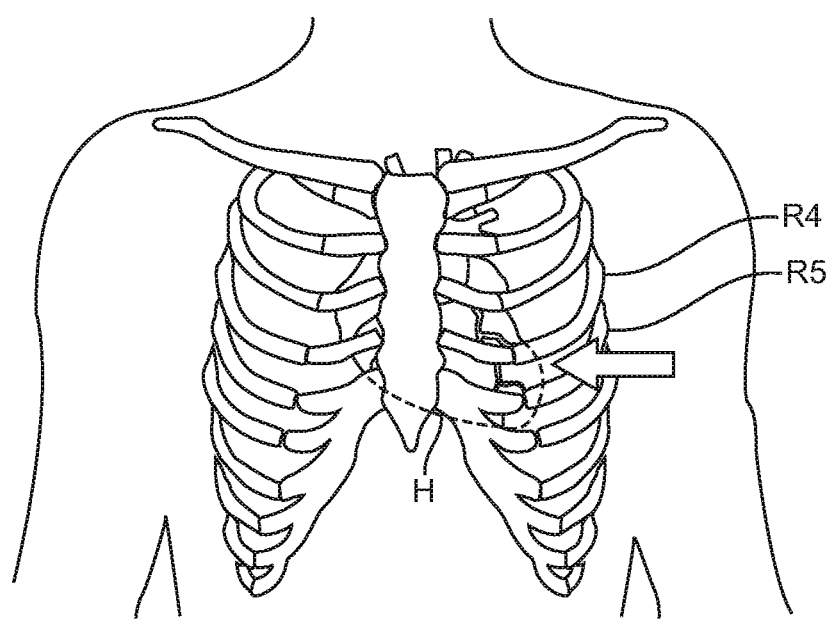
FIG. 26 shows some of the anatomy near a heart treatment site, including an adult human ribcage.

FIG. 25 schematically shows an exemplary method 2500 of reducing the distance between the walls of heart tissue and maintaining the reduced distance, thereby changing and reconfiguring the geometry of the heart. Method 2500 may change the geometry of the heart by excluding a selected portion of a ventricle. Method 2500 may be performed endoscopically. Method 2500 comprises steps 2507, 2514, 2521, 2528, 2535, 2542, 2549, 2556, 2563, 2570, 2577, 2584, and 2591. Prior to performing the steps of method 2500, a specified location on the outer surface of the heart may indentified to be the border of a proposed area of the heart to be excluded may be identified and a desired insertion path may be identified. A step 2507 places a curved needle, for example, guidewire introducer 520, between ribs R4 and R5 and through a damaged left ventricle LV wall and septum SE such that the distal tip of curved needle is located in the right ventricle RV. The curved needle can make perforations on specific locations in the left ventricle LV wall and septum SE wall so that curved needle may be passed through. The curved needle may be shaped or otherwise configured so that the perforations made on the heart walls are generally perpendicular to the respective tissue walls. A human rib cage with ribs R4 and R5 are shown in FIG. 26. The curved needle may be placed along an arc-shaped insertion path parallel or slightly oblique to the plane of the mitral valve, i.e., the "short axis" of the heart to a specified location on the septum SE. The length of tissue between the perforation on the left ventricle LV and the perforation on the septum SE may define the amount of circumference of the heart to be excluded. A step 2514 places a guidewire, for example, guidewire 511, through the curved needle, which may be hollow. Instead of a guidewire, a flexible sheath may be passed over the curved needle, for example, if the curved needle is of a solid core type or lacks a lumen. A step 2521 removes or outs the curved needle. If a solid core type curved needle and a flexible sheath are used, an additional step may be required. A guidewire may be threaded through the flexible sheath such that the tip of the guidewire is contained in the right ventricle, right atrium, pulmonary artery, vena cavae, or other right-sided vascular structure, with its proximal end protruding through the ventricular wall coming out of the proximal end of the flexible sheath, at which time, the flexible sheath is removed, leaving only the guidewire. A step 2528 places a balloon dilator and expands the balloon dilator to a desired diameter. A step 2535 places an introducer, for example, introducer catheter 560, over the guidewire. A step 2542 removes or outs the introducer. A step 2549 places an internal toggle anchor, for example, anchor 580, through the introducer and sets it in position on the right ventricular RV side of the septum SE. The internal toggle anchor may be rotated to a desired orientation. A step 2556 removes or outs the introducer. A step 2563 places an external anchor arm, for example, external anchor arm 530, over the lead of an internal guidewire of the internal anchor to the exterior wall of the left ventricle LV. A step 2570 deploys additional internal toggle anchors, for example, using at least some of the previously discussed steps including steps 2507, 2514, 2521, 2528, 2535, 2542, 2549, 2556, and 2563. A step 2577 deploys additional external anchor arms to the external wall of the left ventricle LV. A step 2584 alternately cinches and/or tightens the anchors, for example, to selectively reduce the distance between the septum and the left ventricle LV so that the geometry of heart H may be changed as desired. A step 2591 trims the anchor leads.

Figure 27:
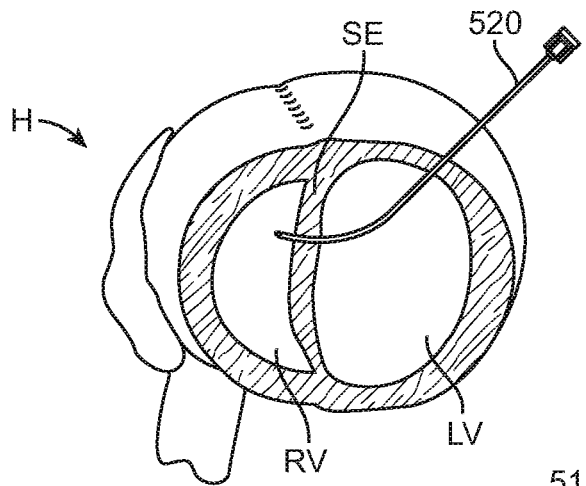
FIGS. 27-45 show a method of reducing the distance between opposed walls of a heart according to embodiments of the invention.
Figure 28:
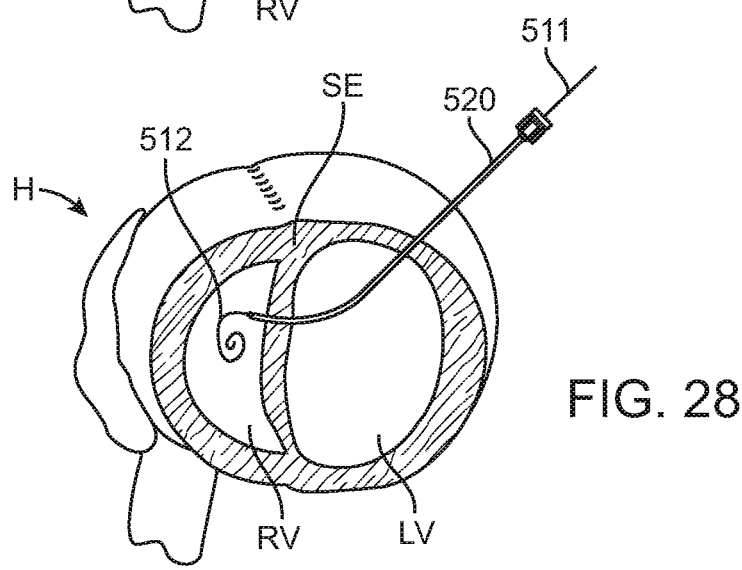
Figure 29:
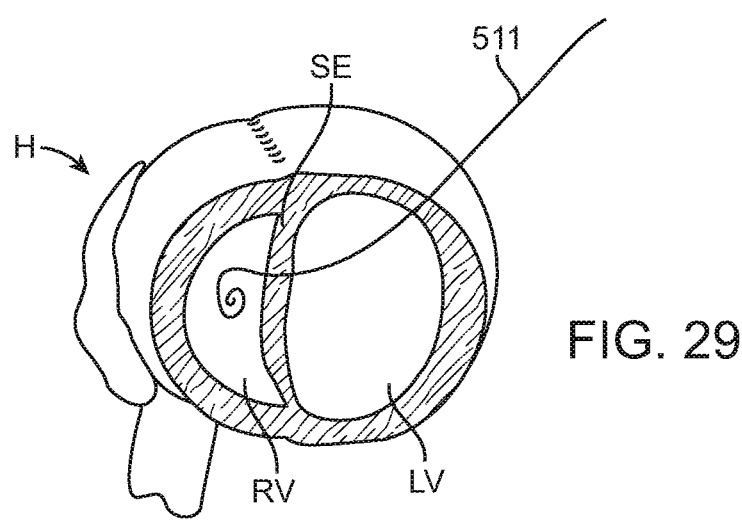
Figure 30:
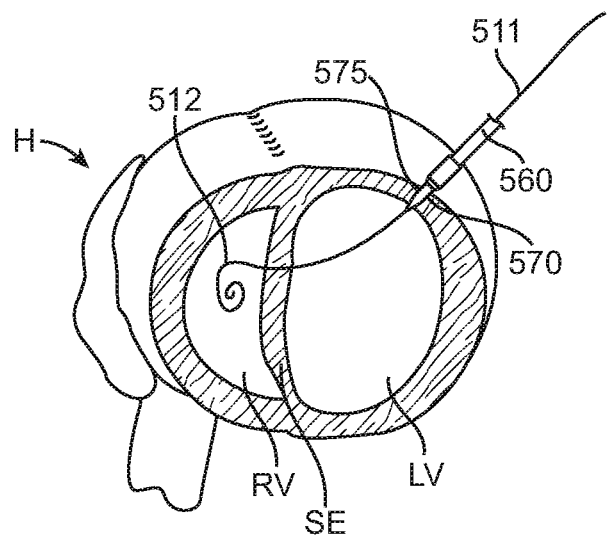
Figure 31:
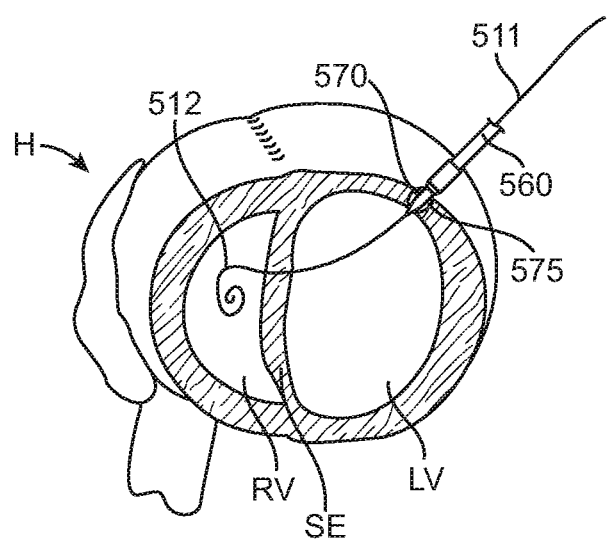
Figure 32:
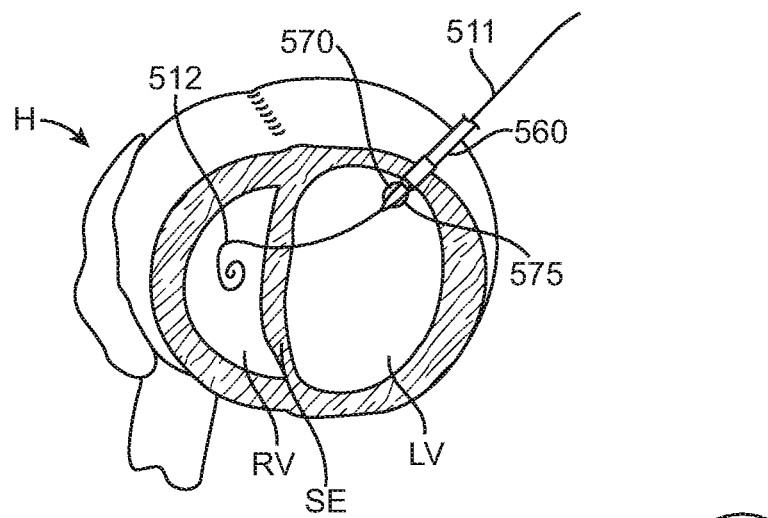
Figure 33:
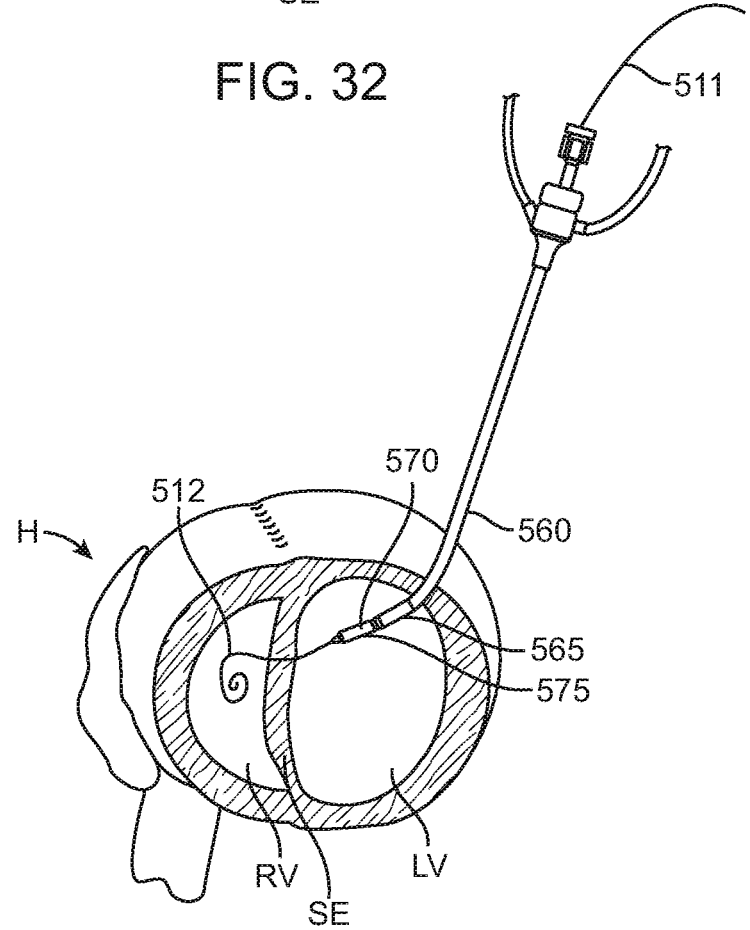
Figure 34:
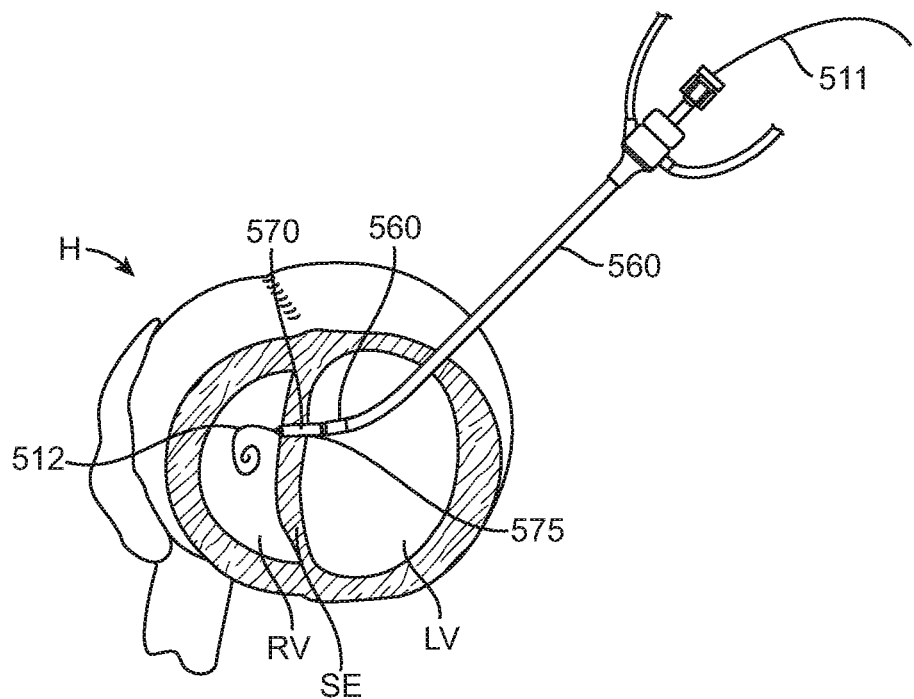
Figure 35:
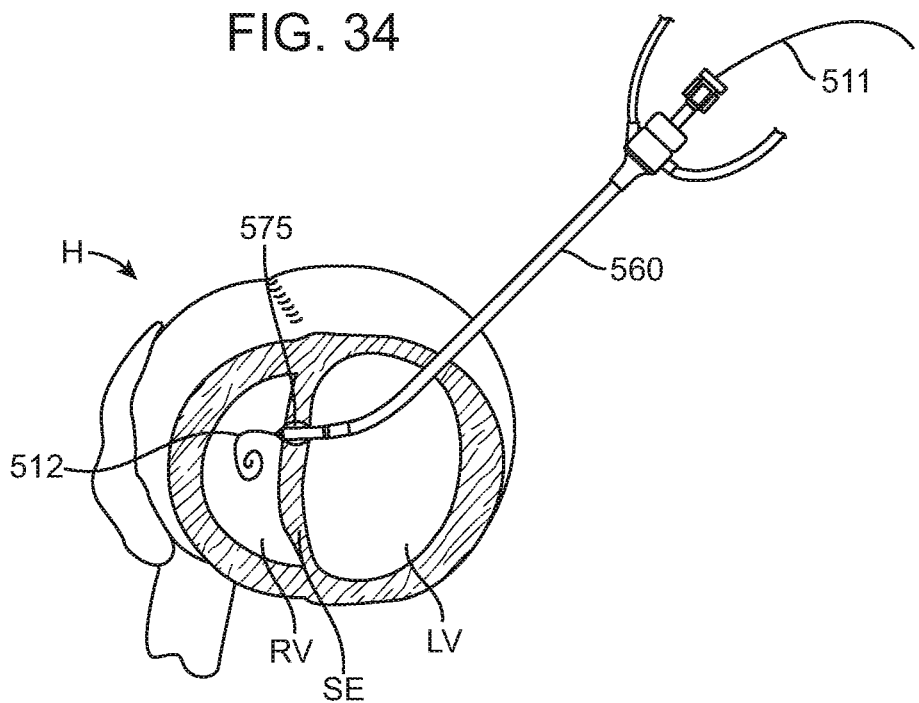
Figure 36:
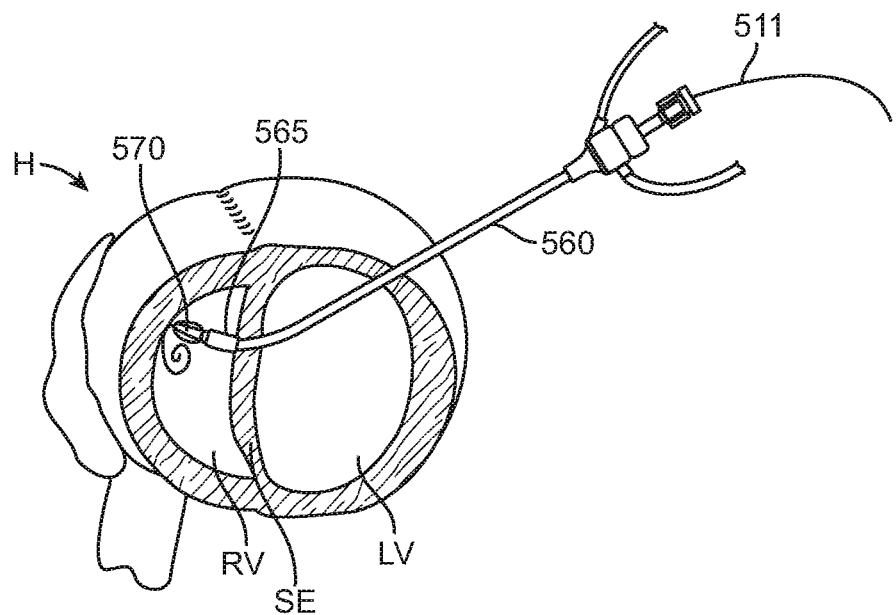
Figure 37:
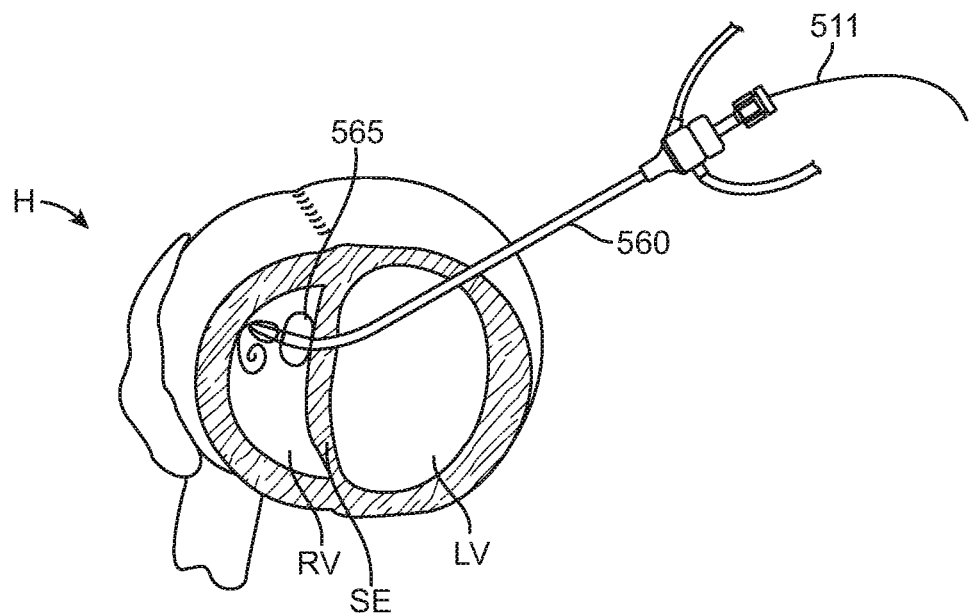
Figure 38:
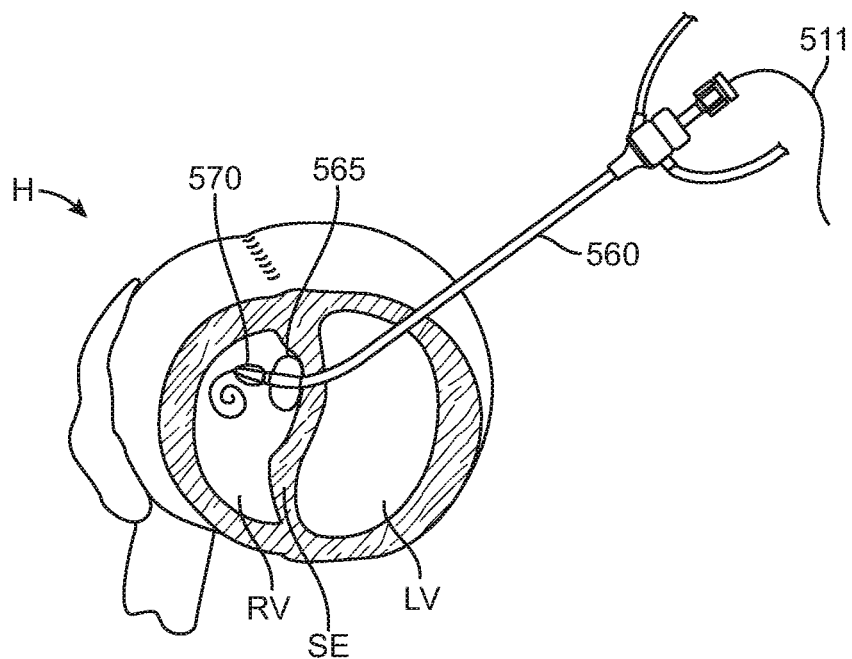
Figure 39:
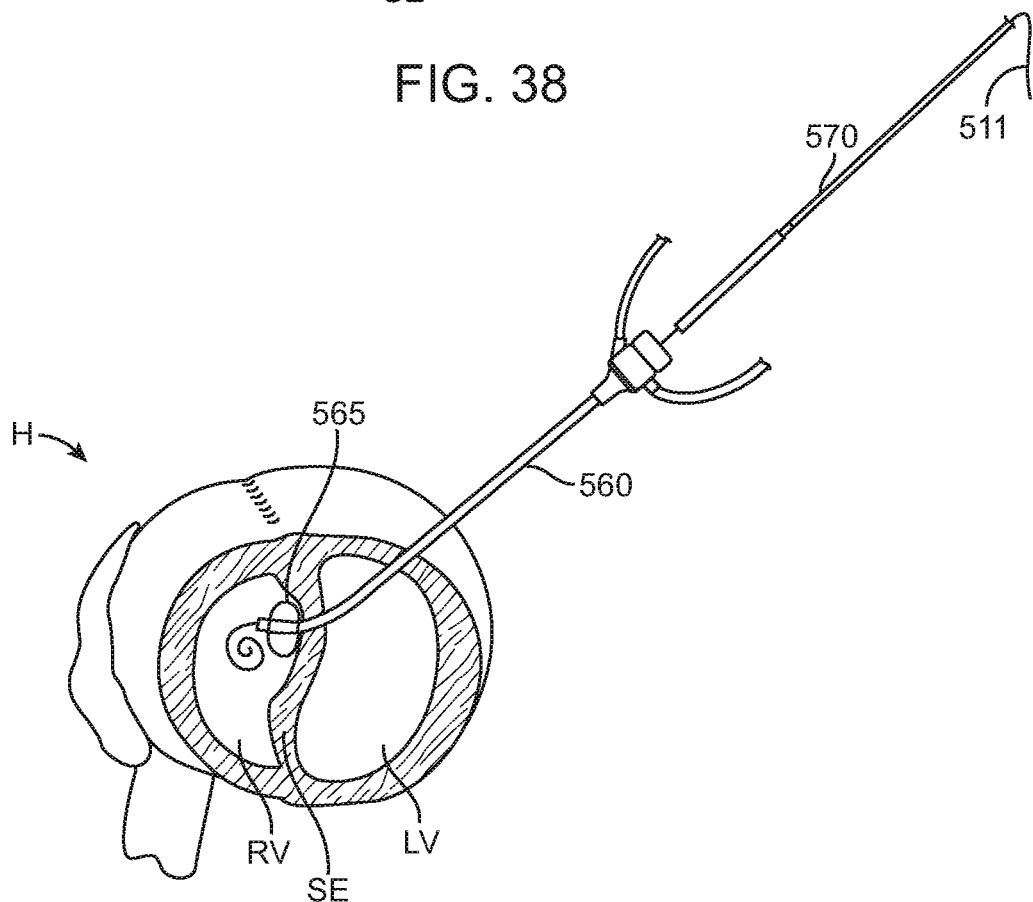
Figure 40:
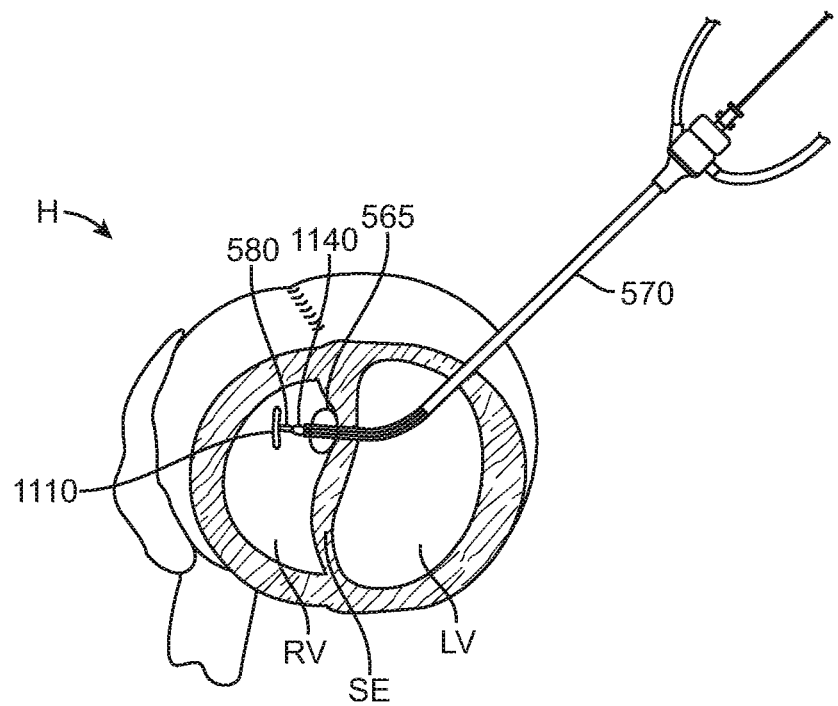
Figure 41:
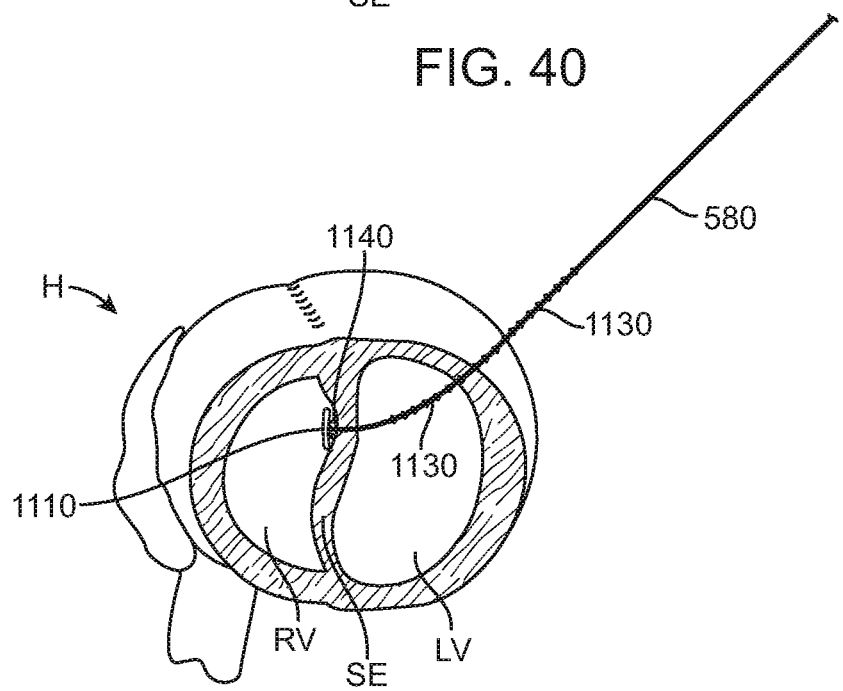
Figure 42:
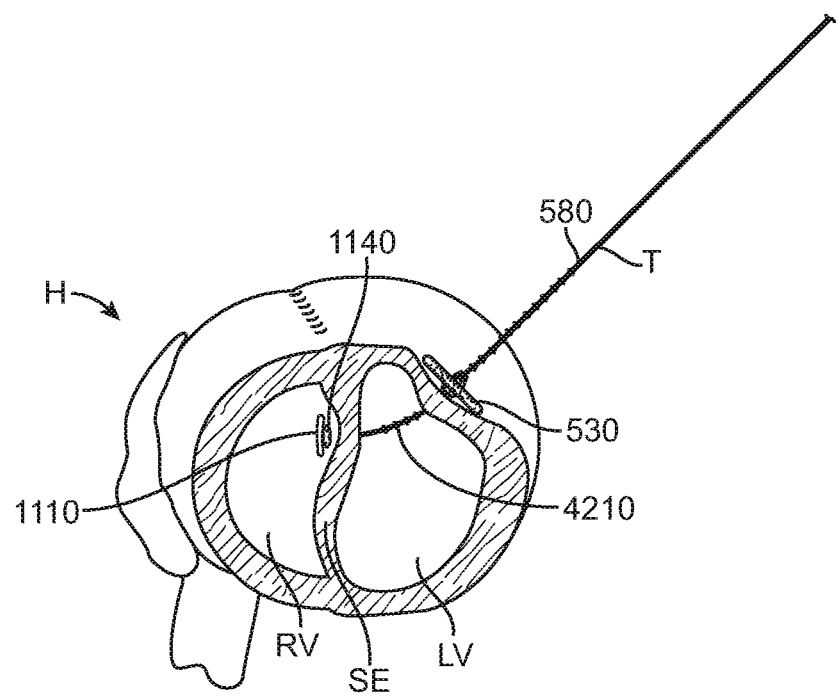
Figure 43:
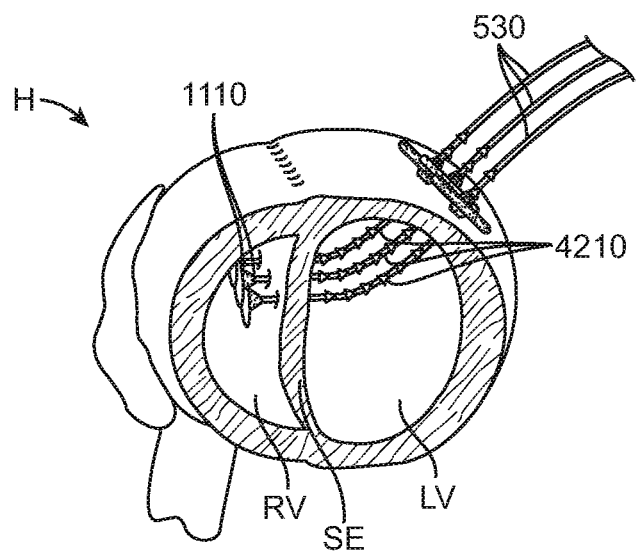
Figure 44:
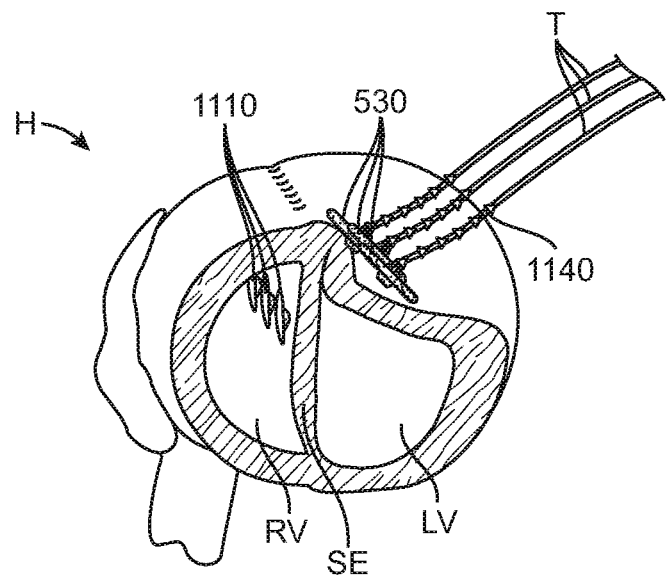
Figure 45:
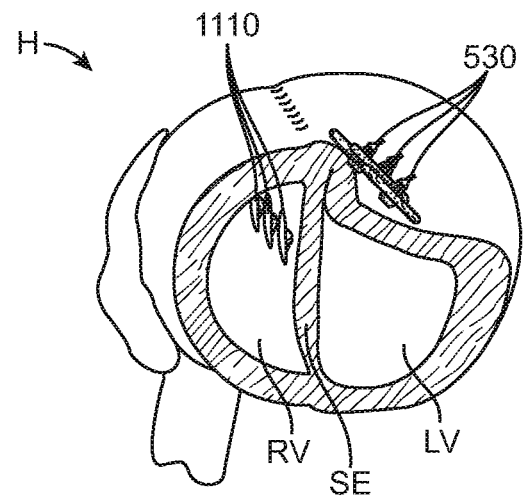

FIGS. 27-45 show an exemplary method of changing the geometry of the heart with a system 500 according to embodiments of the present invention. The method shown by FIG. 27-45 may be generally similar to method 2500 and may optionally be performed endoscopically, percutaneously, or otherwise in a less invasive manner. The heart may be accessed through, for example, a small incision made between the ribs or a thoracotomy. As shown in FIG. 27, a bent insertion needle or guidewire introducer 520 is passed through a desired insertion path through the left ventricle LV wall and through septum SE into the right ventricle RV. Guidewire introducer 520 may be configured so that the perforations made by guidewire introducer 520 on the left ventricular wall and the septum wall are perpendicular to their respective walls. As shown in FIG. 28, a guidewire 511 is placed through the lumen of guidewire introducer 520 so that guidewire 511 threads through the outer left ventricle LV wall, through the septum SE, and into the right ventricle RV. As shown in FIG. 29, guidewire introducer 520 has been removed. As shown in FIG. 30, introducer catheter 560 and balloon dilator 570 are advanced over guidewire 511 to contact the heart H. Balloon 575 is in contact with a perforation in the left ventricle LV wall. As shown in FIG. 31, balloon 570 is expanded to dilate the left ventricle LV wall. As shown in FIGS. 32 and 33, introducer catheter 560 and balloon dilator 570 are further advanced into the heart. As shown in FIG. 33, balloon 575 is deflated. As shown in FIG. 34, balloon introducer catheter 560 and balloon dilator 570 are further advanced. Balloon 575 contacts a perforation in the septum SE wall. As shown in FIG. 35, balloon 575 is expanded to dilate the septum SE wall. As shown in FIG. 36, introducer catheter 560 and balloon dilator 570 are further advanced through the septum SE wall. Balloon 575 is deflated. As shown in FIG. 37, expansion member 565 is expanded. As shown in FIG. 38, introducer catheter 560 is pulled proximally so that expanded expansion member 565 urges against the septum SE wall. As shown in FIG. 39, balloon dilator 570 is removed from center lumen 1240 of balloon introducer 560. As shown in FIG. 40, guidewire 511 is removed and anchor assembly 580 is advanced, for example, through the use of a pushrod, through center lumen 1240 of balloon introducer 560. The distal end of anchor assembly 580, which was parallel to tether T, exits balloon introducer 560 and is rotated so that it is generally perpendicular to tether T, i.e., anchor assembly 580 is laterally deployed into right ventricle RV. Anchor assembly 580 may be rotated via tether T to align or position anchor arm 1110 along a contour as desired. As shown in FIG. 41, expansion member 565 is contracted or deflated and balloon introducer 560 is removed. Anchor assembly 580 is pulled proximally so that arm 1110 urges against the septum SE wall. As shown in FIG. 42, an external anchor arm 530 is placed over tether T of anchor assembly 580, leaving a central region 4210 of tether T in the left ventricle. The steps shown in FIGS. 27-42 can be repeated one or more times for different, adjacent locations of the heart H, for example, as shown in FIG. 43. Arms 1110 are rotated to generally extend along the contour or line connecting the perforation sites. Tethers T can be pulled proximally to apply tension while external anchor arms 530 are advanced distally, thus reducing the length of central region 4210 and drawing the walls of the left ventricle LV and the septum SE together. External anchor arms 530 may comprise features such as a ratchet which may couple with the repeating features, protrusions, barbs, or pawls 1130 of tether T thus maintaining the reduced central region 4210. As shown in FIG. 45, tethers T are trimmed. Depending on the number and locations of anchor assemblies 580 and anchor arm pairs comprising anchor arms 1110 and external anchor arms 530 and also the amount of tension applied to anchor assemblies 580, the walls of the left ventricle LV and septum SE may be shaped into a desired contour.

The result of the deployed anchor assemblies 580 with anchor arm pairs of anchor arms 1110 and external anchor arms 530 may be a solid, continuous line, contour, or wall of approximation of two adjacent heart walls that will partition and clearly define a portion of the heart which remains in contact with the blood and another portion of the heart that will be excluded from continuity with the chamber. A line or contour of apposition can be formed. The excluded portion may be treated by insertion, injection, or otherwise treating the cavity of the excluded portion to form a clot or fibrosis. For example, sclerotic substances, coils, tissue glues, and the like may be injected in the cavity of the excluded portion. Specific residual fistulae between excluded and included portions of the left ventricular LV chamber may likewise be treated. Single or multiple pairings of anchor assemblies 580 and external anchor arms 530 may be added on the included portion of the line of apposition to increase the magnitude of volume and radius reduction. Migration of anchor positions can be fixed in place in the heart H by a perforating tensile member attached to a middle internal anchor and passed through a customized through-and-through aperture in the external anchor arm, allowing adjustable inter-anchor distance between the anchor a pairing of anchor assembly 580 and external anchor arm 530.

Figure 45A:
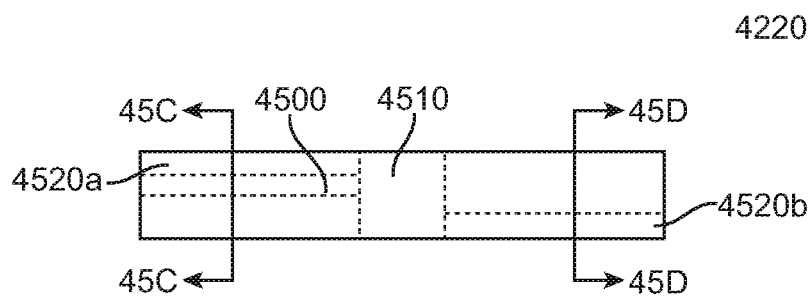
FIGS. 45A-45O show exemplary embodiments of external anchors arm according to embodiments of the invention.
Figure 45B:
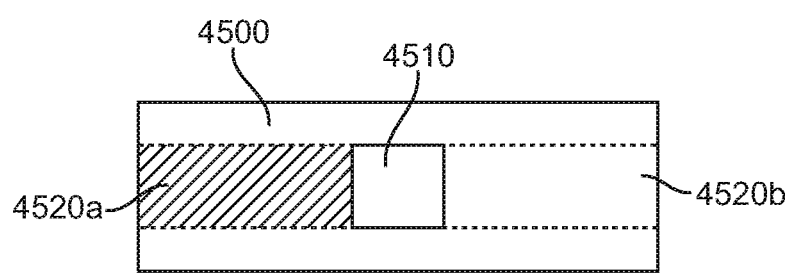
Figure 45C:
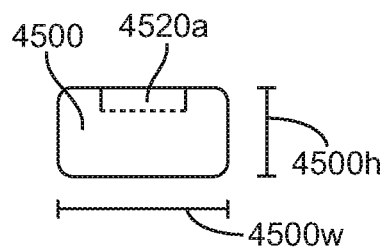
Figure 45D:
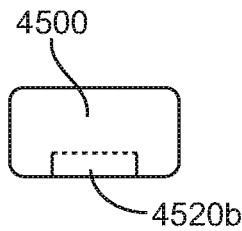
Figure 45E:
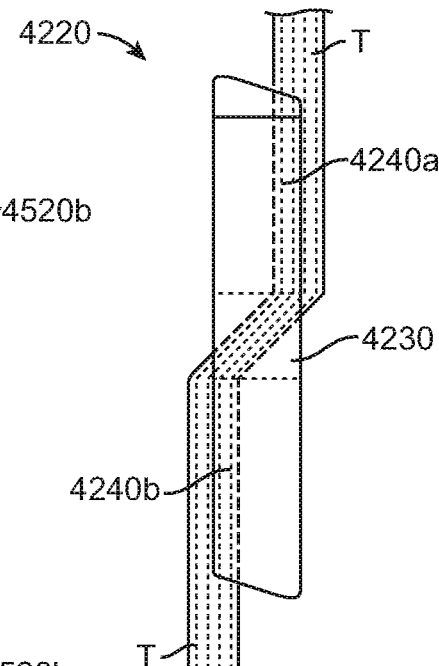
Figure 45G:
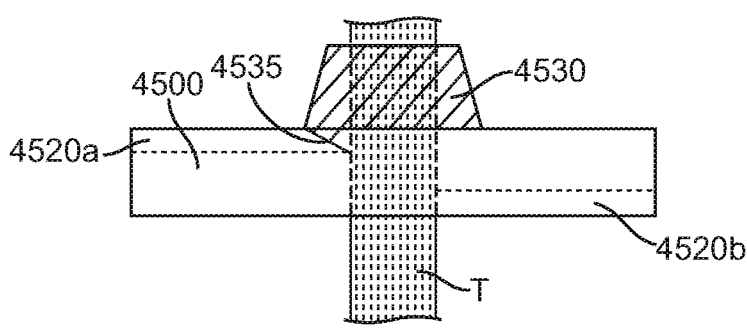
Figure 45F:
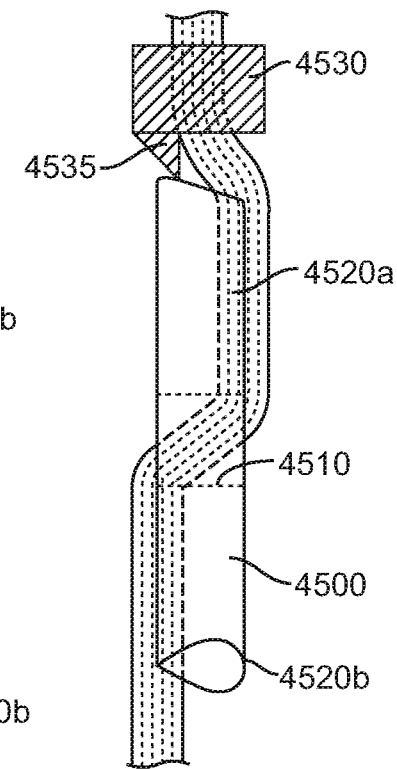

FIGS. 45A-45G show an exemplary external anchor arm 4500 with external here encompassing outside the chambers of the heart or in the pericardial space. External anchor arm 4500 may be similar to and can be used in a substantially similar manner as external anchor arm 530. FIG. 45A shows a side view of external anchor arm 4500. FIG. 45B shows a top view of external anchor arm 4500. FIGS. 45C and 45D both show cross-sectional views of external anchor arm 4500. External anchor arm 4500 defines a channel or aperture 4510 through which tether T may be threaded through. External anchor arm 4500 comprises a space 4520a and a space 4520b. External anchor arm 4500 may have asymmetrically rounded leading ends. When tether T is threaded through aperture 4510, external anchor arm 4500 may be rotated such that space 4520a and space 4520b accommodate tether T as shown in FIGS. 45E and 45F. This accommodation can allow external anchor arm 4500 to be advanced over tether T when both tether T and external anchor arm 4500 are within a sheath or a tube.

It may be advantageous to include a locking mechanism such that when activated, external anchor arm 4500 is fixed in place relative to anchor 580. The locking mechanism can fix external anchor arm 4500 to the tether T and may be reversible and removable. The locking mechanism may comprise friction devices, ratchets, cam-devices, and the like and may be built into or onto external anchor arm 4500. The locking mechanism may be disposed nearby or within channel 4510 and may be oriented towards the interior of channel 4510. For example, the locking mechanism may comprise locking element 4530 comprising a wedge 4535. Tether T can be threaded through locking element 4530. As seen in FIG. 45G, wedge 4535 may occupy a space in external anchor arm 4500 when external anchor arm 4500 is perpendicular to tether T. In certain embodiments, locking element 4530 is placed proximal of external anchor arm 4500 and is advanced along with external anchor arm 4500 over tether T. Wedge 4535 and/or the asymmetrically rounded leading edge of external anchor arm 4500 may initiate rotation of external anchor arm 4500 when external anchor arm 4500 exits a sheath or tube and encounters resistance to further advancement, for example, as when tissue is contacted.

Figure 45I:
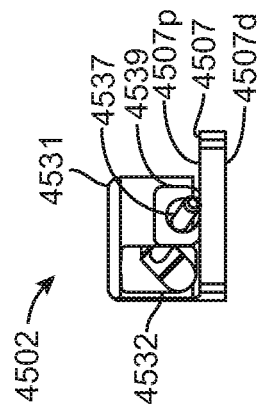
Figure 45J:
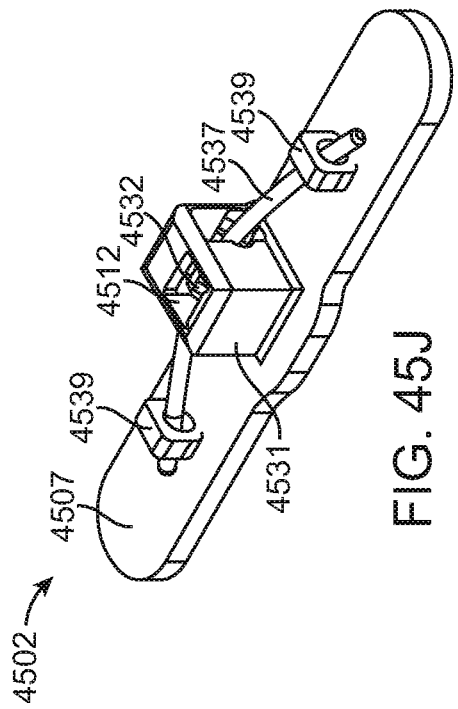
Figure 45G:
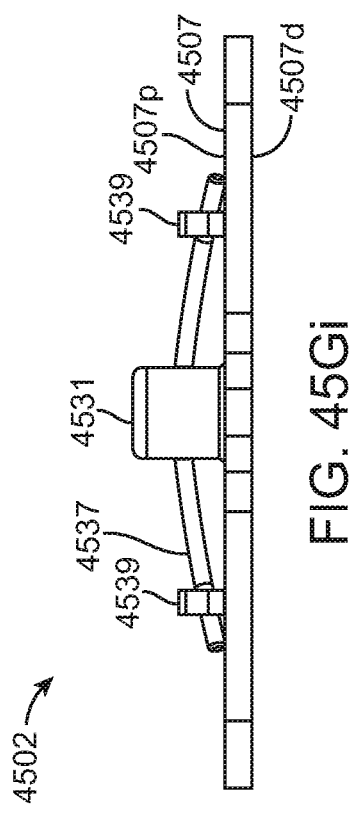
Figure 45H:
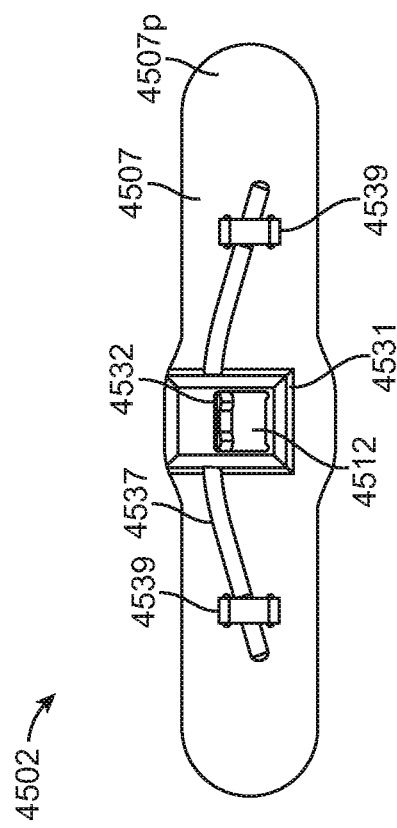

FIGS. 45Gi-45J show an exemplary external anchor arm assembly 4502. FIG. 45Gi shows a side view of external anchor arm assembly 4502. FIG. 45H shows a bottom or proximal view of external anchor assembly 4502. FIG. 45I shows a profile of external anchor assembly 4502. FIG. 45J shows a perspective view of external anchor assembly 4502. External anchor arm assembly may be used in a similar manner as external anchor arm 530 and external anchor arm 4500 described above. External anchor arm assembly 4502 comprises an external anchor arm base 4507 with a proximal surface 4507p and a distal surface 4507d. In use, external anchor arm assembly 4502 can be oriented so that proximal surface 4507p faces the proximal direction and distal surface 4507d faces the distal direction. External anchor assembly 4502 comprises a locking or friction mechanism 4531. Friction mechanism comprises a friction imposing surface 4532 coupled to an elastic band or resilient spring wire 4537. Spring 4537 is held by rings 4539. External anchor arm assembly 4502 may comprise a rectangular channel 4512. When tether T is threaded through rectangular channel 4512, spring 4537 may urge friction imposing surface 4531 against tether T once the tether has been tensioned. More specifically, the orientation of engagement between the friction imposing surface 4532 and pivotal movement of the friction imposing surface 4532 away from the tether T when the tether T is pulled proximally through the proximal anchor so as to bring the walls toward each other allows sliding movement in one direction. In contrast, the friction imposing surface 4532 pivots cam-like toward the engaged surface of the tether T when the tether T is pulled distally (for example, when the anchors are pulled away from each other) and may lock external anchor arm base 4507 in place relative to tether T.

Figure 45K:
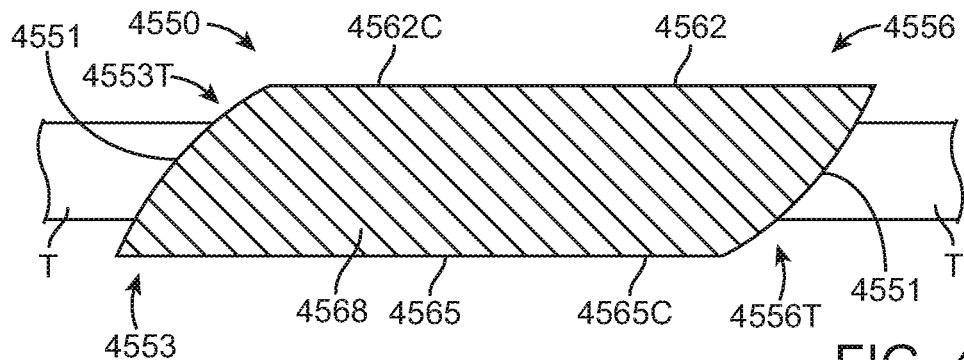
Figure 45L:
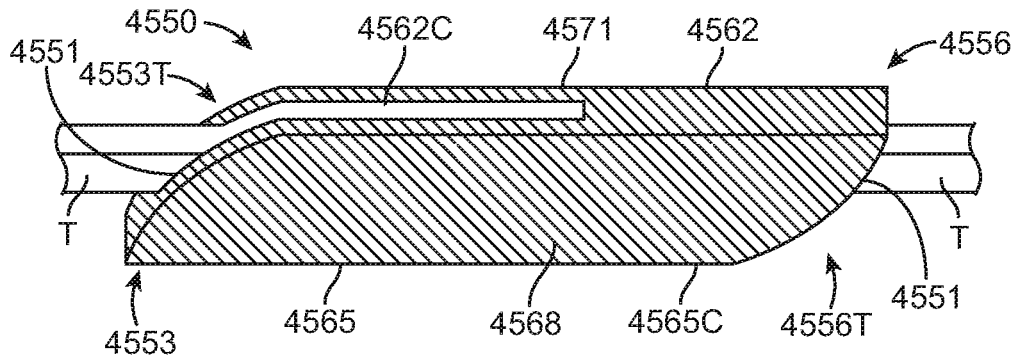
Figure 45M:
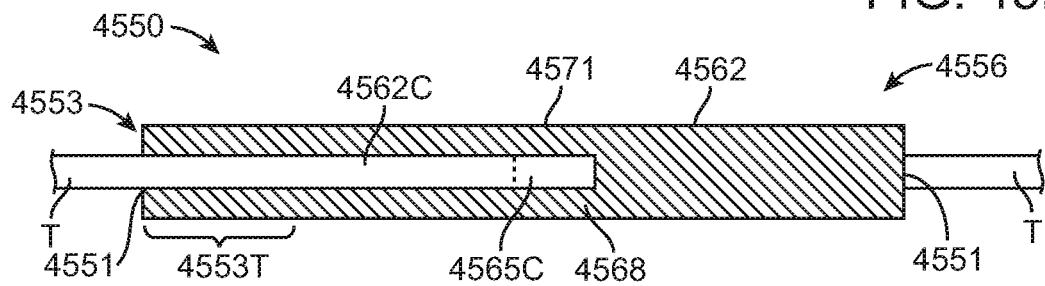
Figure 45N:
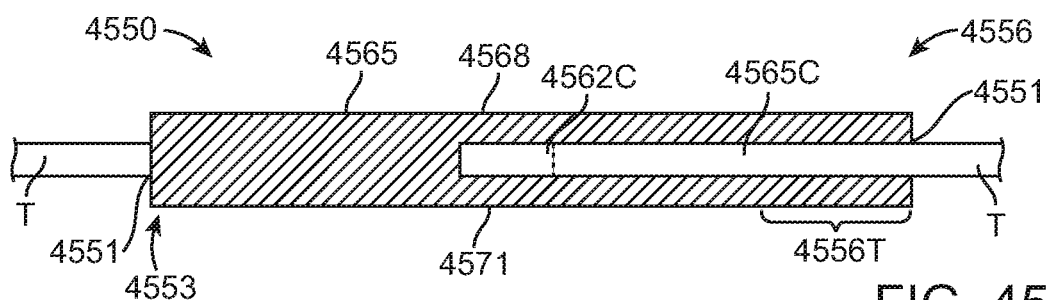
Figure 45O:
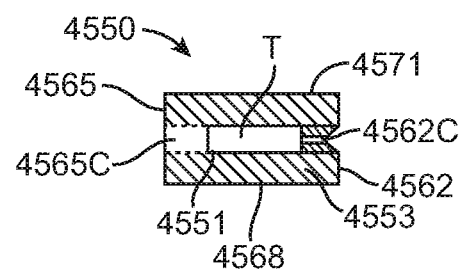

FIGS. 45K-45O show an other exemplary external anchor arm 4550. External anchor arm 4550 may share similar features with and may be used in a similar manner as external anchor arms 530, 4500, and 4502 described above. FIG. 45K-45N each show a view of external anchor arm 4550 with a tether T threaded through a channel 4551. FIG. 45K shows a top view, FIG. 45L shows a perspective view, FIG. 45M shows a top side view, FIG. 45N shows a bottom side view, and FIG. 45O shows a front view. External anchor arm 4550 comprises a distal end 4553, a roundly tapered distal portion 4553T, a proximal end 4556, a roundly tapered proximal portion 4556T, a first narrow side 4562 with a distal opening 4562C, a second narrow side 4565 with a proximal opening 4565C, a first wide side 4568, and a second wide side 4571. When Tether T is threaded through channel 4551, first narrow side 4562, second narrow side 4565, first wide side 4568, and second wide side 4571 form a rectangular box around tether T. First wide side 4568 and second wide side 4571 fully cover tether T. First narrow side 4562 and second narrow side 4565 cover tether T partially. Distal opening 4562C of first narrow side 4562 and proximal opening 4565C of second narrow side 4565 do not cover tether T. Distal opening 4562C is directly opposite a solid proximal portion of second narrow side 4565. Likewise, proximal opening 4565C is directly opposite a solid distal portion of first narrow side 4562. There is a degree of overlap between distal opening 4562C and proximal opening 4565C. The height and width of this overlap will often be equal to that of the cross-section of tether T. As external anchor arm 4550 is advanced distally over tether T and eventually into contact with an external wall of a heart, further distal advancement of external anchor arm 4550 will cause external anchor arm 4550 to rotate. This rotation is due a redirection of force by the shape of roundly tapered distal portion 4553T and the accommodation of tether T by openings 4562C and 4565C. Because of wide sides 4568 and 4571 fully cover tether T and openings 4562C and 4565C are specifically sized and oriented as described above, external anchor arm 4550 is only allowed to rotate no more than 90° in one direction. Once external anchor arm 4550 has contacted the external wall of the heart and has rotated approximately 90° to be parallel to the external wall of the heart, narrow side 4562 is in intimate contact with the external wall of the heart. External anchor arm 4550 may then be fixed onto tether T with a lock mechanism. A lock mechanism may be built into external anchor arm 4550 or may comprise an external locking element such as locking element 4530.

FIGS. 46A, 46B, 47A, 47B, 48A, 48B, 49A, 49B, 50A, 50B, 51A, 51B, and 52 schematically show alternative exemplary embodiments of the distal arm of an anchor according to embodiments of the invention, for example, for use as anchor 580.

FIGS. 46A and 46B show leading end 4600. Leading end 4600 is generally similar to the distal or leading ends of anchor 580 as described above. Leading end 4600 comprises an elongate shaft 4610 coupled to a distal arm 4620 through a joint or flexible region 4630. In the undeployed form of leading end 4600 as shown in FIG. 46A, arm 4620 can be turned on its side so both arm 4620 and elongate shaft 4610 can fit within sheath 1150. As shown in FIG. 46B, when no longer constrained by sheath 1150, arm 4620 resiliently returns to its deployed form in which arm 4620 is generally perpendicular to elongate shaft 4610.

FIGS. 47A and 47B show leading end 4700. Leading end 4710 comprises an elongate shaft 4710 coupled to a distal arm 4720 through a joint or flexible region 4630. In the undeployed from of leading end 4700 as shown in FIG. 47A, arm 4720 can be folded in half so that both arm 4720 and elongate shaft 4710 can fit within sheath 1150. As shown in FIG. 47B, when no longer constrained by sheath 1150, arm 4720 resiliently returns to its deployed form in which arm 4720 is generally perpendicular to elongate shaft 4710.

FIGS. 48A and 48B show leading end 4800. Leading end 4800 comprises an elongate shaft 4810 coupled to a distal arm 4820 through a joint or flexible region 4830. Distal arm 4820 can further comprise side arms 4840 which are disposed on the ends of distal arm 4840 and are generally perpendicular to both elongate shaft 4810 and distal arm 4820. As shown in FIG. 48B, side arms 4840 extend from opposite sides and opposite ends of distal arm 4820. In the undeployed form of leading end 4900 as shown in FIG. 48A, arm 4820 can be turned on its side and side arms 4840 tucked within arm 4820 so that arm 4820, side arms 4840, and elongate shaft 4610 can fit within sheath 1150. As shown in FIG. 46B, when no longer constrained by sheath 1150, arm 4820 along with side arms 4840 resiliently return to its deployed form in which arm 4820 is generally perpendicular to elongate shaft 4810.

FIGS. 49A and 49B show leading end 4900. Leading end 4900 comprises an elongate shaft 4910 coupled to a distal arm 4920 through a joint or flexible region 4930. Distal arm 4920 can further comprise an inner arm 4940 which can be disposed within distal arm 4920 and is generally perpendicular to both elongate shaft 4910 and distal arm 4920 when leading end 4900 is laterally deployed. As shown in FIG. 49B, side arms 4940 extend from opposite sides and opposite ends of distal arm 4920. In the undeployed form of leading end 4900 as shown in FIG. 49A, arm 4920 can be turned on its side and inner arm 4940 tucked within arm 4920 so that arm 4820, inner arms 4940, and elongate shaft 4910 can fit within sheath 1150. As shown in FIG. 46B, when no longer constrained by sheath 1150, arm 4920 along with inner arm 4940 resiliently return to its deployed form in which arm 4920 is generally perpendicular to elongate shaft 4910.

FIGS. 50A and 50B show leading end 5000. Leading end 5000 comprises an elongate shaft 5010 coupled to a distal arm 5020 through a joint or flexible region 5030. Distal arm 5020 can further comprise side arms 5040 which are disposed on the ends of distal arm 5040 and are generally perpendicular to both elongate shaft 5010 and distal arm 5020. As shown in FIG. 50B, side arms 5040 extend from opposite ends of distal arm 5020. The ends of side arms 5040 are connected to each other by bands 5060. In the undeployed form of leading end 5000 as shown in FIG. 50A, arm 5020 can be turned on its side and side arms 5040 can be tucked within arm 5020 so that arm 5020, side arms 5040, and elongate shaft 5010 can fit within sheath 1150. As shown in FIG. 50B, when no longer constrained by sheath 1150, arm 5020 along with side arms 5040 resiliently return to its deployed form in which arm 5020 is generally perpendicular to elongate shaft 5010 and side arms 5040 are generally perpendicular to both arm 5020 and shaft 5010.

FIGS. 51A and 51B show leading end 5100. Leading end 5100 is generally similar to leading end 4900 described above with reference to FIGS. 49A and 49B. Leading end 5100 further comprises bands 5110 which connect the ends of side arm 4940 to the ends of distal arm 4920.

Figure 52:
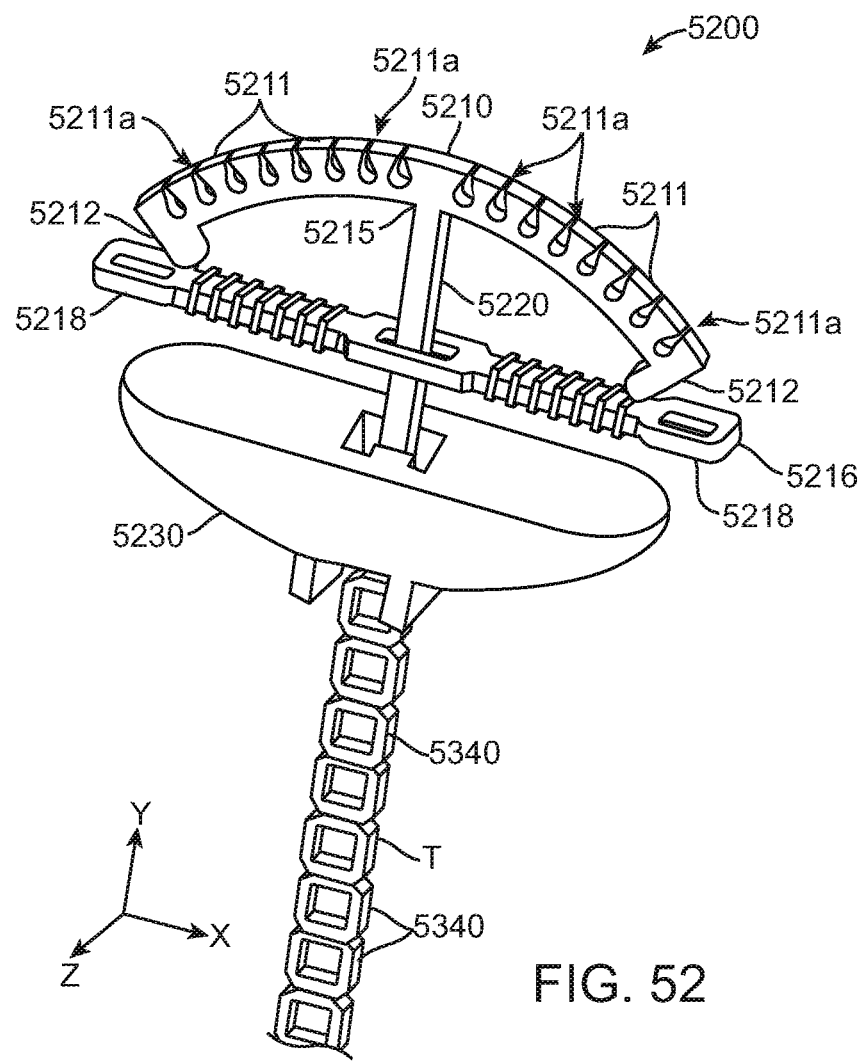
Figure 52A:
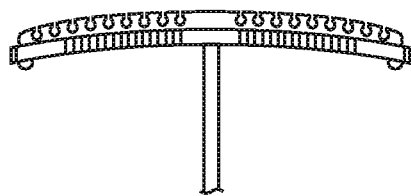
Figure 52B:
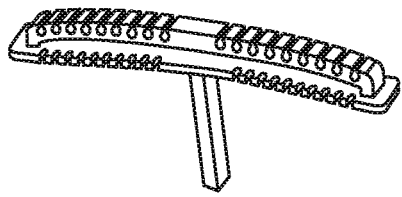

FIG. 52 shows selected components of a distal end 5200 of an alternative anchor assembly. Distal end 5200 comprises a distal anchor arm body 5210. Distal arm 5210 comprises a plurality of repeating elements 5211 which are formed by a plurality of distally facing cuts 5211a. Repeating elements 5211 can allow the opposed distal arms of body 5210 to flex proximally, while engagement between the repeating elements inhibits flexing of the arms distally. Opposite ends of distal arm 5210 include protrusions 5212 which can allow distal arm 5210 to couple with secondary distal arm 5216 through apertures 5218 located on opposite ends of secondary distal arm 5216, the secondary arm thereby forming a proximal beam web to further inhibit distal flexing of the anchor. The apertures 5218 may be laterally longer than protrusions 5212 so as to accommodate proximal flexing of the distal arm body 5210. Distal arm 5210 is connected to elongate shaft 5220 through a living hinge 5215. Elongate shaft 5220 is coupled to tether T. Tether T comprises a plurality of repeating members 5240. Repeating members 5240 comprise a series of apertures or slots. External anchor arm 5230, which can be threaded over tether T, may comprise a plurality of repeating features, protrusions, barbs, or pawls which may fit into at least one of repeating feature 5240, thereby locking external anchor arm 5230 in place relative to tether T and anchor 5210. Anchor structures similar to that of FIG. 52 are seen in FIGS. 52A and 52B.

Figure 53:
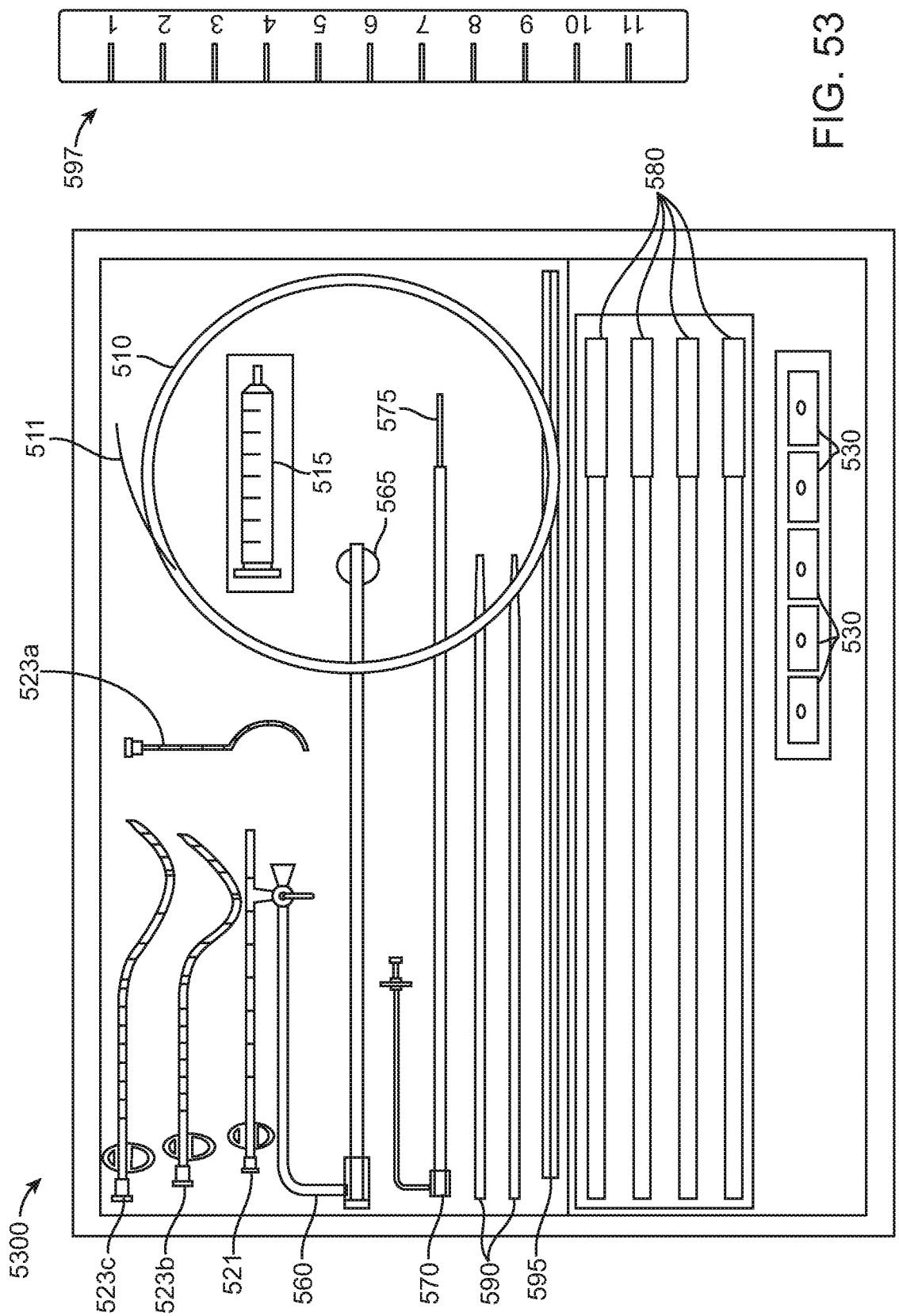
FIG. 53 shows a system according to embodiments of the invention for treating congestive heart failure.
Figure 53A:
FIGS. 53a-53d show guidewire introducers according to embodiments of the invention.
Figure 53B:
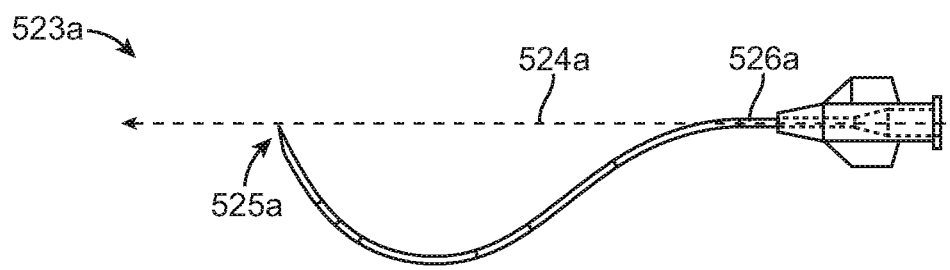
Figure 53C:
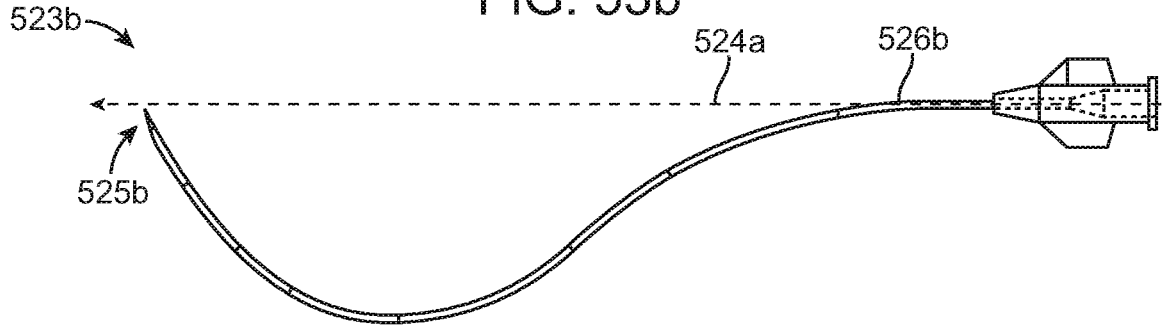
Figure 53D:
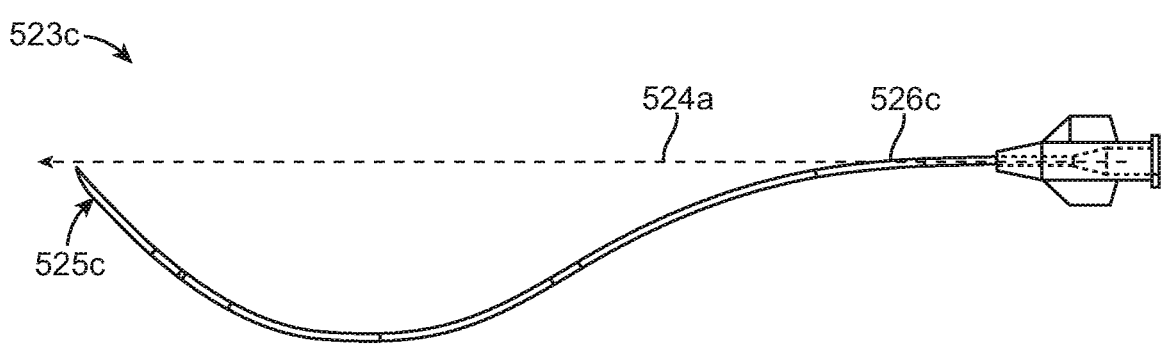

It should be appreciated that systems for treating congestive heart failure according to embodiments of the invention may comprise different combinations of different components or elements. For example, FIG. 53 shows a system 5300 for treating congestive heart failure. System 5300 may share many of the same components or elements as system 500, for example, introducer catheter 510, guidewire 511, syringe 515, external anchor arms 530, balloon introducer 560, balloon dilator 570, and anchors 580. System 5300 may further comprise a placement scale 597, a push rod 595, dilation members 590, a straight hollow bore insertion needle or guidewire introducer 521, a curved hollow bore insertion needle or guidewire introducer 523a, a curved hollow bore insertion needle or guidewire introducer 523b, and a curved hollow bore insertion needle or guidewire introducer 523c. A dilation member 590 has a tapered distal end and can be sized so that it can be axially translated within a central lumen of balloon introducer 560. The tapered distal end of dilation member 590 may dilate a perforation in a wall of a heart as dilation member 590 is advanced such that a balloon introducer 560 can be threaded through the perforation. In some cases, only dilation members 590 are used to dilate a perforation in a heart wall and the use of a balloon 575 on the distal end of balloon dilator 570 to expand or dilate a perforation in the heart wall may not be necessary.

FIGS. 53a, 53b, 53c, and 53d a show straight hollow bore insertion needle 521, a first curved hollow bore insertion needle 523a, a second curved hollow bore insertion needle 523b, and a third curved hollow bore insertion needle 523, respectively. Straight hollow bore insertion needle 521 has a sharp distal tip 522. Curved hollow bore insertion needle 523a has a sharp distal tip 525a which is aligned with an axis 524a of proximal straight portion 526a. A distal portion of insertion of insertion needle 523a is curved. The radius of curvature of the curved distal portion may be selected such that when insertion needle 523a is inserted into the heart at a first specified point, sharp distal tip 525a perforates the left ventricular wall at a roughly right angle and also perforates the septal wall at a roughly right angle at a second specified point as insertion needle 523a is further advanced, with the first and second perforation points being separated by a distance in a first desired range. Curved hollow bore insertion needle 523b has a sharp distal tip 523b which is aligned with axis 524b, which is the central axis of proximal straight portion 526d. A distal portion of insertion of insertion needle 523b is curved. The radius of curvature of the curved distal portion may be selected such that a different range of separation distances between the perforation points can be provided, such that when insertion needle 523b is inserted into the heart at a specified point, sharp distal tip 525b perforates the left ventricular wall at a roughly right angle and later perforates the septal wall at a roughly right angle as insertion needle 523b is further advanced. Curved hollow bore insertion needle 523c has a sharp distal tip 523c which is aligned with axis 524c, which is the central axis of proximal straight portion 526c. A distal portion of insertion of insertion needle 523c is curved so as to accommodate a third range of separation distances. The radius of curvature of the curved distal portion may be selected such that when insertion needle 523c is inserted into the heart at a specified point, sharp distal tip 525c perforates the left ventricular wall at a roughly right angle and later perforates the septal wall at a roughly right angle as insertion needle 523b is further advanced. The first, second, and third ranges allow reshaping (particular radius reduction) along the axis of the ventricle to be varied so as to provide a desired overall ventricle geometry, as can be further understood with reference to application Ser. No. 11/751,573, the full disclosure of which is incorporated herein by reference. Typical separation differences between perforation points may be pi times the difference in diameter between that of a dysfunctional heart and the same heart after a desired ventricular volume reduction. Exemplary differences in diameter range from about ½ to about 3 cm, resulting in differences in diameter from about 1.5 to about 10 cm, preferably about 4 cm to about 6 cm.

Figure 54A:
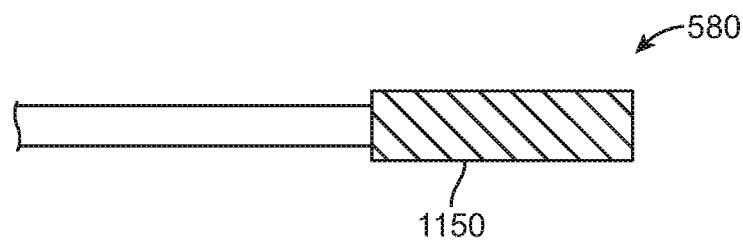
Figure 54B:
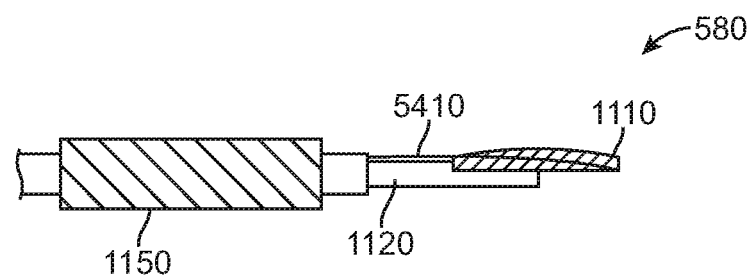
Figure 54C:
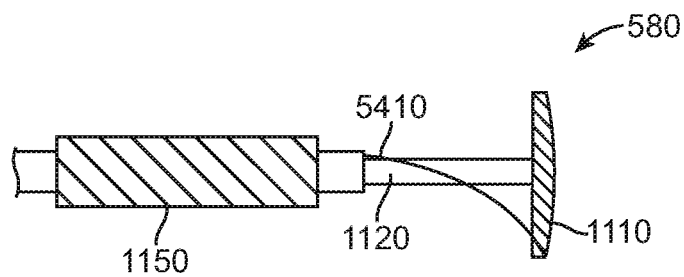

FIGS. 54a, 54b, and 54c show the distal or leading end of an anchor assembly 580. As shown in FIG. 54a, sheath 1150 can restrain anchor arm 1110. As shown in FIG. 54b, sheath 1150 may be retracted to expose anchor arm 1110. As described above, once anchor arm 1110 is free from the restraint of sheath 1150, anchor arm 1110 is free to be deployed as shown in FIG. 54c. In the deployed configuration, anchor arm 1110 is generally oblique or perpendicular to elongate member 1120. As shown in FIGS. 54b and 54c, anchor assembly 580 may further comprise a leash 5410 coupled to anchor arm 1110 and which can move anchor arm 1110 back to an undeployed configuration, i.e., generally parallel to elongate member 1120, after anchor arm 1110 has been deployed.

Referring now to FIG. 54d, optionally an inner tube 5412 may be advanced through introducer 560 (or another tubular delivery or access structure) to aid in retraction of the anchor. Leash 5410 can then pull arm 1110 inward toward an inner lumen of inner tube 5412. Even if the extreme end of arm 110 catches on the distal end of inner tube 5412, the inner tube and anchor can be safely retracted proximally together through the lumen of introducer 560.

Figure 55:
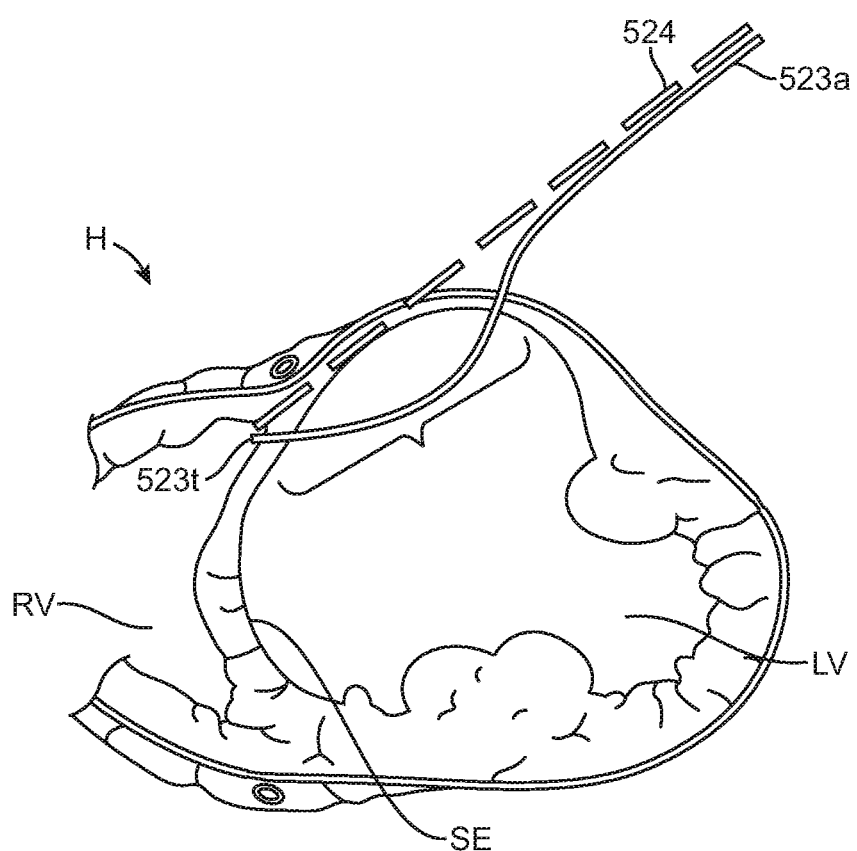
FIGS. 55-66 show a method of reducing the distance between opposed walls of a heart according to embodiments of the invention.
Figure 56:
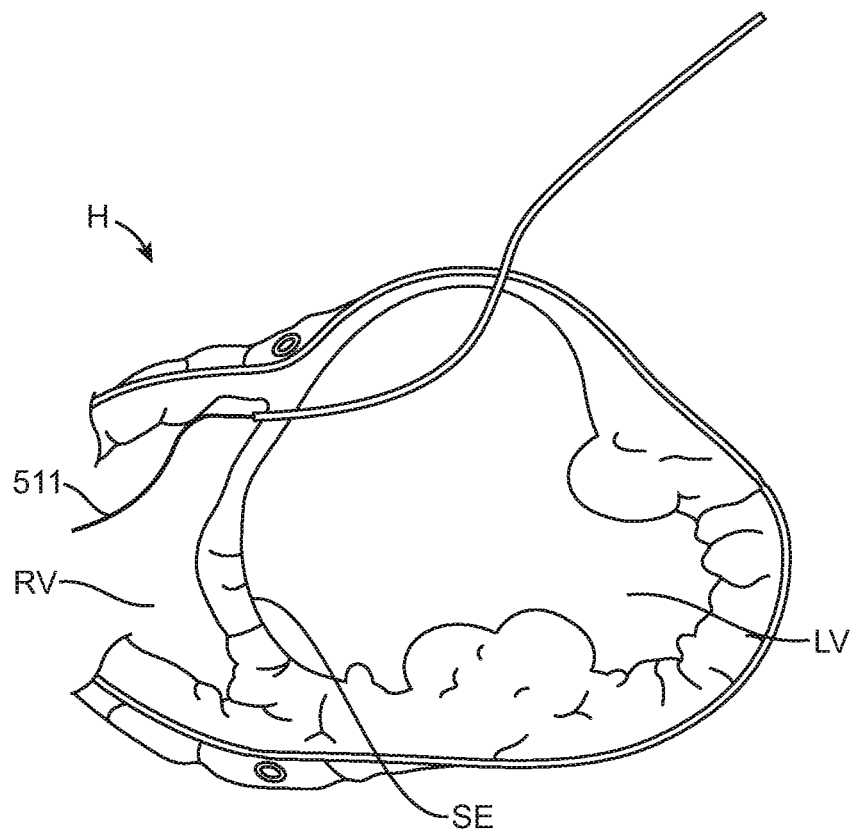
Figure 57:
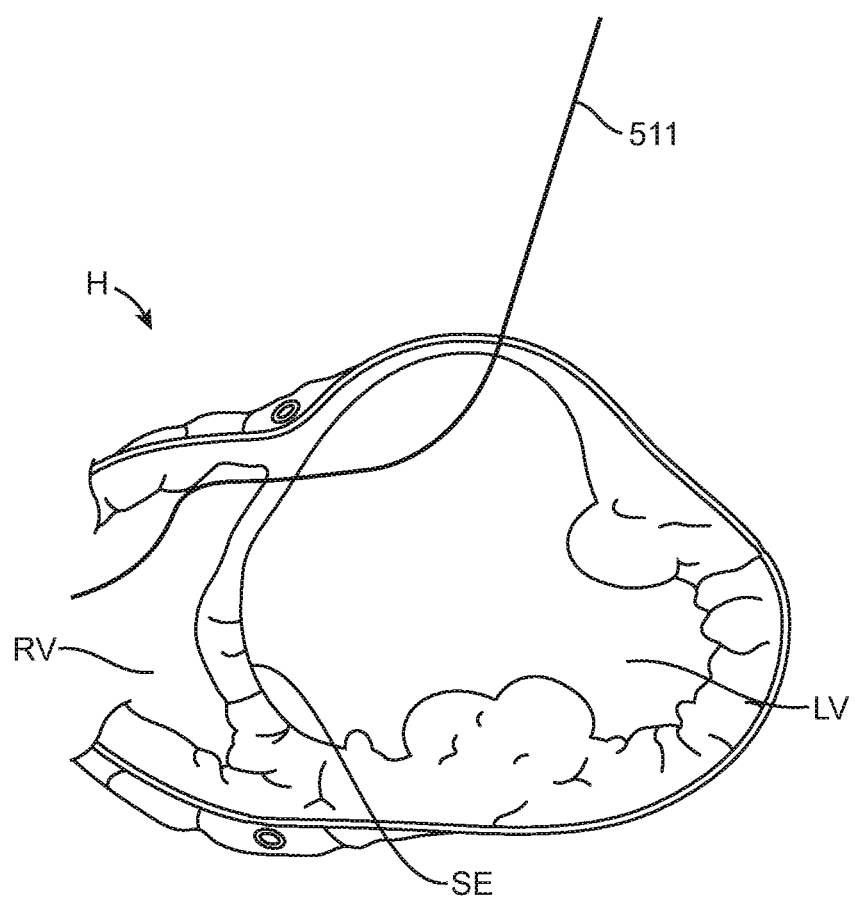
Figure 58:
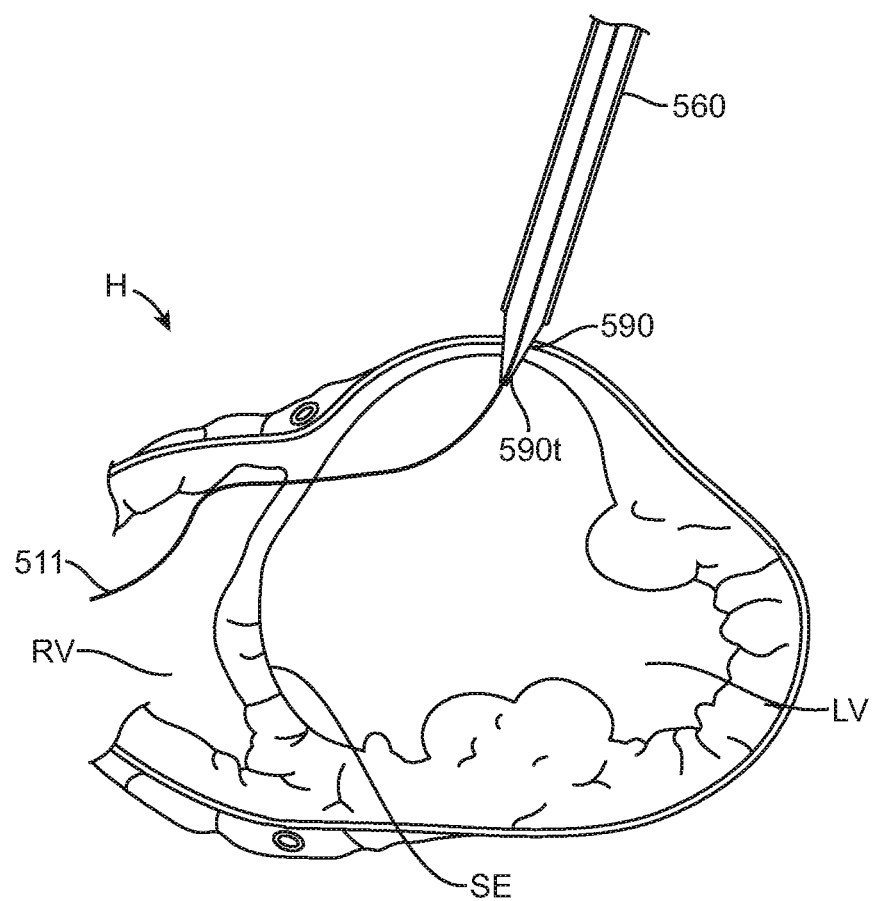

It should also be appreciated that systems for treating congestive heart failure according to embodiments of the invention may be used for methods which comprise different combinations and/or orders of different steps. FIGS. 55-66 show a method of using system 5300 to reduce the distance between two points in tissue wall. Method 5300 may be generally similar to method 2500 and method 500 described above. As shown in FIG. 55, curved hollow bore insertion needle or guidewire introducer 523a is threaded through the wall of left ventricle LV and septum SE such that the distal tip of needle 523a is in contact with the interior of the right ventricle RV. The distal tip 523t of needle 523a aligns with axis 524 of needle 523a so that the surgeon performing the method can use sight to properly orient needle 523a so the perforations made on the wall of left ventricle LV and septum SE are properly aligned. As shown in FIG. 56, guidewire 511 is threaded through the hollow center of curved hollow bore needle 523a into at least the right ventricle RV. As shown in FIG. 57, needle 523a has been removed, leaving guidewire 511 in place. As shown in FIG. 58, balloon introducer 560 is guided by guidewire 511 and is placed against the outer wall of left ventricle LV. Dilation member 590 is within balloon introducer 560. The distal end 590t of dilation member 590 is tapered. As balloon introducer 560 and dilation member 590 are advanced, the tapered end 590t dilates or expands the perforation made on the wall of the left ventricle LV. Dilation member 590 may be rotated to facilitate dilation of the tissue wall perforation.

Figure 59:
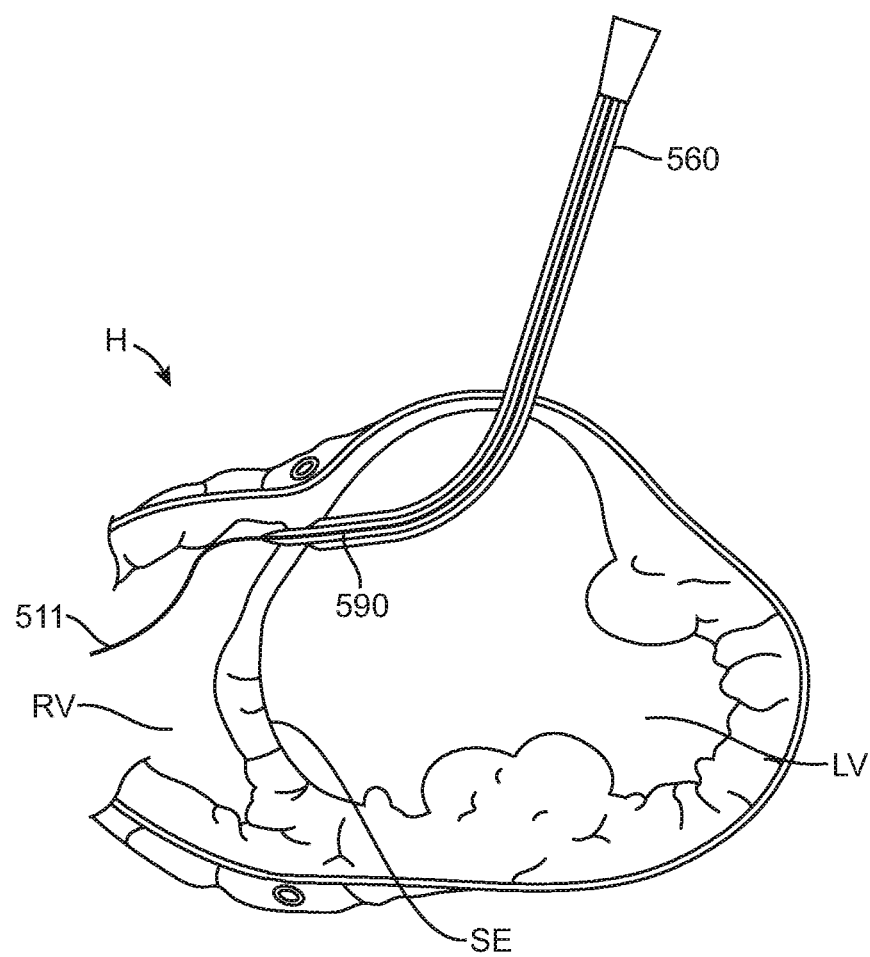
Figure 60:
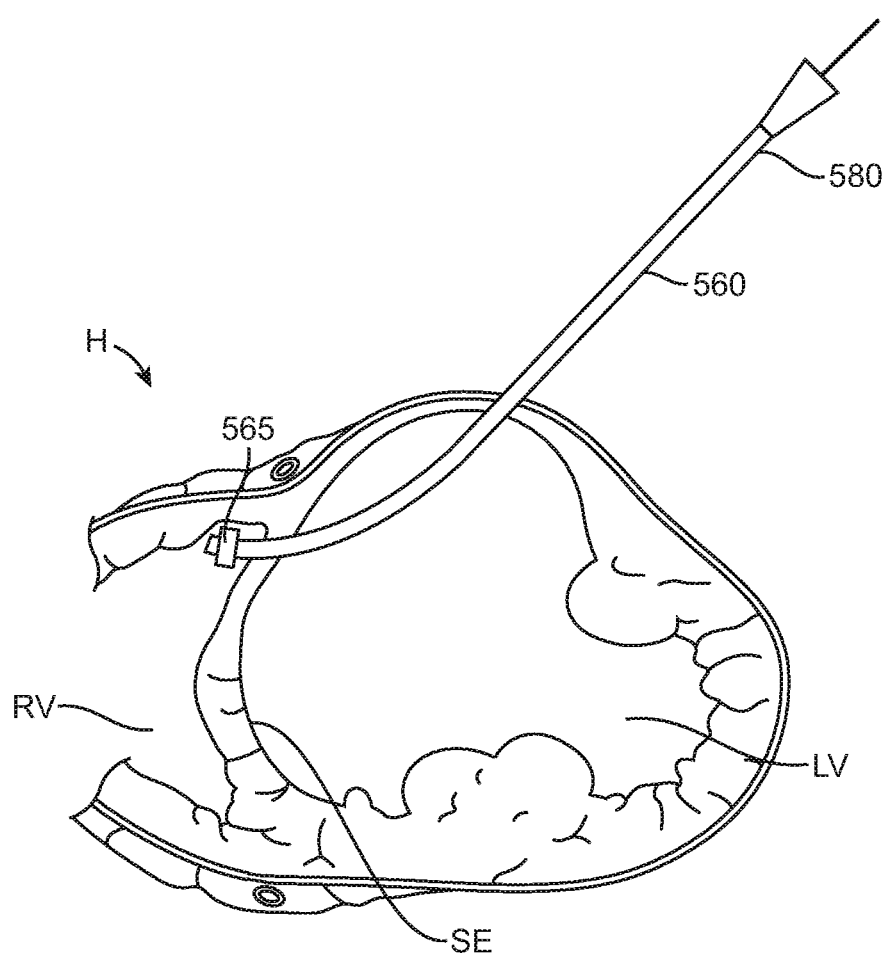
Figure 61:
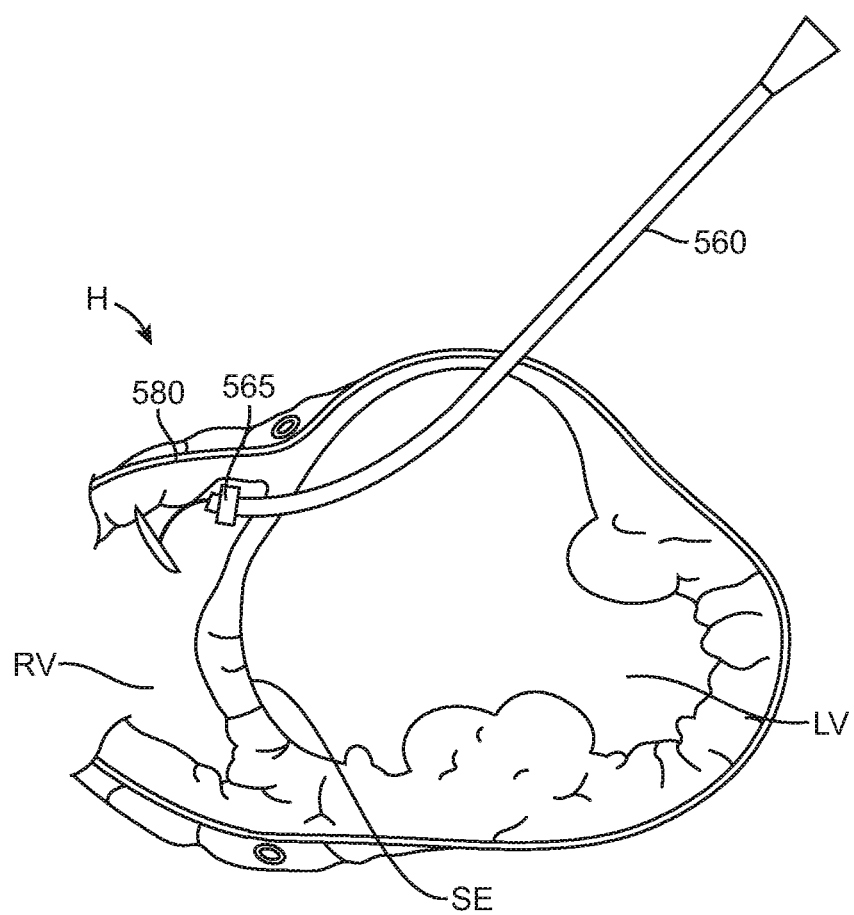
Figure 62:
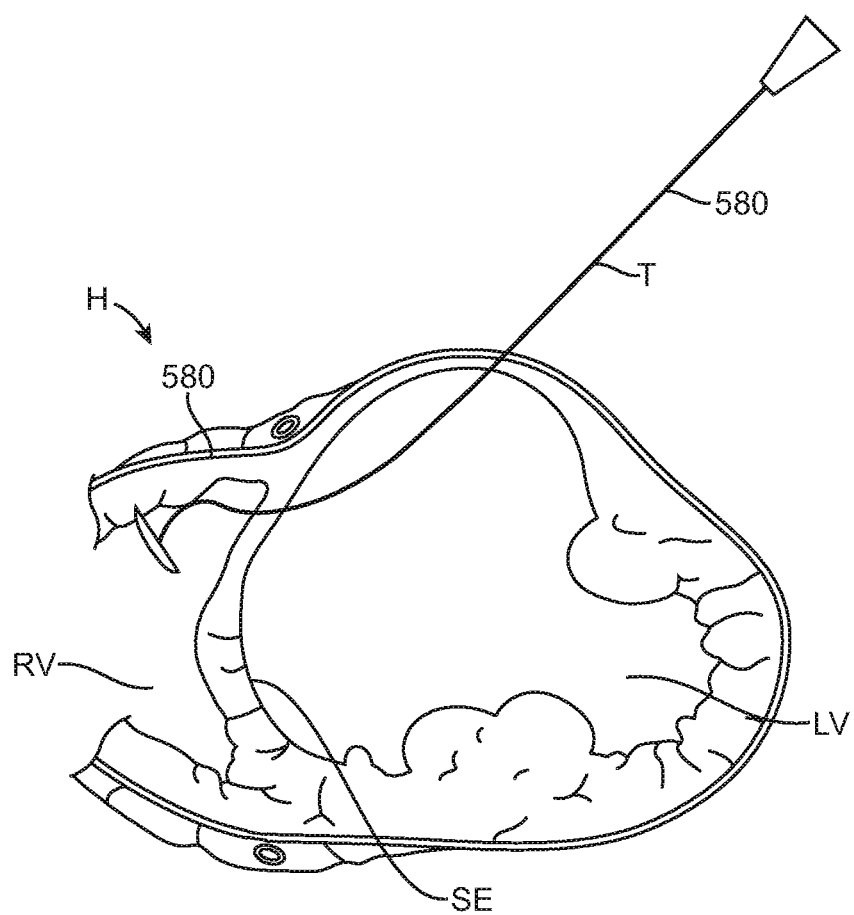
Figure 63:
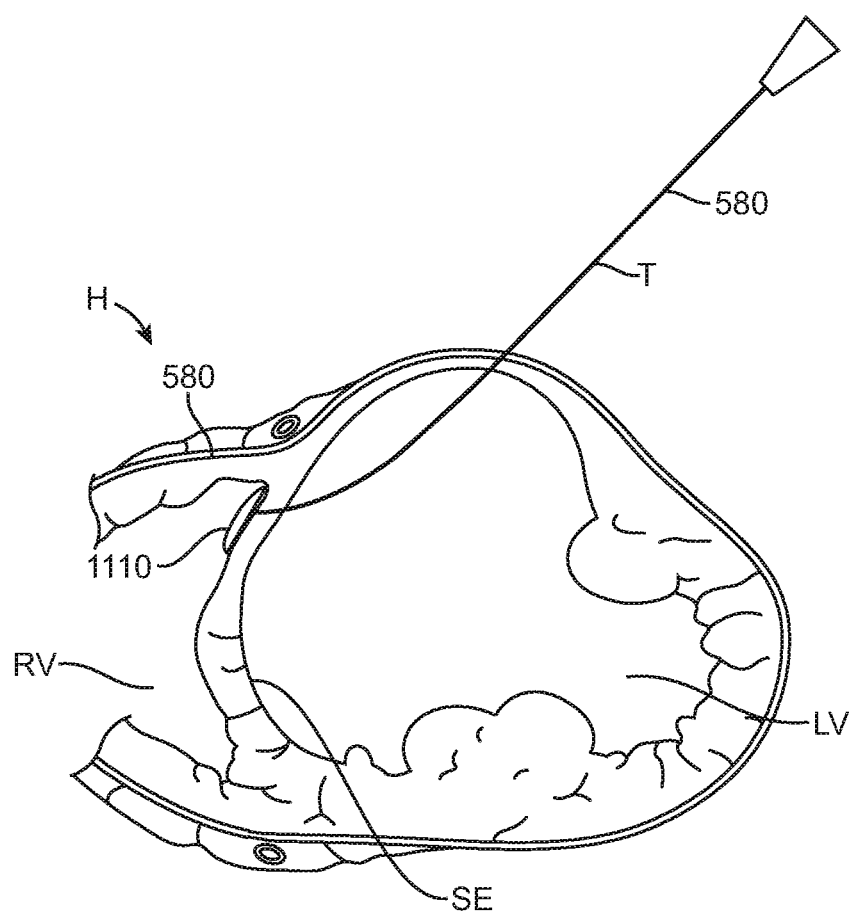
Figure 64:
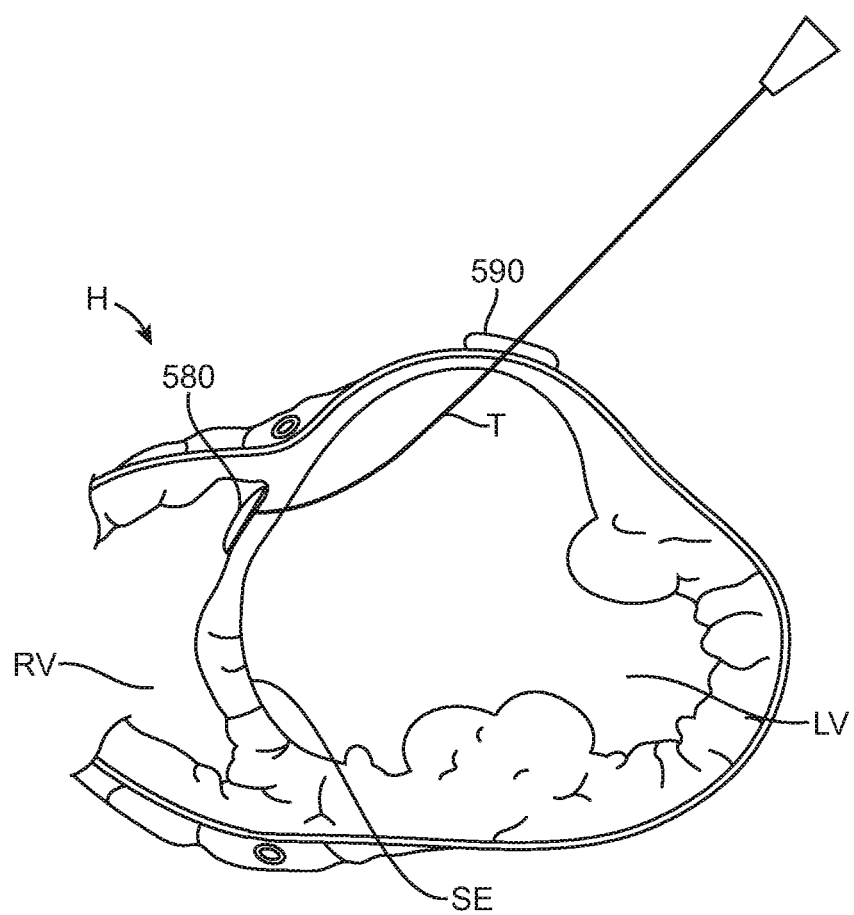
Figure 65:
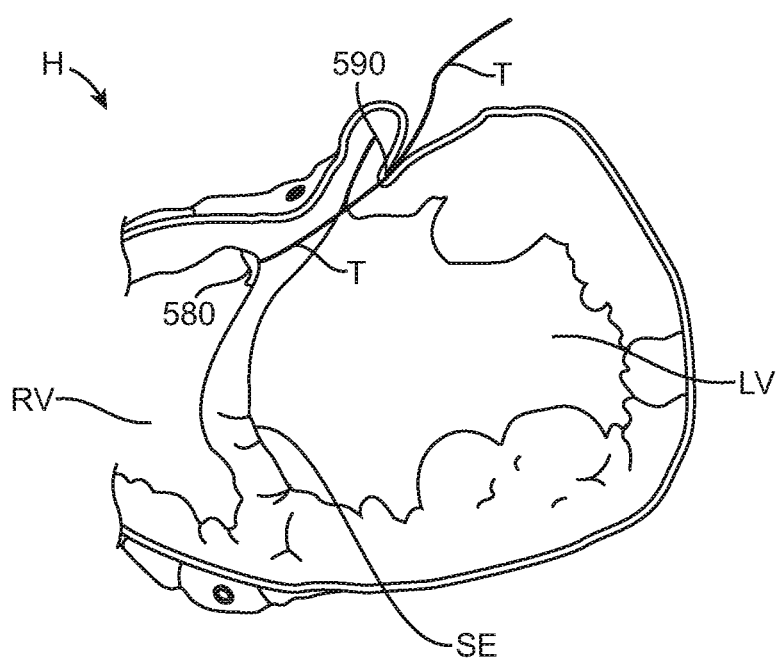
Figure 66:
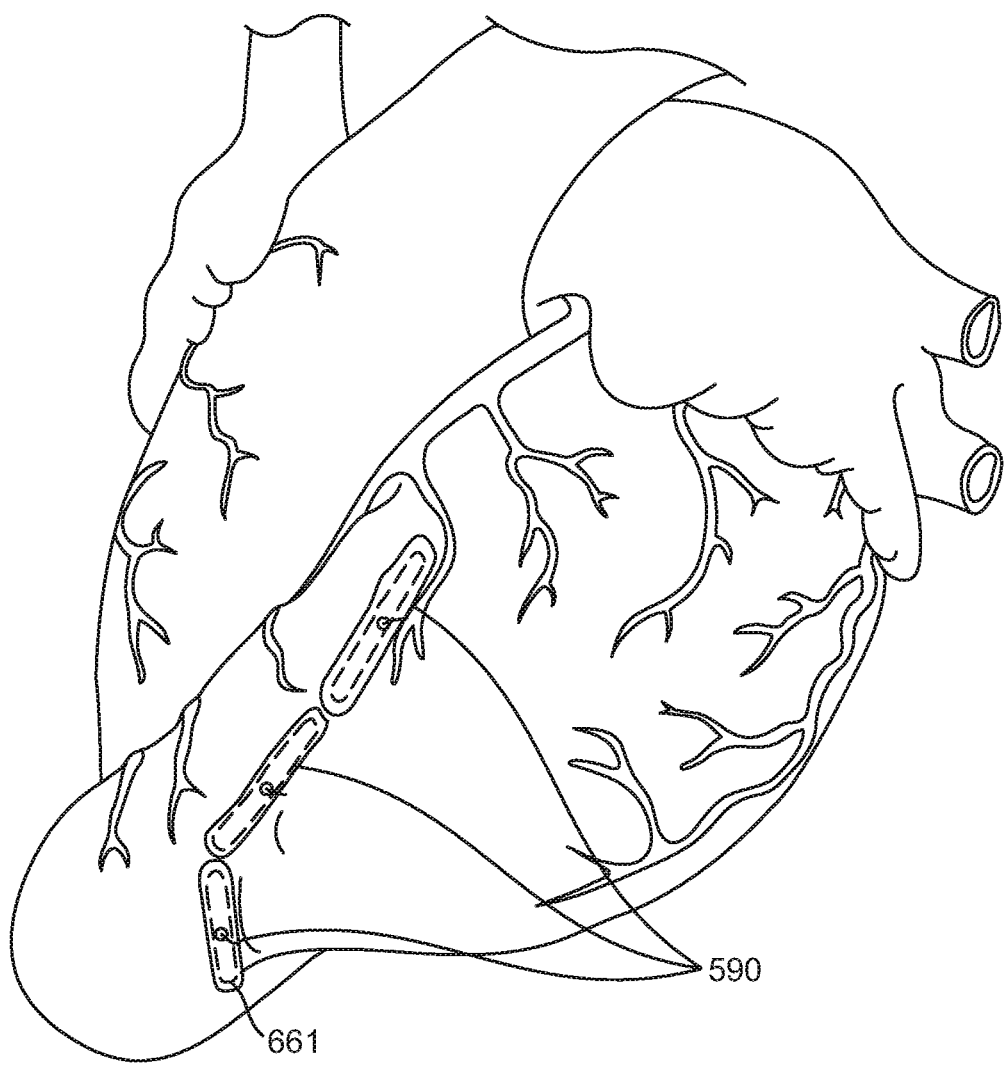

As shown in FIG. 59, balloon introducer 560 and dilation member 590 are further advanced. Dilation member 590 dilates or expands the perforation made of the wall of the septum SE. As shown in FIG. 60, balloon introducer 560 has been advanced so that expansion member 565 is within the right ventricle RV. Balloon introducer 560 is pulled proximally so that expansion member 565 urges against the wall of the septum SE. Dilation member 590 has been retracted and removed. In place of dilation member 590 is anchor assembly 580. Expansion member 565 is expanded. As shown in FIG. 61, anchor assembly 580 has been advanced and deployed in right ventricle RV. As shown in FIG. 62, expansion member 565 has been contracted or deflated and balloon introducer 560 has been proximally retracted. As shown in FIG. 63, tether T of anchor assembly 580 is pulled proximally so that arm 1110 urges against the wall of septum SE. As shown in FIG. 64, external anchor arm 590 is advanced over tether T. The steps described with reference to FIGS. 55-64 can be repeated, preferable at different, adjacent locations on heart H and with different guidewire introducers, for example, with any of curved hollow bore insertion needle 523b, curved hollow bore insertion needle 523c, and straight hollow bore insertion needle 521. As shown in FIG. 65, tether T and anchor assembly 560 have been pulled proximally while external anchor arm 590 is maintained in position, thereby reducing the distance between the walls of right ventricle RV and the septum SE and reconfiguring the geometry of the heart. In the cases in which multiple anchor pairs are used, the step described with reference to FIG. 65 can be performed after all of the steps described with reference to FIG. 55-64 have been performed for each of the anchor pairs, resulting in a heart H with reconfigured geometry as shown in FIG. 66. FIG. 66 also shows how alignment of anchor arms along a contour 661 can provide sealing of a portion of a ventrical and a beneficial remodeled chamber geometry.

It should be appreciated that the specific steps illustrated in FIG. 25, in FIGS. 27-45, and in FIGS. 55-66 provide particular methods of changing the geometry of a heart, according to embodiments of the invention. Other sequences of steps may also be performed according to alternative embodiments. For example, alternative embodiments of the invention may perform the steps outlined above in a different order. Moreover, the individual steps illustrated in FIG. 25, in FIGS. 27-45, and in FIGS. 55-66 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 67:
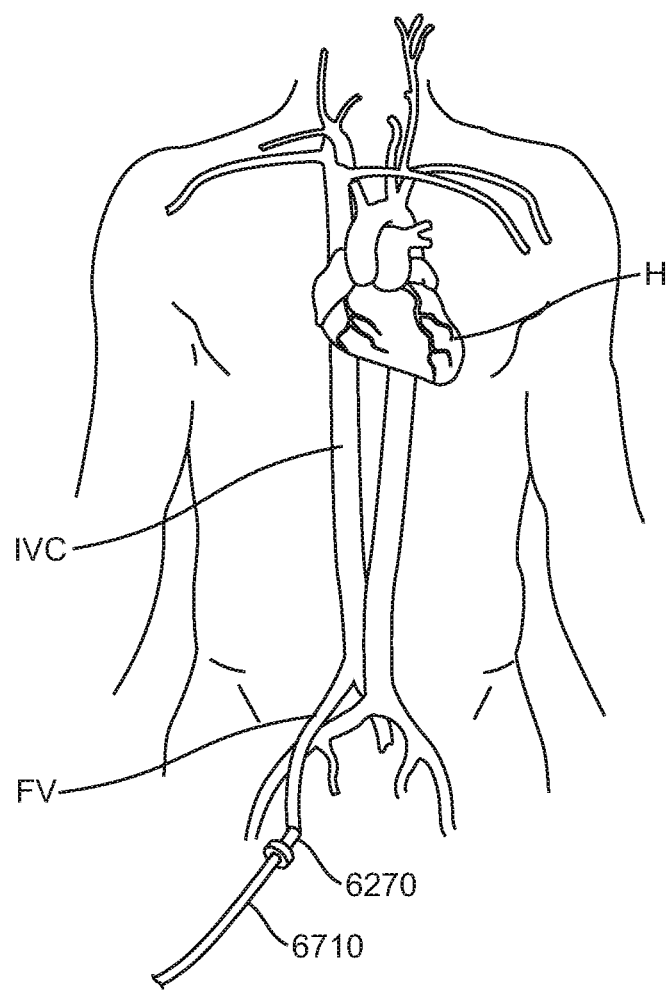

Embodiments of the invention also provide systems, device and methods by which the geometry of the heart is changed through a percutaneously performed procedure, which may be referred to as "percutaneous ventricular reduction" or PVR. FIGS. 67 to 93 show an exemplary PVR procedure using a catheter based system according to embodiments of the invention. As shown in FIG. 67, the femoral vein FV may be accessed for PVR procedures. An incision is made to access the femoral vein FV and a hemostasis valve 6720 is placed on the incision. A first catheter sheath 6710 is advanced through hemostasis valve 6720 and into the femoral vein FV. Alternatively, a PVR procedure may involve accessing the internal jugular vein in the neck.

Figure 68:
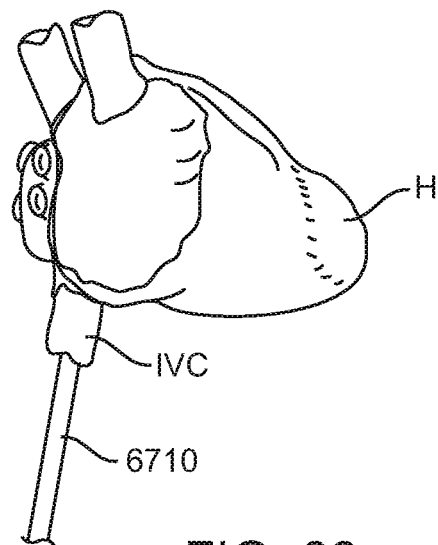
Figure 69:
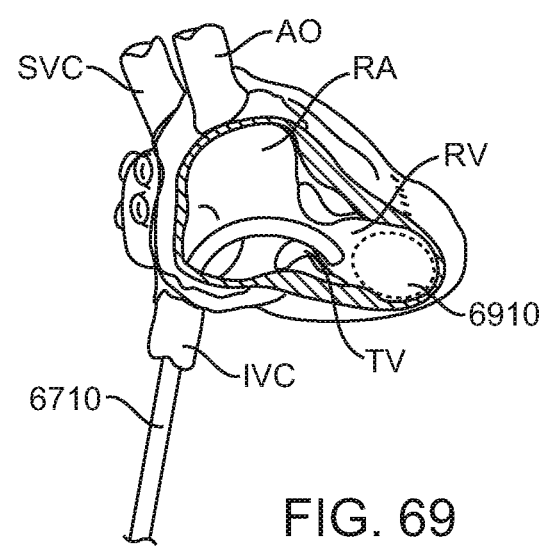

FIGS. 68 and 69 show first introducer or catheter sheath 6710 further advanced toward heart H, through the inferior vena cava IVC, right atrium RA, tricuspid valve TV, and into the right ventricle RV. FIG. 68 shows a perspective view of the heart H with catheter sheath 6710 advanced therein. FIG. 69 shows a cutaway perspective view of the heart H with catheter sheath 6710 advanced therein. As seen in FIG. 69, catheter sheath 6710 may be advanced adjacent to an unhealthy or dysfunctional area 6910 of the septum SE.

Figure 70:
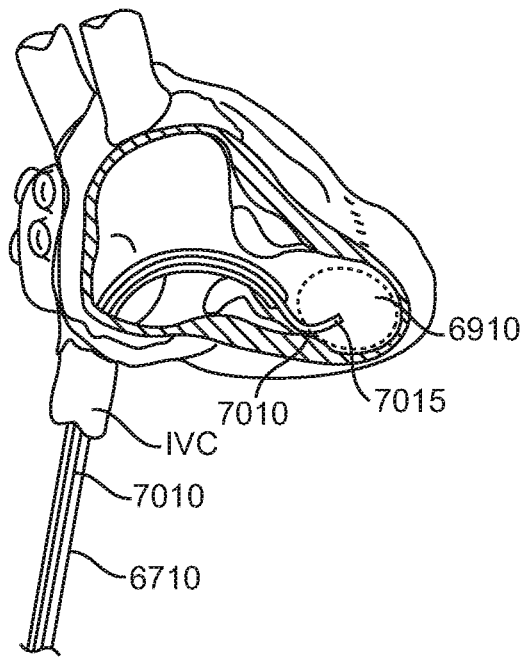

FIG. 70 shows a cutaway perspective view of heart H. A second introducer or catheter sheath 7010 is advanced through the lumen of first catheter sheath 6710. The distal portion 7015 of second catheter sheath 7010 has a curve, for example, a 90° curve, and is positioned so that it faces the dysfunctional area 6910 of the septum SE.

Figure 71:
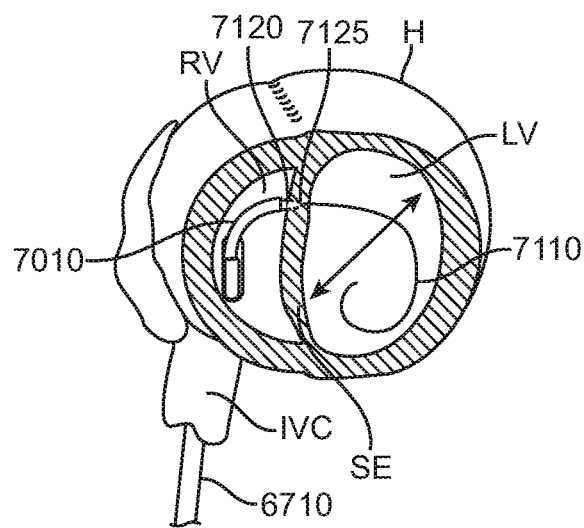

FIG. 71 shows a transverse cross-sectional or four-chamber view of heart H. A guidewire 7110 and a dilator 7120 are advanced through second catheter sheath 7010. Guidewire 7110 is used to perforate the septum SE, preferably the dysfunctional area 6910 of the septum SE, for example, by using radiofrequency (RF) energy. Guidewire 7110 is then advanced and coiled in the left ventricle LV. Dilator 7120 has a tapered distal end 7125.

Figure 72:
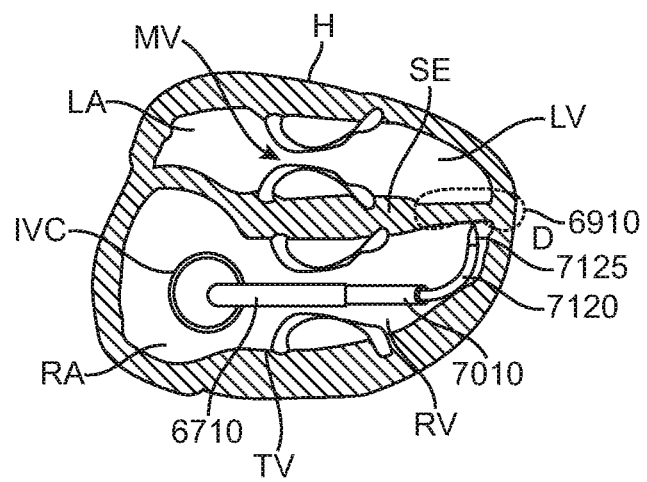

FIG. 72 shows a short axis cross-sectional view of the heart H, showing the left atrium LA, the mitral valve MV, the left ventricle LV, the septum SE, the right ventricle RV, the tricuspid valve TV, and the right atrium RA. FIG. 72 shows how first catheter sheath 6710, second catheter sheath 7010, dilator 7015, and tapered distal end 7125 may be positioned to guide guidewire 7110 through the dysfunctional area 6910 of the septum SE.

Figure 73:
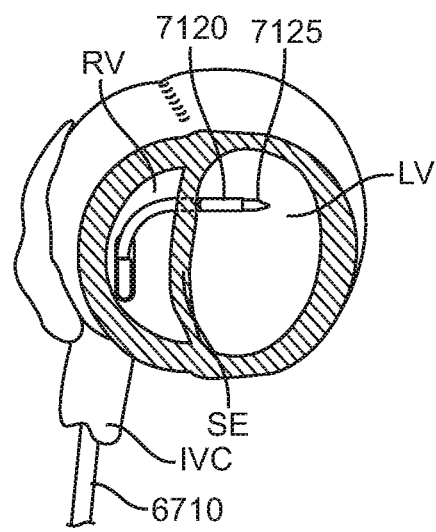

FIG. 73 shows a cross-sectional view of the heart H with dilator 7120 advanced through the septum SE and into the left ventricle LV through the perforation made by guidewire 7110.

Figure 74:
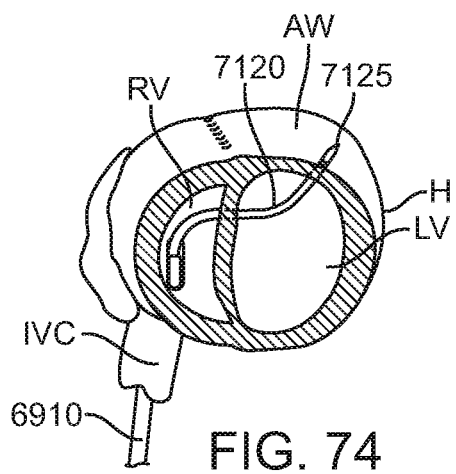
Figure 75:
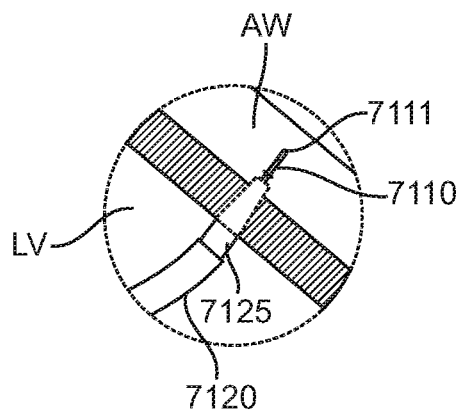
Figure 76:
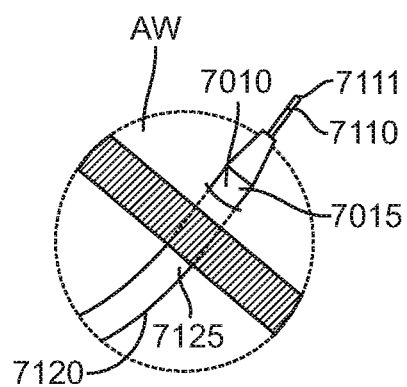

FIG. 74 shows a cross-sectional view of the heart H as dilator 7120 is advanced through the anterior wall of the left ventricle LV. FIGS. 75 and 76 shows a magnified view of distal end 7125 as dilator 7120 is advanced through the anterior wall of the left ventricle LV. Guidewire 7111 has a distal tip. Guidewire 7110 is used to perforate the anterior wall of the left ventricle LV, for example, by using radiofrequency (RF) energy. As shown in FIG. 76, after dilator 7110 has advanced through the anterior wall of the left ventricle LV, second catheter sheath 7010 is advanced through the anterior wall AW of left ventricle LV.

Figure 77:
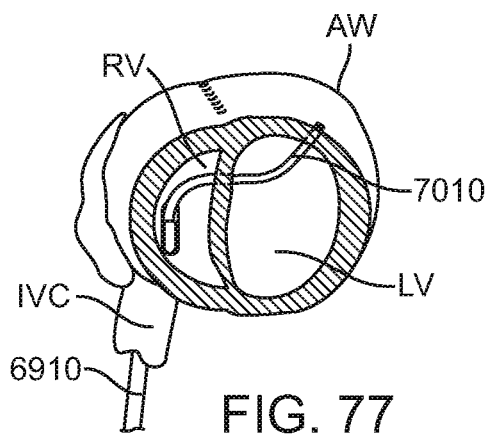
Figure 78:
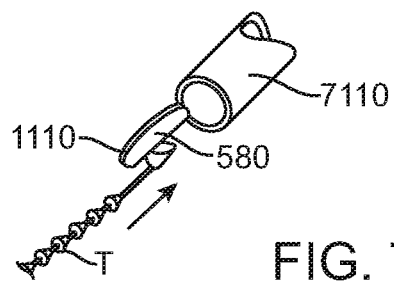

FIG. 77 shows a cross-sectional view of the heart H as guidewire 7110 and dilator 7120 are retrieved, leaving second catheter sheath 7010 through the anterior wall AW of the left ventricle LV. FIG. 78 shows an anchor assembly 580 loaded onto the proximal end of the second catheter sheath 7010. Anchor assembly 580 is then pushed to the distal end of the second catheter sheath 7010.

Figures 79, 80:
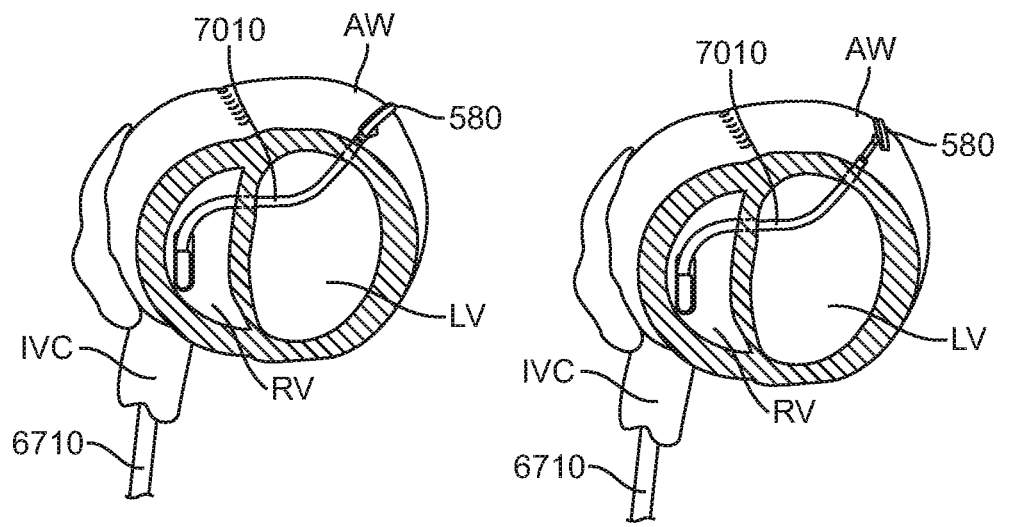
Figures 81, 82:
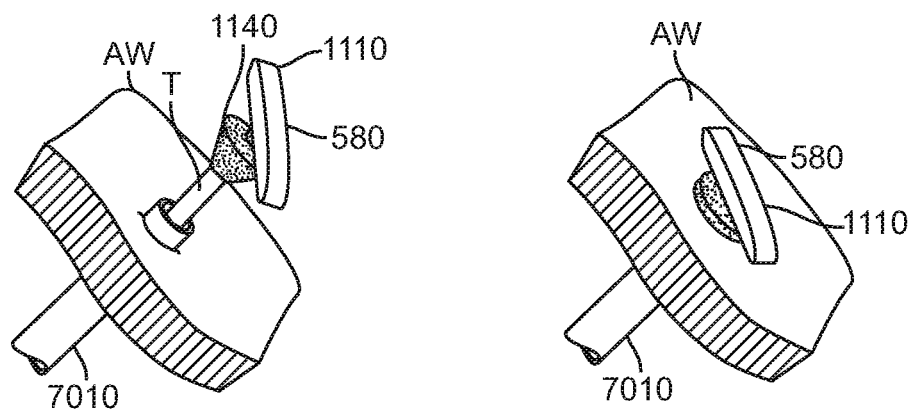
Figure 83:
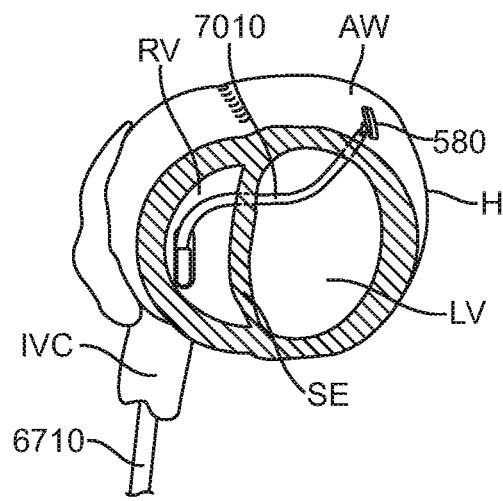

FIG. 79 shows a cross-sectional view of the heart H as anchor 580 is delivered to the epicardium of the anterior wall of left ventricle LV. As shown in FIG. 80, anchor assembly 580 is then aligned along the long axis of the heart. As shown in FIG. 81, a hemostatic plug 1140 can be delivered through the second catheter sheath 7010 over tether 10 against distal anchor arm body 1110 of anchor assembly 580. As shown in FIGS. 82 and 83, tension can then be applied to tether T to position distal anchor arm body 1110 against the epicardium.

Figure 84:
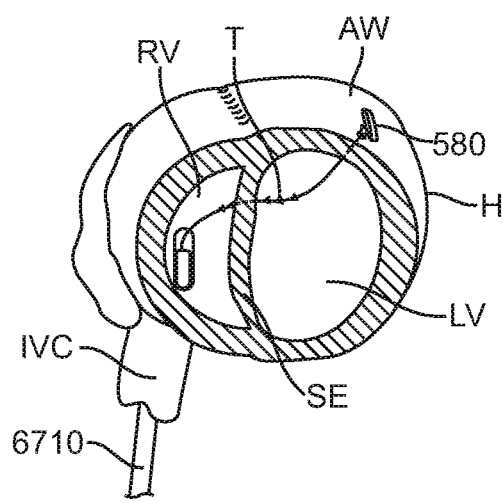
Figure 85:
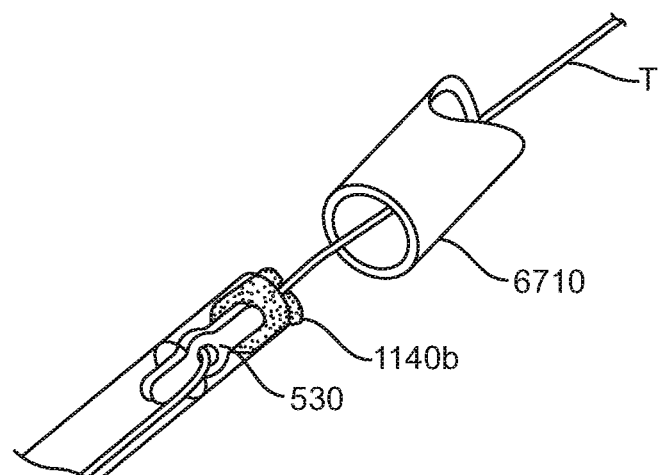
Figure 86:
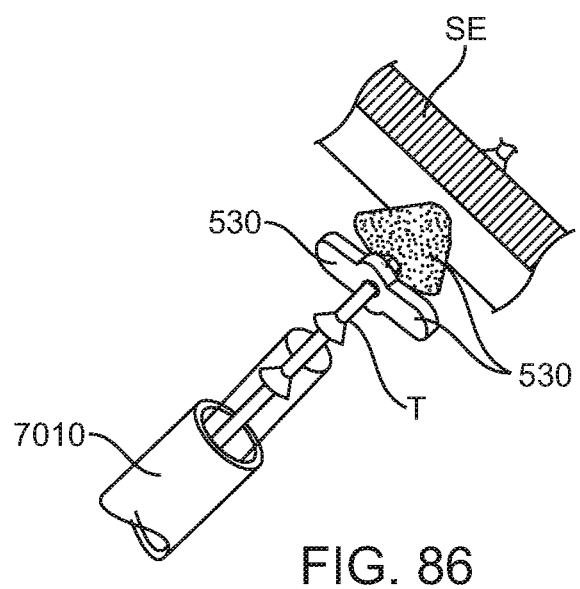

FIG. 84 shows a cross-sectional view of the heart H as second catheter sheath 7010 is retrieved. As shown in FIG. 85, septal or external anchor 530 and hemostatic plug 1140*b* are loaded into the proximal end of first catheter sheath 6170 over tether T of anchor assembly 580. As shown in FIGS. 86 and 87, septal anchor 530 and hemostatic plug 1140*b* are deployed against the septum SE in the right ventricle RV, for example, by means of a push catheter. As shown in FIGS. 88 and 89, a locking mechanism 8810 can be introduced through first catheter sheath 6710 and advanced against septal anchor 530.

Figure 91:
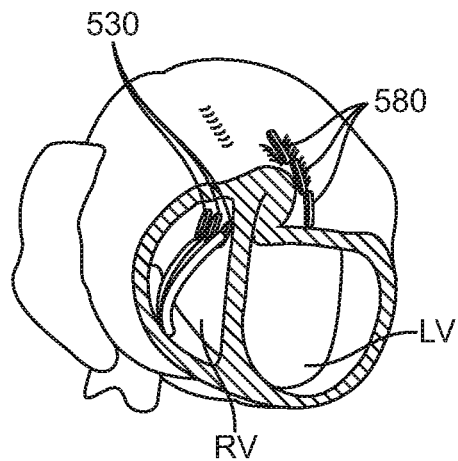
Figures 92, 93:
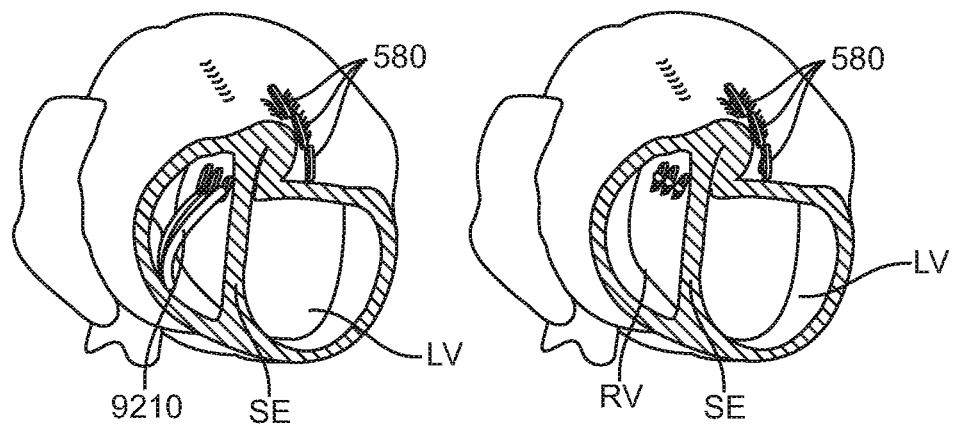

As shown in FIG. 90, the procedure can then be repeated a number of times with other sets of anchor assemblies 580 and septal anchors 530 being deployed along a pre-selected apposition line. As shown in FIG. 91, the sets of anchor assemblies 580 and septal anchors 530 are tightened to produce a cinching effect of the left ventricle LV, reducing its volume. Different sets of anchor assemblies 580 and septal anchors 530 may be alternately tightened. As shown in FIG. 92, a cutter 9210 can be advanced adjacent to a locking mechanism 8810 to cut a tether T of an anchor assembly 580. As shown in FIG. 93, with the tethers T cut from anchor assemblies 580, the procedure on the heart H is complete.

Figure 95:
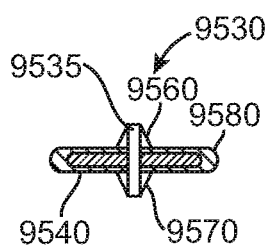
Figure 96:
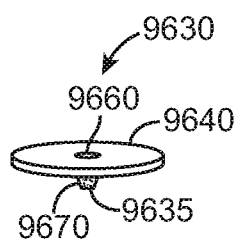
Figure 97:
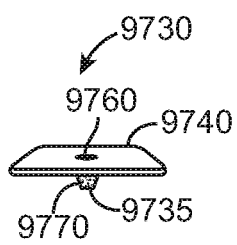
Figure 98:
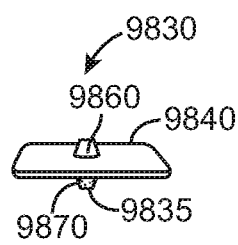
Figure 94:
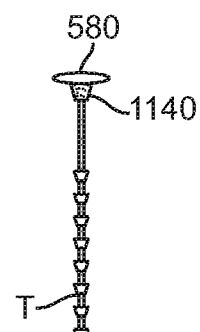

FIG. 94 shows an anchor assembly 580 having an external anchor 530 threaded over tether T. FIGS. 95-110 show embodiments of proximal or external anchors according to embodiments of the invention. These proximal or external anchors may be used with any of the methods described herein. FIG. 95 shows a proximal anchor 9530. Proximal anchor 9530 comprises a support body 9540 enveloped by fabric 9580. Proximal anchor 9530 further comprises an aperture 9535 through which proximal anchor 9530 can be advanced over a tether T of anchor assembly 530. Adjacent to aperture 9535 are a conic lock 9560 on the proximal side of support 9540 and a conic plug 9570 on the distal side of support body 9540. FIG. 96 shows a proximal anchor 9630. Proximal anchor 9630 comprises a circular support body 9640. Proximal anchor 9630 further comprises an aperture 9635 through which proximal anchor 9630 can be advanced over a tether T of anchor assembly 530. Adjacent to aperture 9635 are a lock 9660 on the proximal side of support 9640 and a conic plug 9670 on the distal side of support body 9640. FIG. 97 shows a proximal anchor 9730. Proximal anchor 9730 comprises a rectangular support body 9740. Proximal anchor 9730 further comprises an aperture 9735 through which proximal anchor 9730 can be advanced over a tether T of anchor assembly 530. Adjacent to aperture 9735 are a lock 9760 on the proximal side of support 9740 and a conic plug 9770 on the distal side of support body 9740. FIG. 98 shows a proximal anchor 9830. Proximal anchor 9830 comprises a rectangular support body 9840. Proximal anchor 9830 further comprises an aperture 9835 through which proximal anchor 9830 can be advanced over a tether T of anchor assembly 530. Adjacent to aperture 9835 are a lock 9860 on the proximal side of support 9840 and a conic plug 9870 on the distal side of support body 9840.

Figures 99, 100:
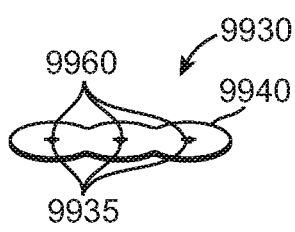
Figure 101:
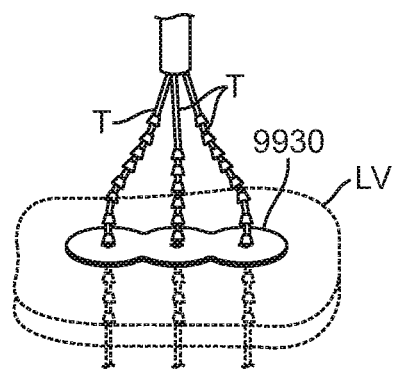
Figure 102:
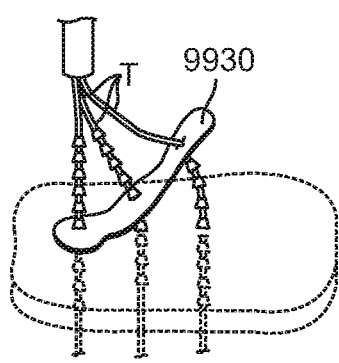

FIGS. 99-102 show a proximal anchor 9930. FIG. 99 shows the proximal side of proximal anchor 9930 while FIG. 100 shows the distal side of proximal anchor 9930. Proximal anchor 9930 comprises a curved, elongate support body 9940 having a plurality of apertures 9935 through which proximal anchor 9930 can be advanced over tethers T of anchors assemblies as shown in FIGS. 101 and 102. Although three apertures 9935 are shown, other numbers of apertures are conceivable.

FIGS. 103 to 110 show a proximal anchor assembly 10300 and a method of securing proximal anchor assembly 10300 adjacent the heart. Proximal anchor assembly 10300 comprises a middle anchor portion 10310, a first side anchor portion 10310*a*, and a second side anchor portion 10310*b*. FIG. 103 shows the proximal side of middle anchor portion 10310. Middle anchor portion 10310 comprises an aperture 10335 through which middle anchor portion 10310 can be threaded over a tether T of an anchor assembly 530 as shown in FIG. 104. A lock 10360 is disposed adjacent to aperture 10335 on the proximal side of middle anchor portion 10310. Middle anchor portion 10310 further comprises a first side adhesive portion 10390*a* and a second side adhesive portion 10390*b*. FIG. 103 shows the distal side of first side anchor portion 10310*a*. First side anchor portion 10310*a* comprises an aperture 10335 through which first side anchor portion 10310*a* can be threaded over a tether T of an anchor assembly 530. A conic plug 10370 is disposed adjacent to aperture 10335 on the distal side of first side anchor portion 10390*a*. First side anchor portion 10310*a* further comprises an adhesive portion 10391*a* which can adhere to side adhesive portion 10390*a* of middle anchor portion 10310 as shown in FIG. 106. FIG. 103 shows the distal side of second side anchor portion 10310*b*. Second side anchor portion 10310*b* comprises an aperture 10335 through which second side anchor portion 10310*b* can be threaded over a tether T of an anchor assembly 530. A conic plug 10370 is disposed adjacent to aperture 10335 on the distal side of second side anchor portion 10390*b*. Second side anchor portion further comprises an adhesive portion 10391*b* which can adhere to side adhesive portion 10390*b* of middle anchor portion 10310 as shown in FIG. 106. To secure proximal anchor assembly 10300, middle anchor portion 10310 is first advanced over tether T of an anchor assembly 580 disposed between two adjacent anchor assemblies 580 as shown in FIG. 104. As shown in FIG. 105, first side anchor portion 10310*a* and second side anchor portion 10310*b* are then advanced over the tethers T of the adjacent anchor assemblies 580. As seen in FIG. 103, adhesive portion 10391*a* of first side anchor portion 10310*a* adheres with first adhesive side portion 10390*a* of middle anchor portion 10310, adhesive portion 10391*b* of second side anchor portion 10310*b* adheres with second adhesive side portion 10390*b* of middle anchor portion 10310, and tethers T can then be cut.

Figure 107:
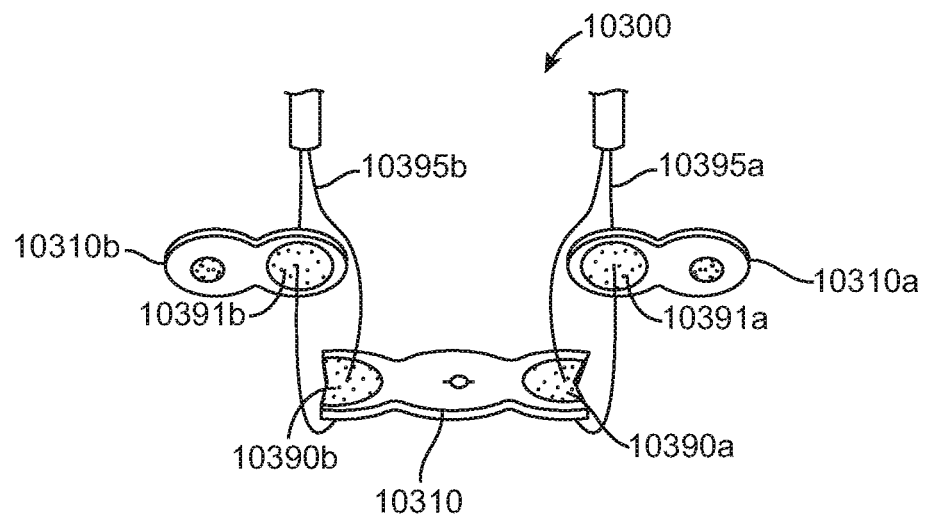
Figure 108:
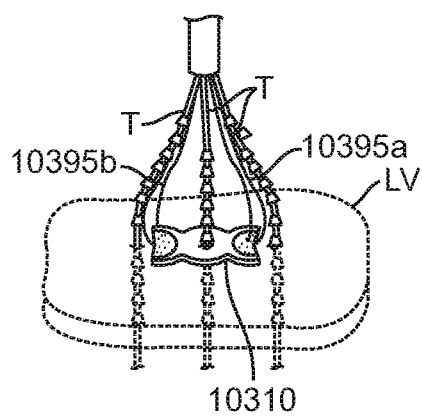
Figure 109:
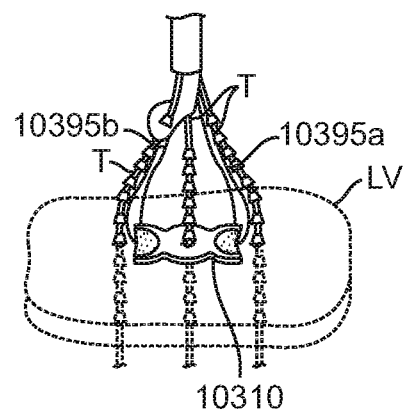
Figure 110:
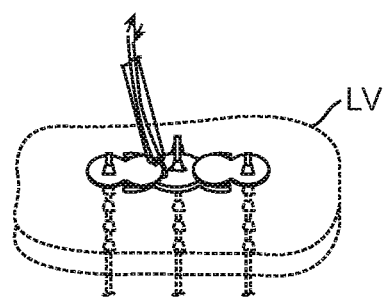

As shown in FIGS. 107-110, adhering middle anchor portion 10310 with first side anchor portion 10310*a* and second side anchor portion 10310*b* can be assisted with a first thread 10395*a* and a second thread 10395*b*. As shown in FIG. 107, first thread 10395*a* traverses first side adhesive portion 10390*a* of middle anchor portion 10310 and side adhesive portion 10390*a* of first side anchor portion 10310*a*, and second thread 10395*b* traverses second adhesive portion 10390*b* of middle anchor portion 10310 and side adhesive portion 10390*b* of second side anchor portion 10310*b*. As shown in FIGS. 108 and 109, first thread 10395*a* and second thread 10395*b* can restrict the rotation of first side anchor portion 10310*a* and second side anchor portion 10310*b*, respectively, so that adhesive portion 10391*a* of first side anchor portion 10310*a* meets first adhesive side portion 10390*a* of middle anchor portion 10310 when first side anchor portion 10310*a* is advanced, and so that adhesive portion 10391*a* of second side anchor portion 10310*b* meets second adhesive side portion 10390*b* of middle anchor portion 10310 when second side anchor portion 10310*b* is advanced. As shown in FIG. 110, tethers T, first thread 10395*a* and second thread 10395*b* can then be cut.

FIGS. 111, 112A, 112B, 113A, 113B, 114A, 114B, 114C, 115A, 115B, 116A, 116B, 117A, 117B, 117C, 118A, 118B, 118C, 118D, 119A, 119B, and 119C show additional exemplary embodiments of the distal portion of an anchor assembly according to embodiments of the invention, for example, anchor assembly 580.

FIGS. 111-112B show leading end 11200. Leading end 11200 comprises a superelastic wire 11205 with a shaped distal end 11250 enveloped by a sheath 11210. Superelastic wire 11205 may comprise a Nitinol wire. As shown by FIG. 111, shaped distal end 11250 can be constrained, for example, by sheath 1150. When no longer constrained, as in FIGS. 112A and 112B, shaped distal end 11250 can expand to an expanded, deployed form.

Figure 113A:
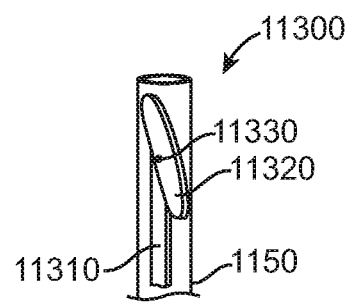
Figure 113B:
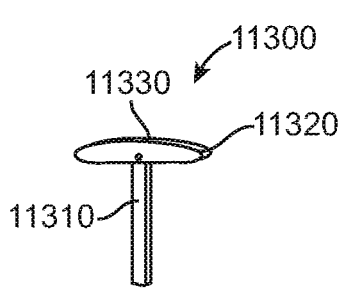
Figure 114A:
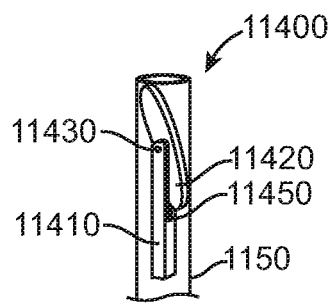
Figure 114B:
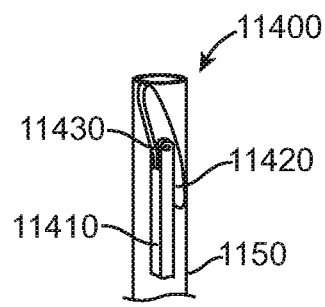
Figure 114C:
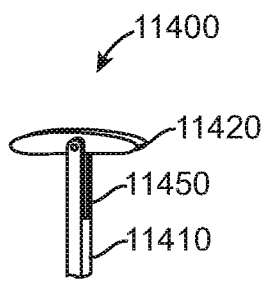
Figure 115A:
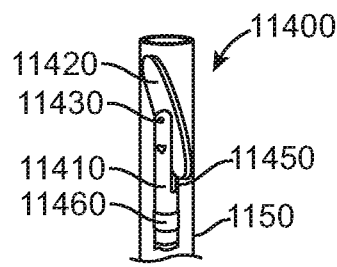
Figure 115B:
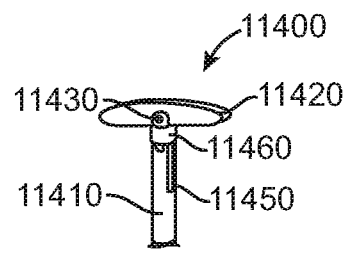
Figure 116A:
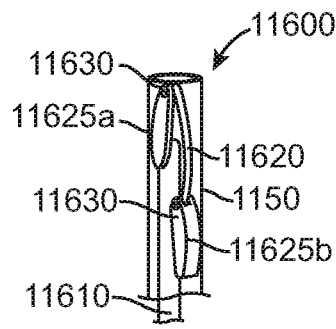
Figure 116B:
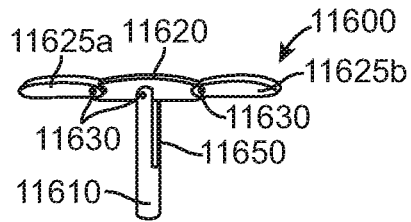

FIGS. 113A to 116B show exemplary embodiments of the distal arm of an anchor having articulated hinges. As shown in FIGS. 113A and 113B, a leading end 11300 comprises an elongate shaft 11310 coupled to a distal arm 11320 through an articulated hinge 11330. FIGS. 114A-114C, show a leading end 11400. Leading end 11400 comprises an elongate shaft 11410 coupled to a distal arm 11420 through an articulated hinge 11430. When constrained, for example, by sheath 1150, a portion of distal arm 11420 may fit into a recessed portion 11450 of elongate shaft 11410. As shown in FIGS. 115A and 115B, leading end 11400 may further comprise a locking mechanism 11460 which can be distally advanced to secure leading end 11400 in a deployed configuration as shown in FIG. 115B. As shown in FIGS. 116A and 116B, a leading end 11600 may comprise multiple distal arm segments. A central distal arm segment 11620 is coupled to an elongate shaft 11610 through an articulated hinge 11630. Central distal arm segment 11620 can fit into a recessed portion 11650 of elongate shaft 11610 when leading end 11600 is constrained, for example, by sheath 1150 as shown in FIG. 116A. Central distal arm segment 11620 is coupled to a first side arm segment 11620*a* and a second side arm segment 11620*b* through articulated hinges 11630. The articulated hinges 11630 may be biased so that central arm segment 11620, first side arm segment 11620*a*, and second side arm segment 11620*b* are each unfurled perpendicular to elongate shaft 11610 when deployed or no longer constrained, for example, by sheath 1150.

FIGS. 117A-117C show another exemplary anchor assembly leading end 11700. Leading end 11700 comprises a leading end or distal tip 11705 and a malecot 11710. Malecot 11710 is expanded to deploy leading end 11700. Malecot 11710 may be expanded, for example, by proximally retracting elongate shaft 11720 which is disposed within malecot 11710 and may be connected to distal top 11705. Malecot 11710 may be made of a metal, for example Nitinol, or plastic. Malecot 11710 may be covered or enveloped by a fabric.

FIGS. 118A-118D show another exemplary anchor assembly leading end 11800. Leading end 11800 comprises an elongate shaft 11810 coupled to an umbrella 11830. Umbrella 11830 comprises a plurality of bendable spines 11832 and fabric 11836 held together with stitching 11838. Umbrella 11830 can be constrained into an undeployed from, for example, by sheath 1150, as shown in FIGS. 118A and 118B. Bendable spines 11832 of umbrella 11830 are biased to deploy umbrella 11830 when no longer constrained as shown in FIGS. 118C and 118D. Fabric 11836 can have a set circumference so that fabric 11836 holds spines 11832 rigidly to keep umbrella 11830 from prolapsing.

FIGS. 119A-119C show another exemplary anchor assembly leading end 11900. Leading end 11900 comprises elongate shaft 11910 coupled to a plurality of segments 11920. Segments 11920 are linked by articulated hinges 11930. Elongate shaft 11910 is coupled to segments 11920 through a distal segment 11940. When elongate shaft 11910 is proximally retracted while segments 11920 are held in place, segments 11920 may flatten relative to one another to place leading end 11900 in an expanded state.

Figure 120A:
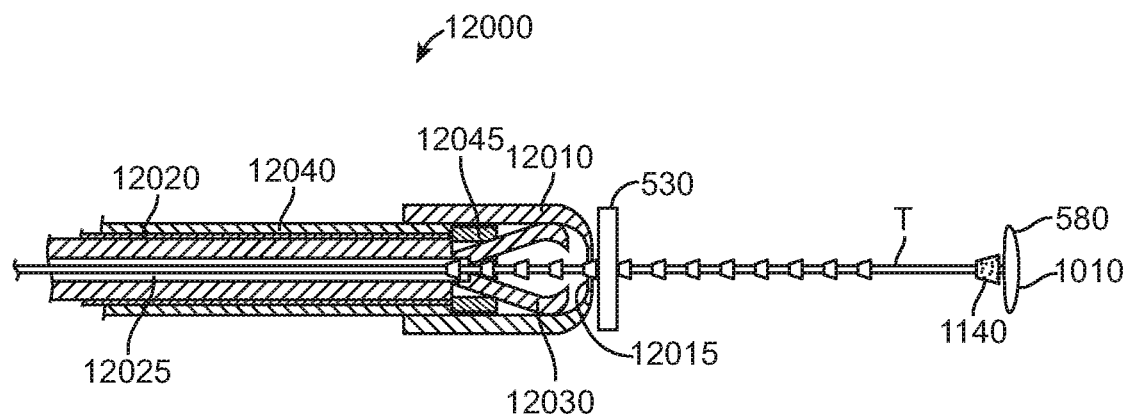
FIGS. 120A-122C show exemplary tether cutting mechanisms according to embodiments of the invention.
Figure 120B:
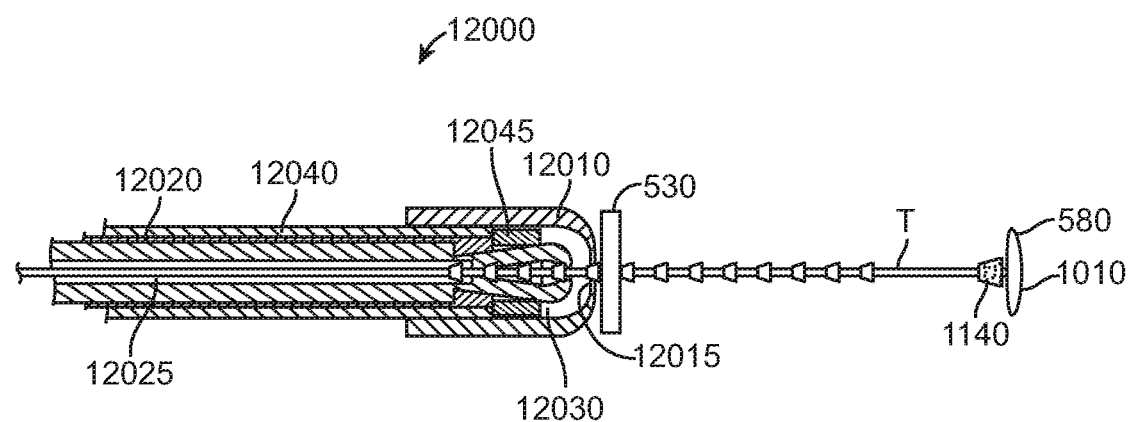

FIGS. 120A and 120B show an exemplary "nail clipper" cutting mechanism or clipper 12000 which can be used to cut tethers T of anchor assemblies 580. Clipper 12000 comprises a distal cap 12010, a tension shaft 12020, snippers 12030, and a compression shaft 12040. As shown in FIG. 120A, distal cap 12010 can be advanced over tether T through an aperture 12015 until adjacent to external anchor 530, and tension shaft 12020 and compression shaft 12040 can be advanced over tether T through a lumen 12025 of tension shaft 12020 until adjacent to external anchor 530. Tension shaft 12020 can fit into the lumen of compression shaft 12040. The distal end of tension shaft 12020 is coupled to snippers 12030. Snippers 12030 comprises a pair of jaws which may be adapted to splay outward. As shown in FIG. 120B, by holding tension shaft 12020 in place and distally advancing compression shaft 12040, compression ring 12045 disposed on the distal end of compression shaft 12040 can press the jaws of snippers 12030 together, cutting tether T.

Figure 121A:
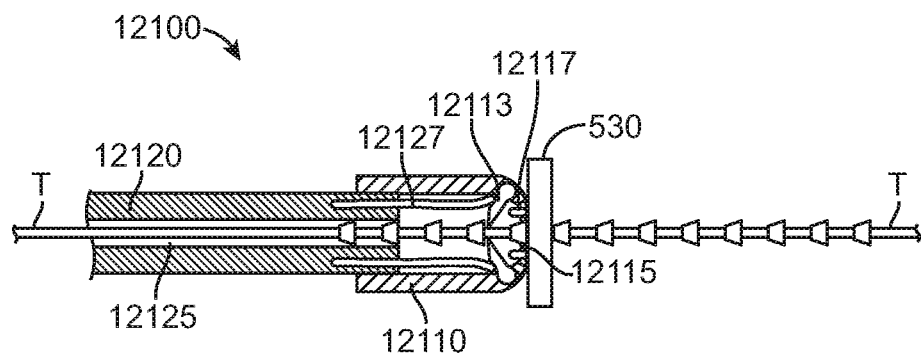
Figure 121B:
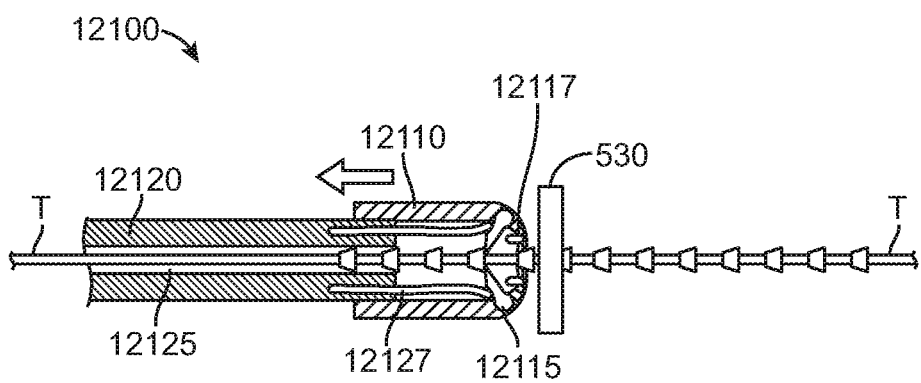

FIGS. 121A and 121B show an exemplary dual blade cutting mechanism 12100 which can be used to cut tethers T of anchor assemblies 580. Cutting mechanism 12100 comprises a distal cap 12110 coupled to the distal end of a shaft 12120. As shown in FIG. 121A, distal cap 12110 can be advanced over tether T through an aperture 12115 until adjacent to external anchor 530, and shaft 12120 can be advanced over tether T through a lumen 12125 of shaft 12120. Distal cap 12110 comprises blades 12113 which are oriented toward tether T and are disposed proximal of stops 12117. Shaft 12120 comprises distal arms 12127 facing distally toward blades 12113. As shown in FIG. 121B, when distal cap 12110 is retracted proximally, distal arms 12127 of shaft 12120 can push blades 12113 toward tether T and cut tether T. Stops 12117 can prevent blades 12113 from being pushed too distally.

Figure 122A:
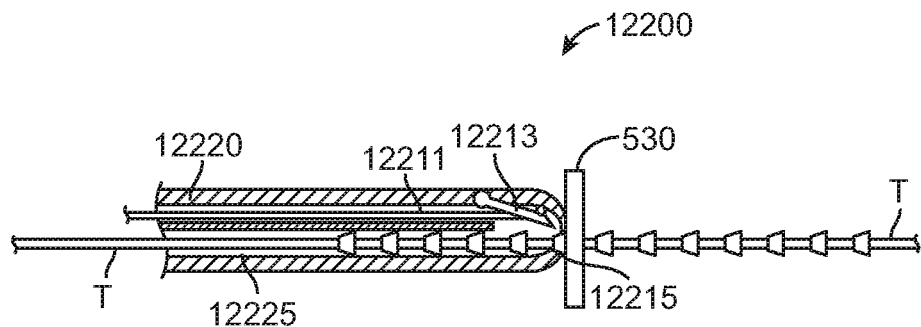
Figure 122B:
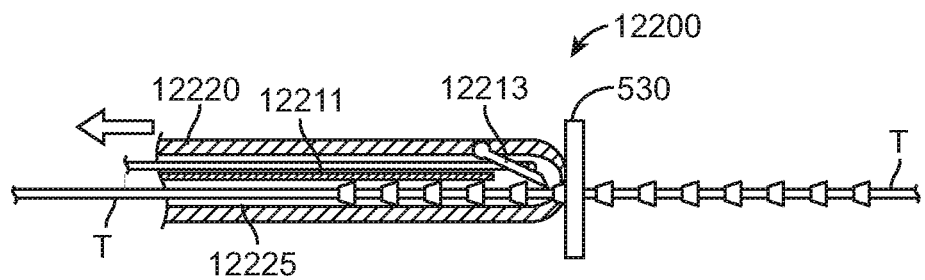
Figure 122C:
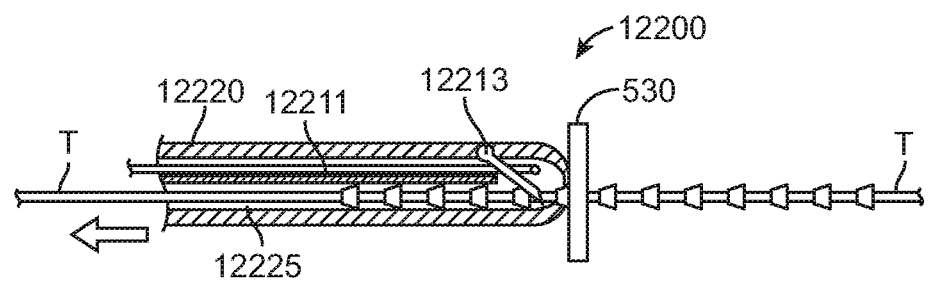

FIGS. 122A-122C show an exemplary single blade cutting mechanism 12200 which can be used to cut tethers T of anchor assemblies 580. Cutting mechanism 12200 comprises a shaft 12220 having a lumen 12225 and a distal aperture 12215 through which cutting mechanism 12200 can be advanced over tether T. Disposed within lumen 12225 are a blade 12213 coupled to an activation wire 12211. Blade 12213 is oriented toward the tether T. As shown in FIGS. 122B and 122C, activation wire 12211 can be retracted, thus actuating blade 12213 toward tether T and cutting tether T.

Figures 123A, 123B, 123C:
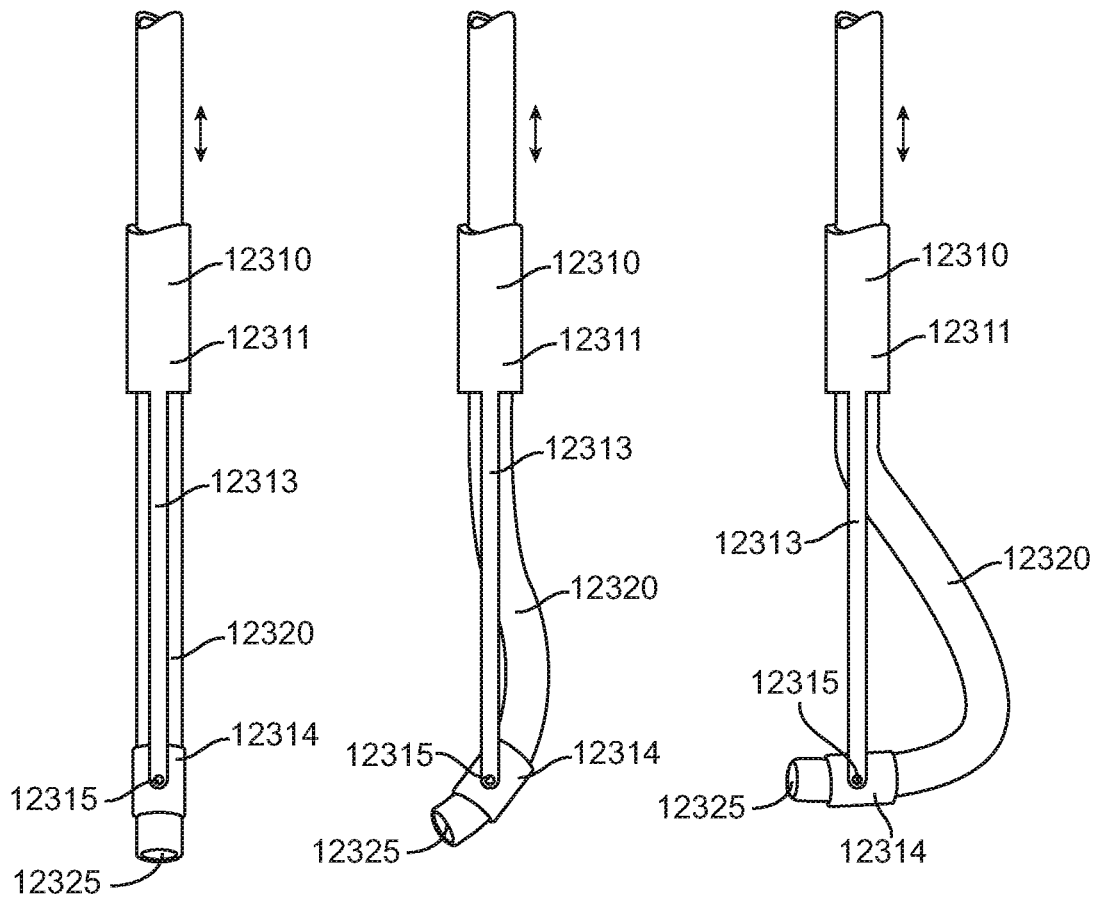
FIGS. 123A-123D show an exemplary catheter director according to embodiments of the invention.
Figure 123D:
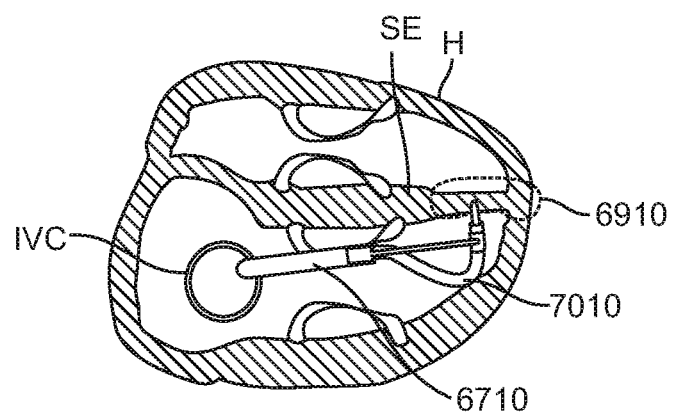

FIGS. 123A-123D show an exemplary catheter director 12310 according to embodiments of the invention. As shown in FIG. 123D, catheter director 12310 may be used to direct second catheter sheath 7010 toward region 6910 of the septum SE. Catheter director 12310 comprises a main body 12311 coupled to a distal body 12314 through an elongate portion 12313 and an articulated hinge 12315. A flexible sheath 12320 can be disposed within main body 12311 and distal body 12314. Distal body 12314 is coupled to the distal end of sheath 12320. As shown in FIGS. 123A-123C, flexible sheath 12320 can be advanced distally. Distal body 12314 holds the distal end of sheath 12320 in place as it is advanced but allows distal end of sheath 12320 to change orientations. As sheath 12320 is advanced distally, some "slack" is added to sheath 12320 between pivot or hinge 12315 and main body 12311 and the direction to which aperture 12325 of flexible sheath 12320 faces is oriented laterally, in a controlled manner, so that this mechanism causes sheath 7010 to curve within the ventrical away from the septum and then back toward the septum.

Figure 124A:
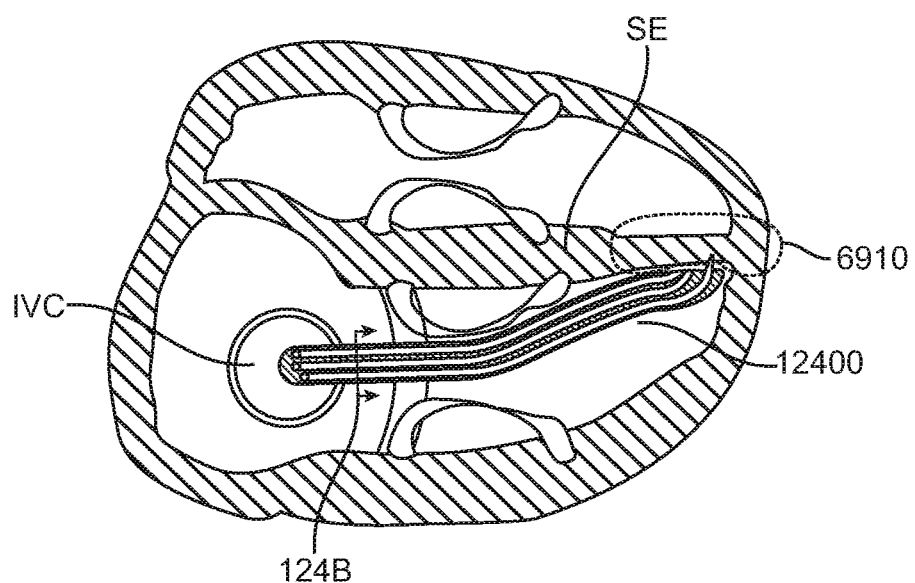

FIGS. 124A-124E show an exemplary second catheter sheath 12400 according to embodiments of the invention. Second catheter sheath 12400 may be used similarly to how second catheter sheath 7010 is used as described above. FIG. 124A shows second catheter 12400 positioned in heart H.

Second catheter sheath 12400 comprises multiple lumens 12435 as shown in the cross-section of second catheter sheath 12400 shown by FIG. 124B. Although three lumens 12435 are shown, any number of lumens 12435 can be envisioned. As shown in FIGS. 124C and 124E, lumens 12435 lead to apertures 12436. Apertures 12436 are spaced at set distanced from each other and are predictably proximal from the apex of second catheter sheath 12400. One of the lumens 12435 can be used to direct a guidewire and/or dilator while the other two lumens may be used to stabilize the catheter, for example, with suction. After an anchor assembly 580 is positioned in the heart as desired, another of the lumens 12435 can be used to direct the guidewire and/or dilator while other two lumens can be used to stabilize the catheter, for example, with suction. After a second anchor assembly 580 is positioned in the heart, the remaining lumen 12435 can be used to direct the guidewire and/or dilator while the other two lumens can be used to stabilize the catheter, for example, with suction. Thus, anchor assemblies 580 can be positioned in the heart at set distances from each other and in predictable positions.

Figure 125B:
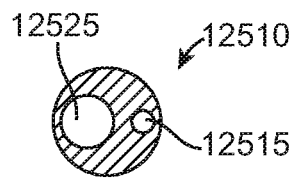
FIGS. 125A-125C show an exemplary second catheter sheath 12510 according to embodiments of the invention.
Figure 125A:
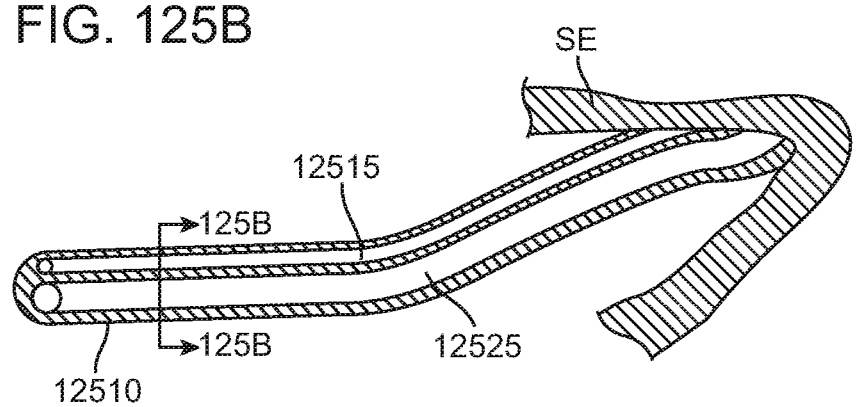
Figure 125C:
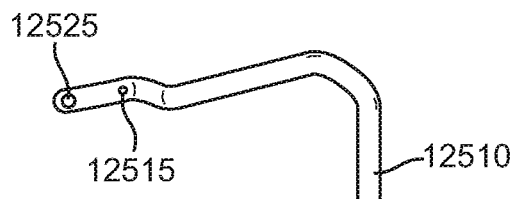

FIGS. 125A-125C show an exemplary second catheter sheath 12510 according to embodiments of the invention. Second catheter sheath 12510 may be used similarly to how second catheter sheaths 7010 and 12400 are used as described above. FIG. 125A shows an exemplary second catheter sheath 12510 positioned against septum SE. FIG. 125B shows the cross section of second catheter sheath 12510 which comprises a device lumen 12525 and a suction lumen 12515. A guidewire or dilator may be advanced through device lumen 12525 while suction may be affected through suction lumen 12515 to stabilize second catheter sheath 12510. FIG. 125C shows a perspective view of second catheter sheath 12510.

Figure 126:
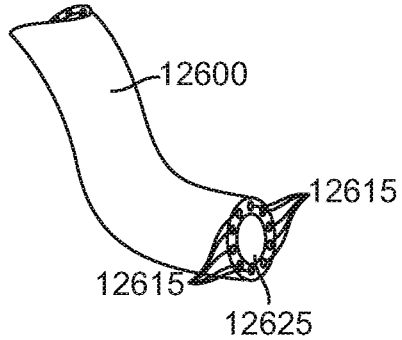
FIG. 126 shows a second catheter sheath 12510 comprising a device lumen 12625 and a plurality of suction lumens.

Other exemplary second catheter sheaths can be envisioned. For example, FIG. 126 shows a second catheter sheath 12510 comprising a device lumen 12625 and a plurality of suction lumens 12615. A guidewire or dilator may be advanced through device lumen 12625 while suction may be affected through suction lumens 12615 to stabilize second catheter sheath 12510. Suction lumens 12615 are arranged concentrically about device lumen 12625.

While exemplary embodiments have been described in some detail, it is understood that various modifications and changes could readily be made without departing from the spirit of the invention, which is solely limited by the appended claims.

What is claimed is:

1. A system for treating a heart, the heart having a chamber bordered by a wall, the system comprising:
   a first catheter having a lumen that extends along a longitudinal length of the first catheter;
   a guidewire that is insertable through a perforation in the wall of the heart;
   a second catheter that is separate from the first catheter, the second catheter being insertable over the guidewire through the wall of the heart;
   a balloon that is coupled with a distal end of the second catheter, the balloon being insertable through the wall in a deflated state and the balloon being inflatable so that upon proximal retraction of the second catheter relative to the wall, an axially oriented outer surface of the balloon engages with the wall;
   an anchor that is engageable with the wall; and
   a tension member that is coupled with the anchor so that the anchor is tensionable, via the tension member, to urge the wall toward another wall positioned on an opposite side of the chamber;

wherein the second catheter includes a fluid port that is fluidly coupled with the balloon such that a fluid is deliverable through the fluid port to the balloon to inflate the balloon.

2. The system of claim 1, wherein the fluid port is configured so that the fluid is retractable from the balloon and through the fluid port to deflate the balloon.

3. The system of claim 2, wherein the fluid that is delivered to the balloon or retracted therefrom consists of saline.

4. The system of claim 1, wherein the fluid port is fluidly coupled to the balloon via a radially extending port between the balloon and the fluid port.

5. The system of claim 1, wherein the balloon comprises a first balloon component and a second balloon component that is positioned distally of the first balloon component.

6. The system of claim 5, wherein the first balloon component and the second balloon component have different outer diameters when inflated.

7. The system of claim 5, wherein the first balloon component and the second balloon component are separated from one another by a gap.

8. The system of claim 5, wherein the second balloon component is configured to dilate the perforation in the wall.

9. The system of claim 1, wherein the balloon is a second balloon and wherein the system includes a first balloon coupled with the first catheter.

10. The system of claim 9, wherein the first balloon is inflatable independently of the second balloon and the second balloon is inflatable independently of the first balloon.

11. The system of claim 9, wherein the first catheter and first balloon are moveable independently of the second catheter and second balloon.

12. The system of claim 1, wherein the system includes a plug having a tail structure that is configured to fit into the perforation in the wall to block or seal the perforation in the wall.

13. A method of treating a heart comprising:
advancing a first catheter through a perforation in a first wall of the heart;
inserting a guidewire through the perforation in the first wall of the heart so that a distal end of the guidewire is positioned in a chamber of the heart;
advancing a second catheter over the guidewire toward the first wall of the heart;
inserting a balloon through the first wall of the heart with the balloon in a deflated state, the balloon being insertable through the first wall so that the balloon is positioned distally of the first wall;
inflating the balloon by delivering fluid through a fluid port to the balloon;
engaging the balloon with the first wall of the heart; and
retracting the balloon proximally relative to the first wall to urge the first wall toward a second wall of the heart.

14. The method of claim 13, further comprising retracting the fluid from the balloon to deflate the balloon.

15. The method of claim 13, wherein the balloon is coupled with a distal end of the second catheter, and wherein the method further comprises retracting the first catheter through a lumen of the second catheter, and through the perforation in the first wall, upon inflation of the balloon of the balloon and engagement of the balloon with the first wall.

16. The method of claim 13, wherein the balloon is a second balloon that is coupled with the second catheter, and wherein a first balloon is coupled with the first catheter.

17. The method of claim 16, wherein the method further comprises inflating the first balloon independently of the second balloon, or the method further comprises moving the first catheter and first balloon independently of the second catheter and second balloon.

18. The method of claim 13, wherein the balloon comprises a first balloon component and a second balloon component that is positioned distally of the first balloon component.

19. The method of claim 13, further comprising inserting a plug having a tail structure into the perforation in the first wall to block or seal the perforation in the first wall.

* * * * *